United States Patent
Hoveyda et al.

(10) Patent No.: US 11,731,974 B2
(45) Date of Patent: *Aug. 22, 2023

(54) N-ACYL-(3-SUBSTITUTED)-(8-SUBSTITUTED)-5,6-DIHYDRO-[1,2,4]TRIAZOLO[4,3-A]PYRAZINES AS SELECTIVE NK-3 RECEPTOR ANTAGONISTS

(71) Applicant: Ogeda SA, Anderlecht (BE)

(72) Inventors: Hamid R. Hoveyda, Brussels (BE); Guillaume Dutheuil, Vedrin (BE); Graeme Fraser, Bousval (BE)

(73) Assignee: Ogeda SA, Charleroi (BE)

( * ) Notice: Subject to any disclaimer, the term of this patent is extended or adjusted under 35 U.S.C. 154(b) by 302 days.

This patent is subject to a terminal disclaimer.

(21) Appl. No.: 17/066,086

(22) Filed: Oct. 8, 2020

(65) Prior Publication Data

US 2021/0094959 A1    Apr. 1, 2021

Related U.S. Application Data

(63) Continuation of application No. 16/204,390, filed on Nov. 29, 2018, now Pat. No. 10,836,768, which is a continuation of application No. 15/796,028, filed on Oct. 27, 2017, now Pat. No. 10,183,948, which is a continuation-in-part of application No. 15/371,600, filed on Dec. 7, 2016, now Pat. No. 9,987,274, which is a continuation-in-part of application No. 15/205,304, filed on Jul. 8, 2016, now Pat. No. 10,030,025, which is a continuation of application No. 14/694,228, filed on Apr. 23, 2015, now Pat. No. 9,422,299, which is a continuation-in-part of application No. PCT/EP2014/056367, filed on Mar. 28, 2014.

(30) Foreign Application Priority Data

| Mar. 29, 2013 | (EP) | 13161863 |
| Nov. 15, 2013 | (EP) | 13193025 |
| Feb. 7, 2014 | (EP) | 14154303 |

(51) Int. Cl.
    *C07D 487/04*     (2006.01)

(52) U.S. Cl.
    CPC .................. *C07D 487/04* (2013.01)

(58) Field of Classification Search
    CPC .................................................. C07D 487/04
    USPC ....................................................... 544/350
    See application file for complete search history.

(56) References Cited

U.S. PATENT DOCUMENTS

| | | | |
|---|---|---|---|
| 7,307,164 B2 | 12/2007 | Brockunier et al. | |
| 8,188,084 B2 | 5/2012 | Jones et al. | |
| 8,513,248 B2 | 8/2013 | Dean et al. | |
| 8,557,841 B2 | 10/2013 | Yu et al. | |
| 8,871,761 B2 | 10/2014 | Hoveyda et al. | |
| 9,422,299 B2 | 8/2016 | Hoveyda et al. | |
| 9,969,738 B2 | 5/2018 | Hoveyda et al. | |
| 9,987,274 B2 | 6/2018 | Hoveyda et al. | |
| 10,030,025 B2 | 7/2018 | Hoveyda et al. | |
| 10,065,961 B2 | 9/2018 | Hoveyda et al. | |
| 10,183,948 B2 | 1/2019 | Hoveyda et al. | |
| 10,836,768 B2 | 11/2020 | Hoveyda et al. | |
| 2005/0107390 A1 | 5/2005 | Brockunier et al. | |
| 2007/0185095 A1 | 8/2007 | Johansson et al. | |
| 2008/0275052 A1 | 11/2008 | Dhar et al. | |
| 2009/0176765 A1 | 7/2009 | Jones et al. | |
| 2011/0003820 A1 | 1/2011 | Henrich et al. | |
| 2012/0172366 A1 | 7/2012 | Dean et al. | |
| 2012/0252799 A1 | 10/2012 | Yu et al. | |
| 2014/0275097 A1 | 9/2014 | Hoveyda et al. | |
| 2014/0371218 A1 | 12/2014 | Hoveyda et al. | |
| 2015/0315199 A1 | 11/2015 | Hoveyda et al. | |
| 2016/0289233 A1 | 10/2016 | Hoveyda et al. | |

FOREIGN PATENT DOCUMENTS

| WO | 2000/43008 A1 | 7/2000 |
| WO | 2003/082817 A2 | 10/2003 |
| WO | 2004/021984 A2 | 3/2004 |
| WO | 2004/103953 A1 | 12/2004 |
| WO | 2005/080397 A2 | 9/2005 |

(Continued)

OTHER PUBLICATIONS

U.S. Appl. No. 14/694,228, filed Apr. 23, 2015, U.S. Pat. No. 9,422,299, Issued.

(Continued)

*Primary Examiner* — Douglas M Willis

(74) *Attorney, Agent, or Firm* — McCarter & English, LLP; Maria Laccotripe Zacharakis

(57) ABSTRACT

A method for treating and/or preventing polycystic ovary syndrome (PCOS) including the administration, to a patient in need thereof, of a pharmaceutically effective amount of a compound of Formula I

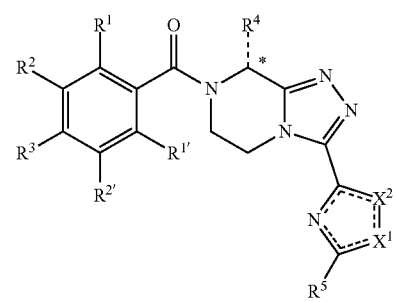

or a pharmaceutically acceptable solvate thereof.

8 Claims, 5 Drawing Sheets

(56) References Cited

FOREIGN PATENT DOCUMENTS

| WO | 2006/120478 A2 | 11/2006 |
|----|----------------|---------|
| WO | 2007/138351 A2 | 12/2007 |
| WO | 2009/095253 A1 | 8/2009  |
| WO | 2009/095254 A1 | 8/2009  |
| WO | 2010/125101 A1 | 11/2010 |
| WO | 2010/125102 A1 | 11/2010 |
| WO | 2011/121137 A1 | 10/2011 |
| WO | 2013/050424 A1 | 4/2013  |
| WO | 2016/046398 A1 | 3/2016  |

OTHER PUBLICATIONS

U.S. Appl. No. 15/205,304, filed Jul. 8, 2016, U.S. Pat. No. 10,030,025, Issued.

U.S. Appl. No. 15/371,600, filed Dec. 7, 2016, U.S. Pat. No. 9,987,274, Issued.

U.S. Appl. No. 15/796,028, filed Oct. 27, 2017, U.S. Pat. No. 10,183,948, Issued.

U.S. Appl. No. 16/204,390, filed Nov. 29, 2018, U.S. Pat. No. 10,836,768, Issued.

Bottomley et al., Structural and functional analysis of the human HDAC4 catalytic domain reveals a regulatory structural zinc-binding domain. J Biol Chem. Sep. 26, 2008;283(39):26694-704.

Burke et al., Coexpression of dynorphin and neurokinin B immunoreactivity in the rat hypothalamus: Morphologic evidence of interrelated function within the arcuate nucleus. J Comp Neurol. Oct. 10, 2006;498(5):712-26.

Copel et al., Activation of neurokinin 3 receptor increases Na(v)1.9 current in enteric neurons. J Physiol. Apr. 1, 2009;587(Pt7):1461-79.

Dawson et al., Therapeutic utility of NK3 receptor antagonists for the treatment of schizophrenia. Curr Pharm Des. Jan. 2010;16(3):344-57.

Fioramonti et al., Intestinal anti-nociceptive behaviour of NK3 receptor antagonism in conscious rats: evidence to support a peripheral mechanism of action. Neurogastroenterol Motil. Aug. 2003;15(4):363-9.

Giardina et al., Recent advances in neurokinin-3 receptor antagonists Exp Opin Ther Patents. 2000;10(6):939-60.

Goodman et al., Evidence that dynorphin plays a major role in mediating progesterone negative feedback on gonadotropin-releasing hormone neurons in sheep. Endocrinology. Jun. 2004;145(6):2959-67.

Hackam et al., Translation of research evidence from animals to humans. JAMA. Oct. 11, 2006;296(14):1731-2.

Houghton et al., Effect of the NK(3) receptor antagonist, talnetant, on rectal sensory function and compliance in ealthy humans. Neurogastroenterol Motil. Sep. 2007;19(9):732-43.

Jordan, Tamoxifen: a most unlikely pioneering medicine. Nat Rev Drug Discov. Mar. 2003;2(3):205-13.

Krajewski et al., Morphologic evidence that neurokinin B modulates gonadotropin-releasing hormone secretion via neurokinin 3 receptors in the rat median eminence J Comp Neurol. Aug. 29, 2005;489(3):372-86.

Lomax et al., Neurochemical classification of enteric neurons in the guinea-pig distal colon. Cell Tissue Res. Oct. 2000,302(1):59-72.

Meli Zer et al., Meta-Trial Study Group. Placebo-controlled evaluation of four novel compounds for the treatment of schizophrenia and schizoaffective disorder. Am J Psychiatry Jun. 2004;161(6):975-84.

Murali Dhar et al., Synthesis and SAR of p38alpha MAP kinase inhibitors based on heterobicyclic scaffolds. Bioorg Med Chem Lett. Sep. 15, 2007;17(18):5019-24.

Navarro et al., Regulation of gonadotropin-releasing hormone secretion by kisspeptin/dynorphin/neurokinin B neurons in the arcuate nucleus of the mouse. J Neurosci Sep. 23, 2009;29(38):11859-66.

Rick et al., Combining growth hormone-releasing hormone antagonist with luteinizing hormone-releasing hormone antagonist greatly augments benign prostatic hyperplasia shrinkage J Urol. Apr. 2012;187(4):1498-504.

Scolnik et al., Comparative study of experimentally induced benign and atypical hyperplasia in the ventral prostate of different rat strains. J Androl. Jul.-Aug. 1994;15(4):287-97.

Shafton et al., Effects of the peripherally acting NK receptor antagonist, SB-235375, on intestinal and somatic nociceptive responses and on intestinal motility in anaesthetized rats. Neurogastroenterol Motil. Apr. 2004;16(2):223-31.

Vippagunta et al., Crystalline solids. Adv Drug Deliv Rev. May 16, 2001;48(1):3-26.

International Search Report and Written Opinion for Application No. PCT/EP2011/055218, dated Jun. 8, 2011, 10 pages.

International Search Report and Written Opinion for Application No. PCT/EP2012/069546, dated Nov. 29, 2012, 14 pages.

International Search Report and Written Opinion for Application No. PCT/EP2014/056367, dated Apr. 28, 2014, 8 pages.

N-ACYL-(3-SUBSTITUTED)-(8-SUBSTITUTED)-5,6-DIHYDRO-[1,2,4]TRIAZOLO[4,3-A]PYRAZINES AS SELECTIVE NK-3 RECEPTOR ANTAGONISTS

RELATED APPLICATION INFORMATION

This application is a continuation of U.S. patent application Ser. No. 16/204,390, filed Nov. 29, 2018, which is a continuation of U.S. patent application Ser. No. 15/796,028, filed Oct. 27, 2017, which is a continuation-in-part of U.S. patent application Ser. No. 15/371,600, filed Dec. 7, 2016, which is a continuation-in-part of U.S. patent application Ser. No. 15/205,304, filed Jul. 8, 2016, which is a continuation of U.S. patent application Ser. No. 14/694,228, filed Apr. 23, 2015, which is a continuation-in-part of International Application No.: PCT/EP2014/056367, filed Mar. 28, 2014, which claims priority from EP Application No.: 14154303.3, filed Feb. 7, 2014; EP Application No.: 13193025.7, filed Nov. 15, 2013; and EP Application No.: 13161863.9, filed Mar. 29, 2013. The entire contents of these applications are incorporated herein by reference in their entirety.

FIELD OF INVENTION

The present invention relates to novel N-acyl-(3-substituted)-(8-substituted)-5,6-dihydro-[1,2,4]triazolo[4,3-a]pyrazines including their pharmaceutically acceptable solvates that are selective antagonists to neurokinin-3 receptor (NK-3) and are useful as therapeutic compounds, particularly in the treatment and/or prevention of a broad array of CNS and peripheral diseases or disorders.

BACKGROUND OF INVENTION

Tachykinin receptors are the targets of a family of structurally related peptides which include substance P (SP), neurokinin A (NKA) and neurokinin B (NKB), named collectively "tachykinins". Tachykinins are synthesized in the central nervous system (CNS) and peripheral tissues, where they exert a variety of biological activities. Three tachykinin receptors are known which are named neurokinin-1 (NK-1), neurokinin-2 (NK-2) and neurokinin-3 (NK-3) receptors. Tachykinin receptors belong to the rhodopsin-like seven membrane G-protein coupled receptors. SP has the highest affinity and is believed to be the endogenous ligand of NK-1, NKA for NK-2 receptor and NKB for NK-3 receptor, although cross-reactivity amongst these ligands does exist. The NK-1, NK-2 and NK-3 receptors have been identified in different species. NK-1 and NK-2 receptors are expressed in a wide variety of peripheral tissues and NK-1 receptors are also expressed in the CNS; whereas NK-3 receptors are primarily expressed in the CNS.

The neurokinin receptors mediate a variety of tachykinin-stimulated biological effects that include transmission of excitatory neuronal signals in the CNS and periphery (e.g. pain), modulation of smooth muscle contractile activity, modulation of immune and inflammatory responses, induction of hypotensive effects via dilatation of the peripheral vasculature and stimulation of endocrine and exocrine gland secretions.

In the CNS, the NK-3 receptor is expressed in regions including the medial prefrontal cortex, the hippocampus, the thalamus and the amygdala. Moreover, NK-3 receptors are expressed on dopaminergic neurons. Activation of NK-3 receptors has been shown to modulate dopamine, acetylcholine and serotonin release suggesting a therapeutic utility for NK-3 receptor modulators for the treatment of a variety of disorders including psychotic disorders, anxiety, depression, schizophrenia as well as obesity, pain or inflammation (Giardina et al., Exp. Opinion Ther. Patents, 2000, 10(6), 939-960; Current Opinion in Investigational Drugs, 2001, 2(7), 950-956 and Dawson and Smith, Current Pharmaceutical Design, 2010, 16, 344-357).

Schizophrenia is classified into subgroups. The paranoid type is characterized by delusions and hallucinations and absence of thought disorder, disorganized behavior, and affective flattening. In the disorganized type, which is also named 'hebephrenic schizophrenia' in the International Classification of Diseases (ICD), thought disorder and flat affect are present together. In the catatonic type, prominent psychomotor disturbances are evident, and symptoms may include catatonic stupor and waxy flexibility. In the undifferentiated type, psychotic symptoms are present but the criteria for paranoid, disorganized, or catatonic types have not been met. The symptoms of schizophrenia normally manifest themselves in three broad categories, i.e. positive, negative and cognitive symptoms. Positive symptoms are those, which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as a lack of sustained attention and deficits in decision making. The current antipsychotic drugs (APDs) are fairly successful in treating the positive symptoms but fare less well for the negative and cognitive symptoms. Contrary to that, NK-3 antagonists have been shown clinically to improve on both positive and negative symptoms in schizophrenics (Meltzer et al, Am. J. Psychiatry, 2004, 161, 975-984) and ameliorate cognitive behavior of schizophrenics (Curr. Opion. Invest. Drug, 2005, 6, 717-721).

In rat, morphological studies provide evidence for putative interactions between NKB neurons and the hypothalamic reproductive axis (Krajewski et al, J. Comp. Neurol., 2005, 489(3), 372-386). In arcuate nucleus neurons, NKB expression co-localizes with estrogen receptor α and dynorphin, implicated in progesterone feedback to Gonadotropin Releasing Hormone (GnRH) secretion (Burke et al., J. Comp. Neurol., 2006, 498(5), 712-726; Goodman et al., Endocrinology, 2004, 145(6), 2959-2967). Moreover, NK-3 receptor is highly expressed in the hypothalamic arcuate nucleus in neurons which are involved in the regulation of GnRH release.

WO 00/43008 discloses a method of suppressing gonadotropin and/or androgen production with specific NK-3 receptor antagonists. More particularly, the WO 00/43008 application relates to lowering luteinizing hormone (LH) blood level by administering an NK-3 receptor antagonist. Concurrently or alternatively with gonadotropin suppression, WO 00/43008 also relates to suppression of androgen production with NK-3 receptor antagonists. Recently it has been postulated that NKB acts autosynaptically on kisspeptin neurons in the arcuate nucleus to synchronize and shape the pulsatile secretion of kisspeptin and drive the release of GnRH from fibers in the median eminence (Navarro et al., J. of Neuroscience, 2009, 23(38), 11859-11866). All these observations suggest a therapeutic utility for NK-3 receptor modulators for sex hormone-dependent diseases.

NK-3 receptors are also found in the human myenteric and submucosal plexus of the sigmoid colon as well as in the gastric fundus (Dass et al., Gastroenterol., 2002, 122 (Suppl 1), Abstract M1033) with particular expression noted on myenteric intrinsic primary afferent neurons (IPANs) (Lomax and Furness, Cell Tissue Res, 2000, 302, 59-3). Intense stimulation of IPANs changes patterns of intestinal motility and intestinal sensitivity. Electrophysiology experiments have shown that activation of the NK-3 receptor changes the voltage threshold of action potentials in IPANs and promotes the generation of long-lasting plateau potentials (Copel et al., J Physiol, 2009, 587, 1461-1479) that may sensitize these neurons to mechanical and chemical stimuli leading to effects on gut motility and secretion. Similarly, Irritable Bowel Syndrome (IBS) is characterized by patient hypersensitivity to mechanical and chemical stimuli. Thus, NK-3 antagonists have been tested in preclinical models of IBS where they have been shown to be effective to reduce nociceptive behavior caused by colo-rectal distension (Fioramonti et al., Neurogastroenterol Motil, 2003, 15, 363-369; Shafton et al., Neurogastroenterol Motil, 2004, 16, 223-231) and, on this basis, NK-3 antagonists have been advanced into clinical development for the treatment of IBS (Houghton et al., Neurogastroenterol Motil, 2007, 19, 732-743; Dukes et al., Gastroenterol, 2007, 132, A60).

Non-peptide antagonists have been developed for each of the tachykinin receptors. Some of them have been described as dual modulators able to modulate both NK-2 and NK-3 receptors (WO 06/120478). However, known non-peptide NK-3 receptor antagonists suffer from a number of drawbacks, notably poor safety profile and limited CNS penetrability that may limit the success of these compounds in clinical development.

On this basis, new potent and selective antagonists of NK-3 receptor may be of therapeutic value for the preparation of drugs useful in the treatment and/or prevention of CNS and peripheral diseases or disorders in which NKB and the NK-3 receptors are involved.

Target potency alone, which may be demonstrated by competitive binding data, is not sufficient for drug development. Rather, efficacy in vivo is contingent upon achieving a relevant "free" drug concentration relative to the target potency at the physiological site of action. Drug molecules typically bind reversibly to proteins and lipids in plasma. The "free" fraction refers to the drug concentration that is unbound and therefore available to engage the biological target and elicit pharmacological activity. This free fraction is commonly determined using plasma protein binding (PPB) assays. The free drug fraction is relevant to not only achieving the desired pharmacological activity, but also potentially undesirable activities including rapid hepatic metabolism (leading to high first-pass clearance and thereby poor oral bioavailability) as well as possible off-target activities that can lead to safety concerns (for example, inhibition of hERG ion channel activity, a widely accepted marker of cardiovascular toxicity).

The invention thus encompasses compounds of general Formula I, their pharmaceutically acceptable solvates as well as methods of use of such compounds or compositions comprising such compounds as antagonists to the NK-3 receptor. Compounds of Formula I are N-acyl-(3-substituted)-(8-substituted)-5,6-dihydro-[1,2,4]triazolo[4,3-a]pyrazines. The compounds of the invention are generally disclosed in international patent application WO2011/121137 but none is specifically exemplified therein. On another hand, unsubstituted and thus non-chiral 5,6,7,8-tetrahydro[1,2,4]triazolo[4,3-a]pyrazines have been disclosed in WO2010/125102 as modulators of an unrelated target, namely P2X7.

SUMMARY OF THE INVENTION

In a general aspect, the invention provides compounds of general Formula I:

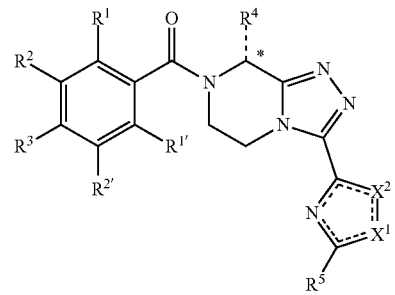

and pharmaceutically acceptable solvates thereof, wherein:
$R^1$ is H, F or methyl;
$R^{1'}$ is H;
$R^2$ is H, F, Cl or methoxy;
$R^{2'}$ is H or F;
$R^3$ is H, F, Cl, methyl, trifluoromethyl, nitrile or $R^3$ is thiophen-2-yl under the condition that $R^5$ is not methyl;
$R^4$ is methyl, ethyl, n-propyl, hydroxyethyl, methoxyethyl, trifluoromethyl, difluoromethyl or fluoromethyl;
$R^5$ is methyl, ethyl, methoxymethyl, trifluoromethyl, difluoromethyl, fluoromethyl, 1-fluoroethyl, 1,1-difluoroethyl or 2,2,2-trifluoroethyl, preferably
$R^5$ is methyl, ethyl, methoxymethyl, trifluoromethyl, difluoromethyl or fluoromethyl;
$X^1$ is N and $X^2$ is S or O; or $X^1$ is S and $X^2$ is N;
represents a single or a double bound depending on $X^1$ and $X^2$;
⋮⋮⋮stands for the (R)-enantiomer or for the racemate of compound of Formula I.

In another aspect, the present invention provides a pharmaceutical composition comprising at least one compound according to the invention or a pharmaceutically acceptable solvate thereof.

The invention also relates to the use of the above compounds or their pharmaceutically acceptable solvates as modulators of NK-3 receptors, preferably as antagonists of NK-3 receptors.

The invention also relates to the use of the above compounds or their pharmaceutically acceptable solvates as lowering agents of the circulating LH levels.

The invention further provides methods of treatment and/or prevention of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis comprising the administration of a therapeutically effective amount of a compound or pharmaceutically acceptable solvate of Formula I, to a patient in need thereof. The invention further provides methods of treatment and/or prevention of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, urinary incontinence, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis comprising the administration of a therapeutically effective amount of a compound or pharmaceutically acceptable solvate of Formula I, to a patient in need thereof. Preferably the patient is a warm-blooded animal, more preferably a human.

The invention further provides methods of treatment for gynecological disorders and infertility. In particular, the invention provides methods to lower and/or suppress the LH-surge in assisted conception comprising the administration of a therapeutically effective amount of a compound or pharmaceutically acceptable solvate of Formula I, to a patient in need thereof. Preferably the patient is a warm-blooded animal, more preferably a woman.

The invention further provides methods to affect androgen production to cause male castration and to inhibit the sex drive in male sexual offenders comprising the administration of a therapeutically effective amount of a compound or pharmaceutically acceptable solvate of Formula I, to a patient in need thereof. Preferably the patient is a warm-blooded animal, more preferably a man.

The invention also provides the use of a compound of Formula I or a pharmaceutically acceptable solvate thereof as a medicament. Preferably, the medicament is used for the treatment and/or prevention of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis. Preferably, the medicament is used for the treatment and/or prevention of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, urinary incontinence, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis. The medicament may also be used for the treatment of gynecologic disorders, infertility and to affect androgen production to cause male castration.

DETAILED DESCRIPTION OF THE INVENTION

Figure 1:
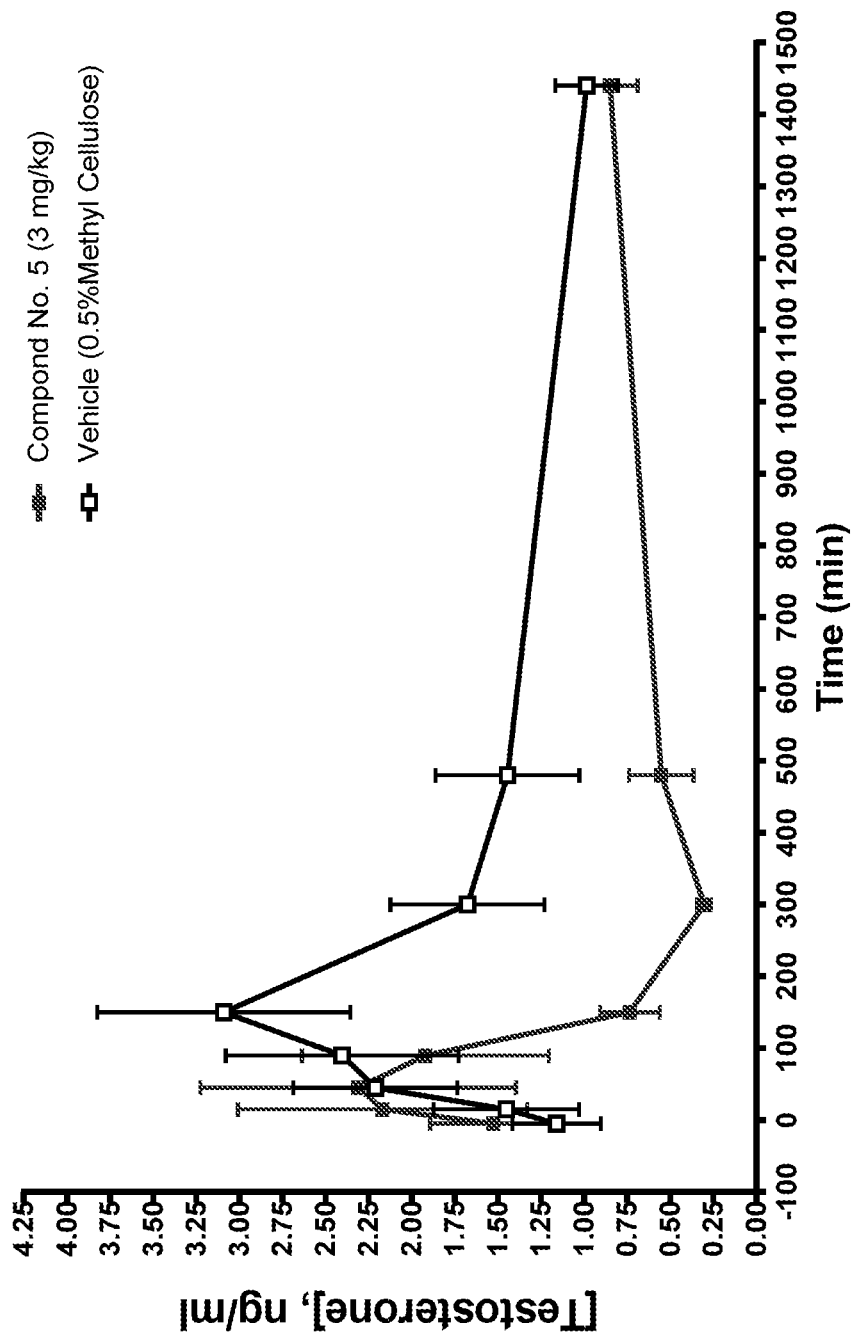
FIG. 1 is a graph showing the plasma testosterone levels over time in intact male rats after oral administration of compound no 5 (3 mg/kg) or of a vehicle (0.5% methyl cellulose).

As noted above, the invention relates to compounds of Formula I:

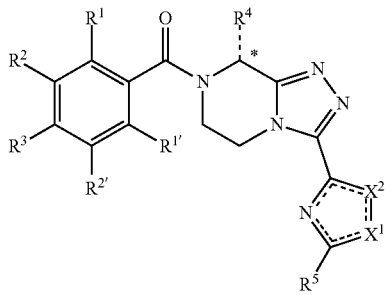

and pharmaceutically acceptable solvates thereof, wherein:
$R^1$ is H, F or methyl;
$R^{1'}$ is H;
$R^2$ is H, F, Cl or methoxy;
$R^{2'}$ is H or F;
$R^3$ is H, F, Cl, methyl, trifluoromethyl, nitrile or $R^3$ is thiophen-2-yl under the condition that $R^5$ is not methyl;
$R^4$ is methyl, ethyl, n-propyl, hydroxyethyl, methoxyethyl, trifluoromethyl, difluoromethyl or fluoromethyl;
$R^5$ is methyl, ethyl, methoxymethyl, trifluoromethyl, difluoromethyl, fluoromethyl, 1-fluoroethyl, 1,1-difluoroethyl or 2,2,2-trifluoroethyl, preferably $R^5$ is methyl, ethyl, methoxymethyl, trifluoromethyl, difluoromethyl or fluoromethyl;
$X^1$ is N and $X^2$ is S or O; or $X^1$ is S and $X^2$ is N;
represents a single or a double bound depending on $X^1$ and $X^2$;
$\overset{*}{\text{---}}$ stands for the (R)-enantiomer or for the racemate of compound of Formula I.

In one specific embodiment of the invention, $R^5$ is methyl, ethyl, methoxymethyl, trifluoromethyl, difluoromethyl, fluoromethyl, 1-fluoroethyl, 1,1-difluoroethyl or 2,2,2-trifluoroethyl. In another specific embodiment, $R^5$ is methyl, ethyl, methoxymethyl, trifluoromethyl, difluoromethyl or fluoromethyl. In another specific embodiment, $R^5$ is 1-fluoroethyl, 1,1-difluoroethyl or 2,2,2-trifluoroethyl. Preferred compounds of Formula I and pharmaceutically acceptable solvates thereof are those wherein:
$R^1$ is H, F or methyl;
$R^{1'}$ is H;
$R^2$ is H, F, Cl or methoxy;
$R^{2'}$ is H or F;
$R^3$ is H, F, Cl, methyl, trifluoromethyl, nitrile or $R^3$ is thiophen-2-yl under the condition that $R^5$ is not methyl;
$R^4$ is methyl, ethyl, n-propyl or hydroxyethyl;
$R^5$ is methyl, ethyl, trifluoromethyl, difluoromethyl, 1-fluoroethyl, 1,1-difluoroethyl or 2,2,2-trifluoroethyl, preferably $R^5$ is methyl, ethyl or trifluoromethyl;
$X^1$ is N and $X^2$ is S or O, preferably $X^1$ is N and $X^2$ is S.

In an embodiment of the invention, compound of Formula I is the (R)-enantiomer. In another embodiment, compound of Formula I is the racemate.

In one embodiment, preferred compounds of Formula I are those of Formula I':

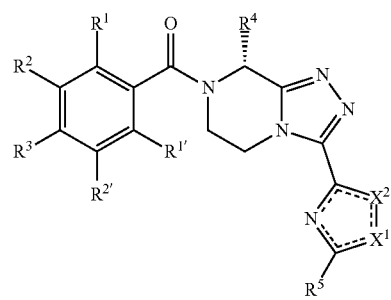

and pharmaceutically acceptable solvates thereof, wherein $R^1$, $R^{1'}$, $R^2$, $R^{2'}$, $R^3$, $R^4$, $R^5$, $X^1$ and $X^2$ are as defined in Formula I and represents a single or a double bound depending on $X^1$ and $X^2$.

In one embodiment, preferred compounds of Formula I are those of Formula I'':

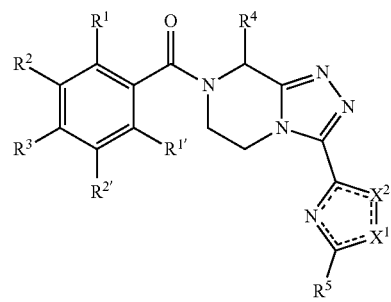

and pharmaceutically acceptable solvates thereof, wherein $R^1$, $R^{1'}$, $R^2$, $R^{2'}$, $R^3$, $R^4$, $R^5$, $X^1$ and $X^2$ are as defined in Formula I and represents a single or a double bound depending on $X^1$ and $X^2$.

In one embodiment, preferred compounds of Formula I are those of Formula Ia:

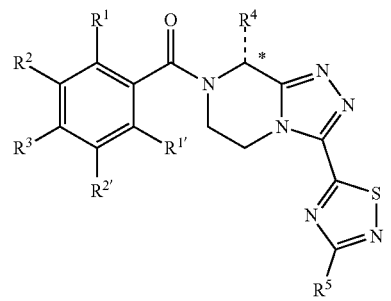

and pharmaceutically acceptable solvates thereof, wherein:
$R^1$ is H, F or methyl;
$R^{1'}$ is H;
$R^2$ is H, F, Cl or methoxy;
$R^{2'}$ is H or F;
$R^3$ is H, F, Cl, methyl, trifluoromethyl or nitrile;
$R^4$ is methyl, ethyl, n-propyl, hydroxyethyl, methoxyethyl, trifluoromethyl, difluoromethyl or fluoromethyl, preferably $R^4$ is methyl, ethyl, n-propyl or hydroxyethyl;

R⁵ is methyl, ethyl, methoxymethyl, trifluoromethyl, difluoromethyl, fluoromethyl, 1-fluoroethyl, 1,1-difluoroethyl or 2,2,2-trifluoroethyl, preferably R⁵ is methyl, ethyl, methoxymethyl, trifluoromethyl, difluoromethyl or fluoromethyl, preferably R⁵ is methyl, ethyl, trifluoromethyl or difluoromethyl, preferably R⁵ is methyl, ethyl or trifluoromethyl;

⋆--- stands for the (R)-enantiomer or for the racemate of compound of Formula Ia.

In one embodiment, preferred compounds of Formula Ia are those of Formula Ia' and Formula Ia":

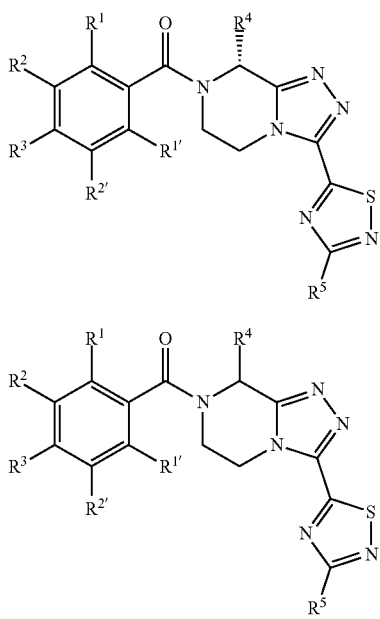

and pharmaceutically acceptable solvates thereof, wherein R¹, R¹', R², R²', R³, R⁴ and R⁵ are as defined in Formula Ia. Preferred compounds of Formula Ia' and Ia" and pharmaceutically acceptable solvates thereof are those wherein:
R¹ is H, F or methyl;
R¹' is H;
R² is H, F, Cl or methoxy;
R²' is H or F;
R³ is H, F, Cl, methyl, trifluoromethyl or nitrile;
R⁴ is methyl, ethyl, n-propyl or hydroxyethyl;
R⁵ is methyl, ethyl, trifluoromethyl or difluoromethyl, preferably R⁵ is methyl, ethyl or trifluoromethyl.

In one embodiment, preferred compounds of Formula Ia are those of Formula Ia-1:

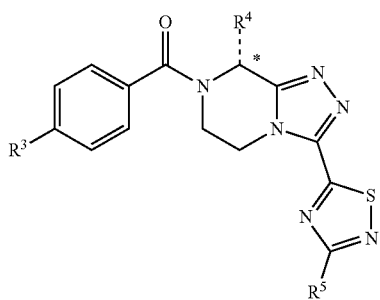

and pharmaceutically acceptable solvates thereof, wherein:
R³ is H, F, Cl, methyl, trifluoromethyl or nitrile, preferably R³ is H, F or Cl;
R⁴ is methyl, ethyl, n-propyl, hydroxyethyl, methoxyethyl, trifluoromethyl, difluoromethyl or fluoromethyl, preferably R⁴ is methyl, ethyl, n-propyl or hydroxyethyl;
R⁵ is methyl, ethyl, methoxymethyl, trifluoromethyl, difluoromethyl, fluoromethyl, 1-fluoroethyl, 1,1-difluoroethyl or 2,2,2-trifluoroethyl, preferably R⁵ is methyl, ethyl, methoxymethyl, trifluoromethyl, difluoromethyl or fluoromethyl, preferably R⁵ is methyl, ethyl, trifluoromethyl or difluoromethyl, preferably R⁵ is methyl, ethyl or trifluoromethyl; ⋆--- stands for the (R)-enantiomer or for the racemate.

In one embodiment, preferred compounds of Formula Ia-1 are those of Formula Ia-1':

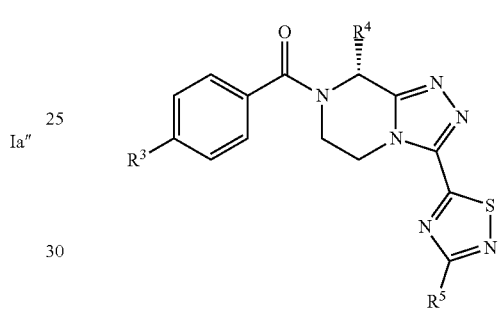

and pharmaceutically acceptable solvates thereof, wherein R³, R⁴ and R⁵ are as defined in Formula Ia-1.

In one embodiment, preferred compounds of Formula Ia are those of Formula Ia-2:

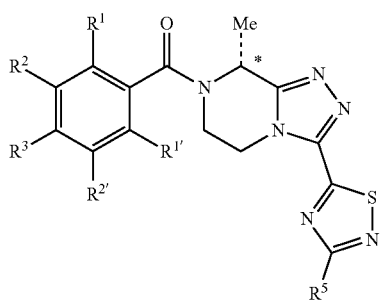

and pharmaceutically acceptable solvates thereof, wherein:
R¹ is H, F or methyl;
R¹' is H;
R² is H, F, Cl or methoxy;
R²' is H or F;
R³ is H, F, Cl, methyl, trifluoromethyl or nitrile;
R⁵ is methyl, ethyl, methoxymethyl, trifluoromethyl, difluoromethyl, fluoromethyl, 1-fluoroethyl, 1,1-difluoroethyl or 2,2,2-trifluoroethyl, preferably R⁵ is methyl, ethyl, methoxymethyl, trifluoromethyl, difluoromethyl or fluoromethyl, preferably R⁵ is methyl, ethyl, trifluoromethyl or difluoromethyl, preferably R⁵ is methyl, ethyl or trifluoromethyl;
⋆--- stands for the (R)-enantiomer or for the racemate.

In one embodiment, preferred compounds of Formula Ia-2 are those of Formula Ia-2':

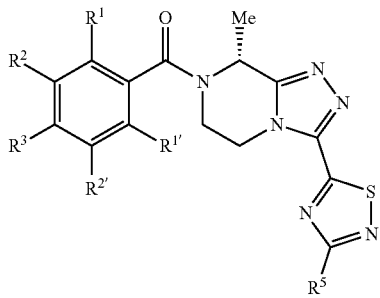

and pharmaceutically acceptable solvates thereof, wherein $R^1$, $R^{1'}$, $R^2$, $R^{2'}$, $R^3$ and $R^5$ are as defined in Formula Ia-2. In one embodiment, preferred compounds of Formula Ia are those of Formula Ia-3:

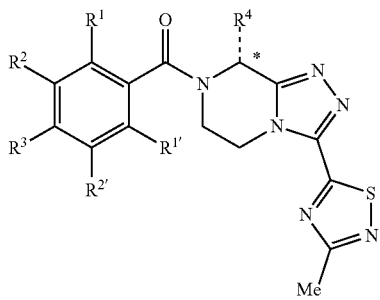

and pharmaceutically acceptable solvates thereof, wherein:
$R^1$ is H, F or methyl;
$R^{1'}$ is H;
$R^2$ is H, F, Cl or methoxy;
$R^{2'}$ is H or F;
$R^3$ is H, F, Cl, methyl, trifluoromethyl or nitrile;
$R^4$ is methyl, ethyl, n-propyl, hydroxyethyl, methoxyethyl, trifluoromethyl, difluoromethyl or fluoromethyl, preferably $R^4$ is methyl, ethyl, n-propyl or hydroxyethyl;
⁎--- stands for the (R)-enantiomer or for the racemate.

In one embodiment, preferred compounds of Formula Ia-3 are those of Formula Ia-3':

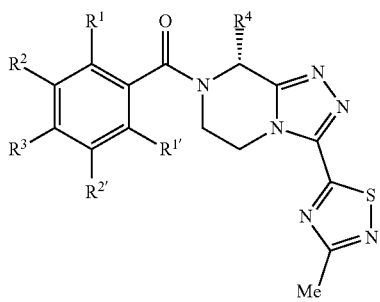

and pharmaceutically acceptable solvates thereof, wherein $R^1$, $R^{1'}$, $R^2$, $R^{2'}$, $R^3$ and $R^4$ are as defined in Formula Ia-3. In one embodiment, preferred compounds of Formula I are those of Formula Ib:

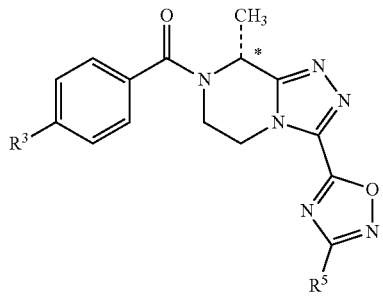

and pharmaceutically acceptable solvates thereof, wherein:
$R^3$ is F or $R^3$ is thiophen-2-yl under the condition that $R^5$ is not methyl;
$R^5$ is methyl, ethyl, trifluoromethyl, difluoromethyl, fluoromethyl, 1-fluoroethyl, 1,1-difluoroethyl or 2,2,2-trifluoroethyl, preferably $R^5$ is methyl, ethyl, trifluoromethyl, difluoromethyl or fluoromethyl, preferably $R^5$ is methyl, ethyl, 1-fluoroethyl, 1,1-difluoroethyl or 2,2,2-trifluoroethyl, preferably $R^5$ is methyl or ethyl;
⁎--- stands for the (R)-enantiomer or for the racemate of compound of Formula Ib.

In one embodiment, preferred compounds of Formula Ib are those of Formula Ib':

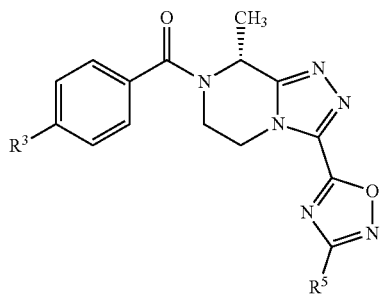

and pharmaceutically acceptable solvates thereof, wherein $R^3$ and $R^5$ are defined as in Formula Ib.

In one embodiment, preferred compounds of Formula Ib are those of Formula Ib":

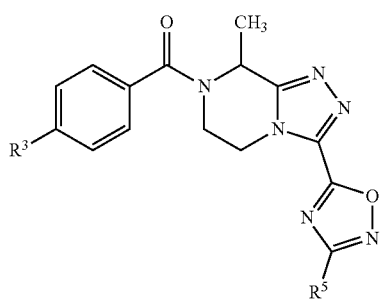

and pharmaceutically acceptable solvates thereof, wherein $R^3$ and $R^5$ are defined as in Formula Ib.

In one embodiment, preferred compounds of Formula Ib are those of Formula Ib-1:

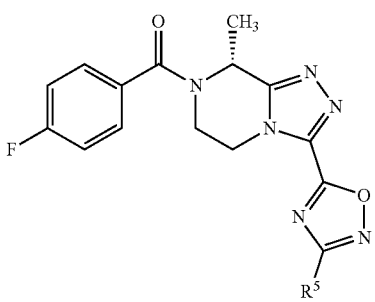

and pharmaceutically acceptable solvates thereof, wherein $R^5$ is methyl, ethyl, trifluoromethyl, difluoromethyl or fluoromethyl, preferably $R^5$ is methyl or ethyl.

In one embodiment, preferred compounds of Formula Ib are those of Formula Ib-2:

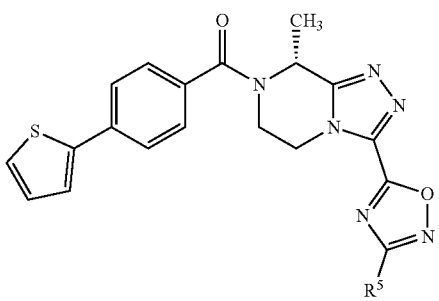

and pharmaceutically acceptable solvates thereof, wherein $R^5$ is ethyl, trifluoromethyl, difluoromethyl or fluoromethyl, preferably $R^5$ is ethyl.

In one embodiment, preferred compounds of Formula I are those of Formula Ic:

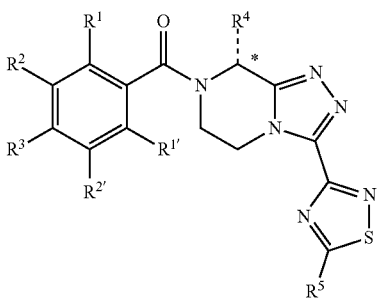

and pharmaceutically acceptable solvates thereof, wherein:
$R^1$ is H, F or methyl;
$R^{1'}$ is H;
$R^2$ is H, F, Cl or methoxy;
$R^{2'}$ is H or F;
$R^3$ is H, F, Cl, methyl, trifluoromethyl or nitrile;
$R^4$ is methyl, ethyl, n-propyl or hydroxyethyl;
$R^5$ is methyl, ethyl or trifluoromethyl;
*--- stands for the (R)-enantiomer or for the racemate.

In one embodiment, preferred compounds of Formula Ic are those of Formula Ic':

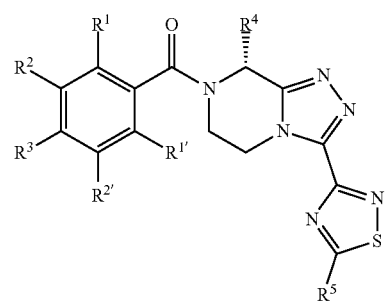

and pharmaceutically acceptable solvates thereof, wherein:
$R^1$ is H, F or methyl, preferably $R^1$ is H;
$R^{1'}$ is H;
$R^2$ is H, F, Cl or methoxy, preferably $R^2$ is H;
$R^{2'}$ is H or F, preferably $R^{2'}$ is H;
$R^3$ is H, F, Cl, methyl, trifluoromethyl or nitrile, preferably $R^3$ is F;
$R^4$ is methyl, ethyl, n-propyl or hydroxyethyl, preferably $R^4$ is methyl;
$R^5$ is methyl, ethyl or trifluoromethyl, preferably $R^5$ is methyl.

Particularly preferred compounds of Formula I of the invention are those listed in Table 1 hereafter.

TABLE 1

| Cpd no | Structure | Chemical name | MW |
|---|---|---|---|
| 1 | 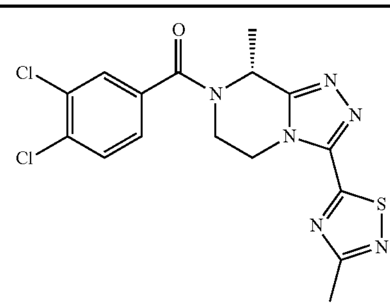 | (R)-(3,4-dichlorophenyl)(8-methyl-3-(3-methyl-1,2,4-thiadiazol-5-yl)-5,6-dihydro-[1,2,4]triazolo[4,3-a]pyrazin-7(8H)-yl)methanone | 409.29 |

TABLE 1-continued

| Cpd no | Structure | Chemical name | MW |
|---|---|---|---|
| 2 | 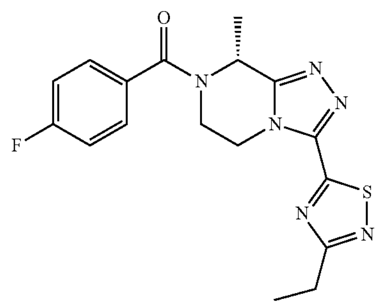 [SMILES: CCc1nsc(-c2nnc3n2CCN(C(=O)c2ccc(F)cc2)[C@@H]3C)n1] | (R)-(3-(3-ethyl-1,2,4-thiadiazol-5-yl)-8-methyl-5,6-dihydro-[1,2,4]triazolo[4,3-a]pyrazin-7(8H)-yl)(4-fluorophenyl)methanone | 372.42 |
| 3 | 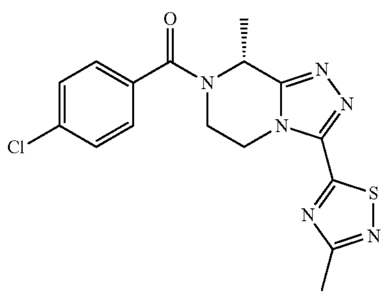 [SMILES: Cc1nsc(-c2nnc3n2CCN(C(=O)c2ccc(Cl)cc2)[C@@H]3C)n1] | (R)-(4-chlorophenyl)(8-methyl-3-(3-methyl-1,2,4-thiadiazol-5-yl)-5,6-dihydro-[1,2,4]triazolo[4,3-a]pyrazin-7(8H)-yl)methanone | 374.85 |
| 4 | 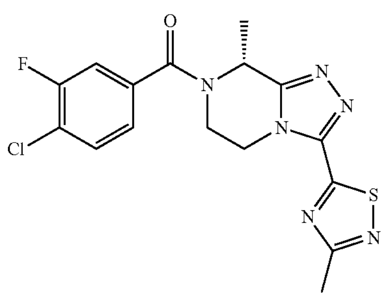 [SMILES: Cc1nsc(-c2nnc3n2CCN(C(=O)c2ccc(Cl)c(F)c2)[C@@H]3C)n1] | (R)-(4-chloro-3-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 392.84 |
| 5 | 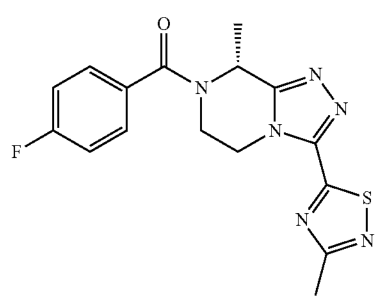 [SMILES: Cc1nsc(-c2nnc3n2CCN(C(=O)c2ccc(F)cc2)[C@@H]3C)n1] | (R)-(4-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 358.39 |
| 6 | 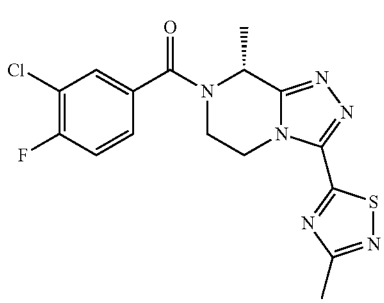 [SMILES: Cc1nsc(-c2nnc3n2CCN(C(=O)c2ccc(F)c(Cl)c2)[C@@H]3C)n1] | (R)-(3-chloro-4-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 392.84 |

TABLE 1-continued

| Cpd no | Structure | Chemical name | MW |
|---|---|---|---|
| 7 | 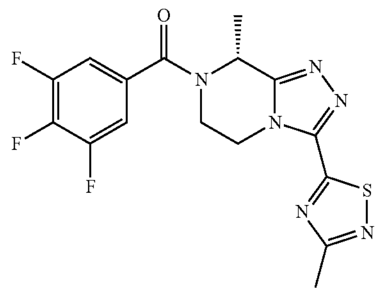 [SMILES: Cc1nsc(-c2nnc3n2CCN(C(=O)c2cc(F)c(F)c(F)c2)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(3,4,5-trifluorophenyl)methanone | 394.37 |
| 8 | 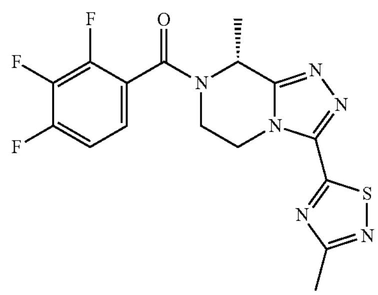 [SMILES: Cc1nsc(-c2nnc3n2CCN(C(=O)c2ccc(F)c(F)c2F)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(2,3,4-trifluorophenyl)methanone | 394.37 |
| 9 | 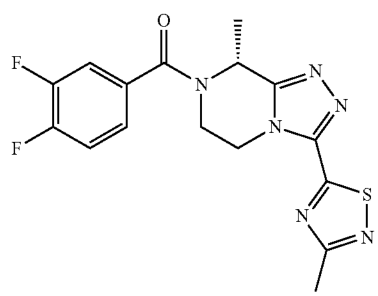 [SMILES: Cc1nsc(-c2nnc3n2CCN(C(=O)c2ccc(F)c(F)c2)[C@@H]3C)n1] | (R)-(3,4-difluorophenyl)(8-methyl-3-(3-methyl-1,2,4-thiadiazol-5-yl)-5,6-dihydro-[1,2,4]triazolo[4,3-a]pyrazin-7(8H)-yl)methanone | 376.38 |
| 10 | 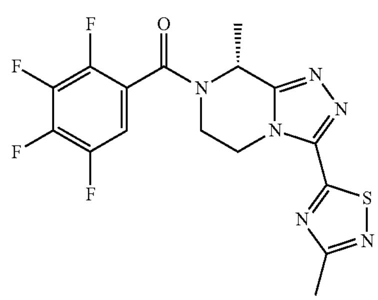 [SMILES: Cc1nsc(-c2nnc3n2CCN(C(=O)c2cc(F)c(F)c(F)c2F)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(2,3,4,5-tetrafluorophenyl)methanone | 412.36 |
| 11 | 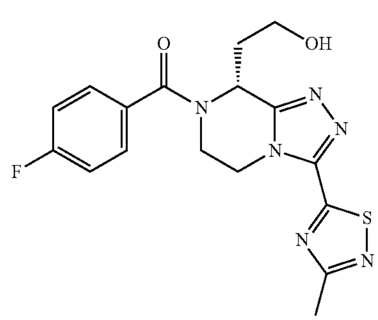 [SMILES: Cc1nsc(-c2nnc3n2CCN(C(=O)c2ccc(F)cc2)[C@@H]3CCO)n1] | (R)-(4-fluorophenyl)(8-(2-hydroxyethyl)-3-(3-methyl-1,2,4-thiadiazol-5-yl)-5,6-dihydro-[1,2,4]triazolo[4,3-a]pyrazin-7(8H)-yl)methanone | 388.42 |

TABLE 1-continued

| Cpd no | Structure | Chemical name | MW |
|---|---|---|---|
| 12 | 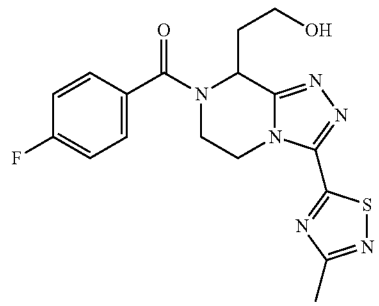 [SMILES: Cc1nsc(-c2nnc3n2CCN(C(=O)c2ccc(F)cc2)C3CCO)n1] | (4-fluorophenyl)(8-(2-hydroxyethyl)-3-(3-methyl-1,2,4-thiadiazol-5-yl)-5,6-dihydro-[1,2,4]triazolo[4,3-a]pyrazin-7(8H)-yl)methanone | 388.42 |
| 13 | 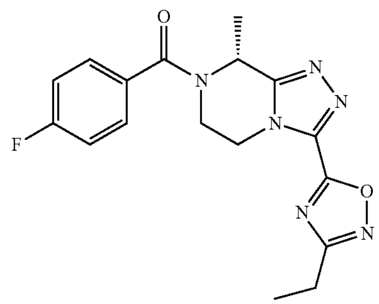 [SMILES: CCc1noc(-c2nnc3n2CCN(C(=O)c2ccc(F)cc2)[C@@H]3C)n1] | (R)-(3-(3-ethyl-1,2,4-oxadiazol-5-yl)-8-methyl-5,6-dihydro-[1,2,4]triazolo[4,3-a]pyrazin-7(8H)-yl)(4-fluorophenyl)methanone | 356.35 |
| 14 | 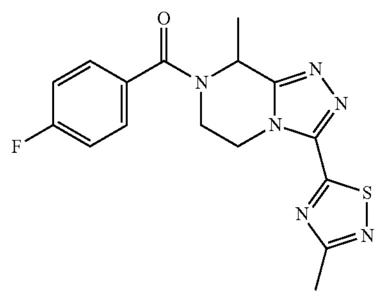 [SMILES: Cc1nsc(-c2nnc3n2CCN(C(=O)c2ccc(F)cc2)C3C)n1] | (4-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 358.39 |
| 15 | 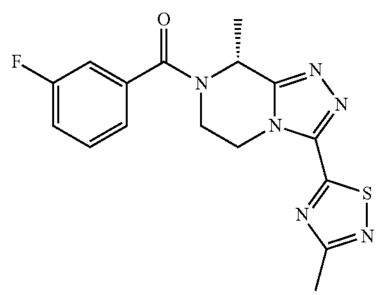 [SMILES: Cc1nsc(-c2nnc3n2CCN(C(=O)c2cccc(F)c2)[C@@H]3C)n1] | (R)-(3-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 358.39 |
| 16 | 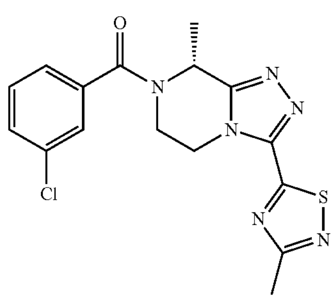 [SMILES: Cc1nsc(-c2nnc3n2CCN(C(=O)c2cccc(Cl)c2)[C@@H]3C)n1] | (R)-(3-chlorophenyl)(8-methyl-3-(3-methyl-1,2,4-thiadiazol-5-yl)-5,6-dihydro-[1,2,4]triazolo[4,3-a]pyrazin-7(8H)-yl)methanone | 374.85 |

TABLE 1-continued

| Cpd no | Structure | Chemical name | MW |
|---|---|---|---|
| 17 | 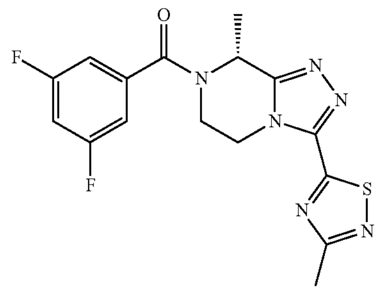 [SMILES: Cc1nsc(-c2nnc3n2CCN(C(=O)c2cc(F)cc(F)c2)[C@@H]3C)n1] | (R)-(3,5-difluorophenyl)(8-methyl-3-(3-methyl-1,2,4-thiadiazol-5-yl)-5,6-dihydro-[1,2,4] triazolo[4,3-a]pyrazin-7(8H)-yl)methanone | 376.38 |
| 18 | 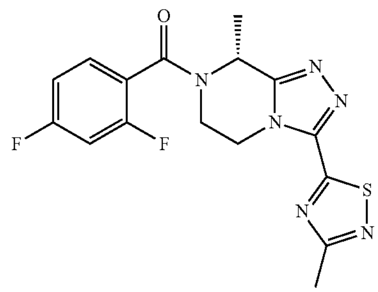 [SMILES: Cc1nsc(-c2nnc3n2CCN(C(=O)c2ccc(F)cc2F)[C@@H]3C)n1] | (R)-(2,4-difluorophenyl)(8-methyl-3-(3-methyl-1,2,4-thiadiazol-5-yl)-5,6-dihydro-[1,2,4]triazolo[4,3-a]pyrazin-7(8H)-yl)methanone | 376.38 |
| 19 | 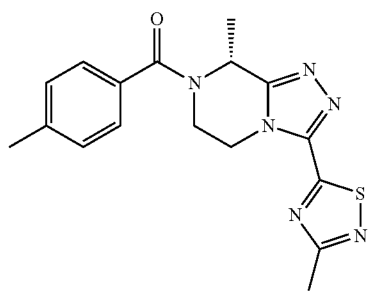 [SMILES: Cc1ccc(C(=O)N2CCn3c(-c4nc(C)ns4)nnc3[C@H]2C)cc1] | (R)-(8-methyl-3-(3-methyl-1,2,4-thiadiazol-5-yl)-5,6-dihydro-[1,2,4]triazolo[4,3-a]pyrazin-7(8H)-yl)(p-tolyl)methanone | 354.43 |
| 20 | 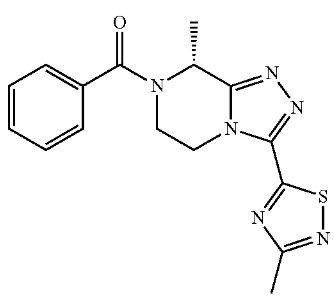 [SMILES: Cc1nsc(-c2nnc3n2CCN(C(=O)c2ccccc2)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(phenyl)methanone | 340.4 |
| 21 | 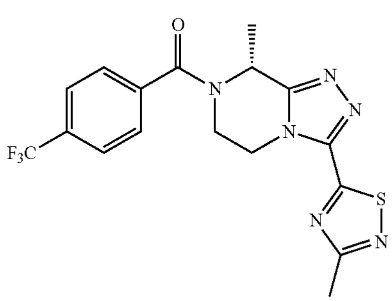 [SMILES: Cc1nsc(-c2nnc3n2CCN(C(=O)c2ccc(C(F)(F)F)cc2)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(4-(trifluoromethyl)phenyl)methanone | 408.4 |

TABLE 1-continued

| Cpd no | Structure | Chemical name | MW |
|---|---|---|---|
| 22 | 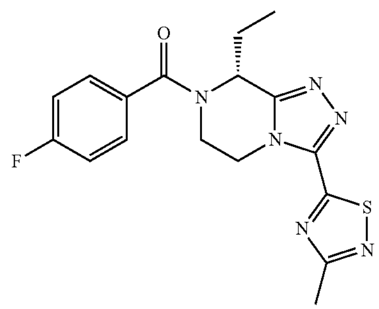 [SMILES: CC[C@@H]1c2nnc(-c3nc(C)ns3)n2CCN1C(=O)c1ccc(F)cc1] | (R)-(8-ethyl-3-(3-methyl-1,2,4-thiadiazol-5-yl)-5,6-dihydro-[1,2,4]triazolo[4,3-a]pyrazin-7(8H)-yl)(4-fluorophenyl)methanone | 372.42 |
| 23 | 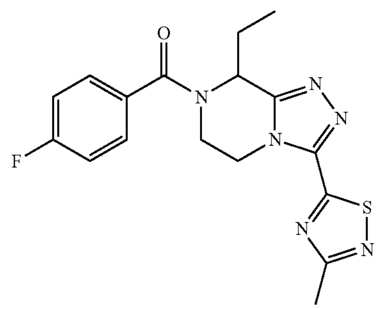 [SMILES: CCC1c2nnc(-c3nc(C)ns3)n2CCN1C(=O)c1ccc(F)cc1] | (8-ethyl-3-(3-methyl-1,2,4-thiadiazol-5-yl)-5,6-dihydro-[1,2,4]triazolo[4,3-a]pyrazin-7(8H)-yl)(4-fluorophenyl)methanone | 372.42 |
| 24 | 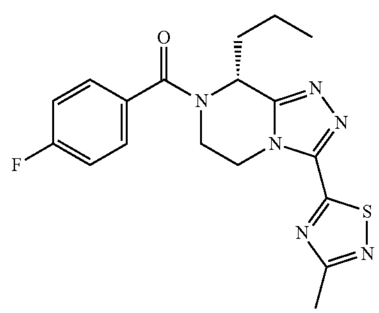 [SMILES: CCC[C@@H]1c2nnc(-c3nc(C)ns3)n2CCN1C(=O)c1ccc(F)cc1] | (R)-(4-fluorophenyl)(3-(3-methyl-1,2,4-thiadiazol-5-yl)-8-propyl-5,6-dihydro-[1,2,4]triazolo[4,3-a]pyrazin-7(8H)-yl)methanone | 386.45 |
| 25 | 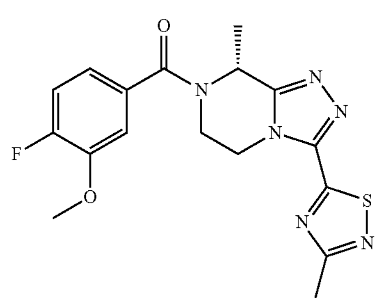 [SMILES: COc1cc(C(=O)N2CCn3c(-c4nc(C)ns4)nnc3[C@H]2C)ccc1F] | (R)-(4-fluoro-3-methoxyphenyl)(8-methyl-3-(3-methyl-1,2,4-thiadiazol-5-yl)-5,6-dihydro-[1,2,4]triazolo[4,3-a]pyrazin-7(8H)-yl)methanone | 388.42 |
| 26 | 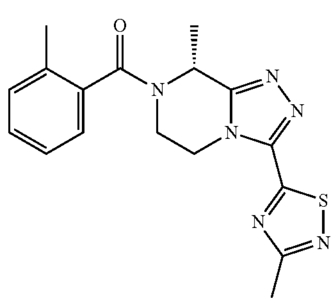 [SMILES: Cc1nsc(-c2nnc3n2CCN(C(=O)c2ccccc2C)[C@@H]3C)n1] | (R)-(8-methyl-3-(3-methyl-1,2,4-thiadiazol-5-yl)-5,6-dihydro-[1,2,4]triazolo[4,3-a]pyrazin-7(8H)-yl)(o-tolyl)methanone | 354.43 |

TABLE 1-continued

| Cpd no | Structure | Chemical name | MW |
|---|---|---|---|
| 27 | 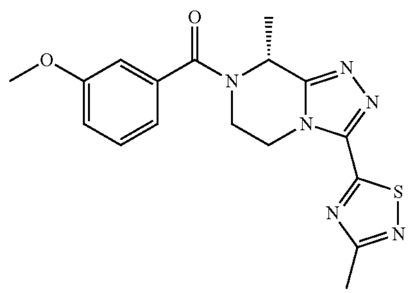 [SMILES: COc1cccc(C(=O)N2CCn3c(-c4nc(C)ns4)nnc3[C@H]2C)c1] | (R)-(3-methoxyphenyl)(8-methyl-3-(3-methyl-1,2,4-thiadiazol-5-yl)-5,6-dihydro-[1,2,4]triazolo[4,3-a]pyrazin-7(8H)-yl)methanone | 370.43 |
| 28 | 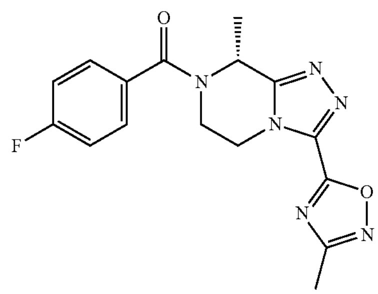 [SMILES: Cc1noc(-c2nnc3n2CCN(C(=O)c2ccc(F)cc2)[C@@H]3C)n1] | (R)-(4-fluorophenyl)(8-methyl-3-(3-methyl-1,2,4-oxadiazol-5-yl)-5,6-dihydro-[1,2,4]triazolo[4,3-a]pyrazin-7(8H)-yl)methanone | 342.33 |
| 29 | 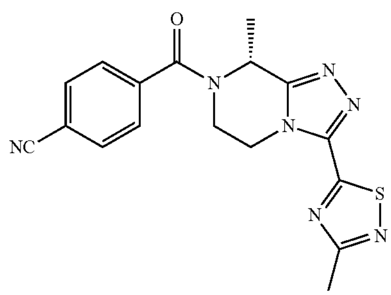 [SMILES: Cc1nsc(-c2nnc3n2CCN(C(=O)c2ccc(C#N)cc2)[C@@H]3C)n1] | (R)-4-(8-methyl-3-(3-methyl-1,2,4-thiadiazol-5-yl)-5,6,7,8-tetrahydro-[1,2,4]triazolo[4,3-a]pyrazine-7-carbonyl)benzonitrile | 365.41 |
| 30 | 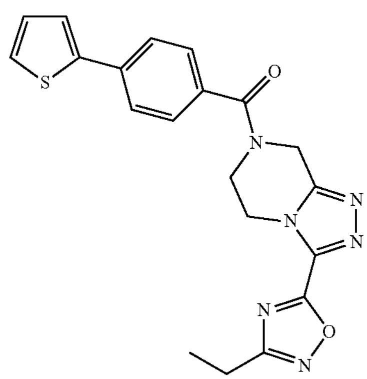 [SMILES: CCc1noc(-c2nnc3n2CCN(C(=O)c2ccc(-c4cccs4)cc2)C3)n1] | (R)-(3-(3-ethyl-1,2,4-oxadiazol-5-yl)-8-methyl-5,6-dihydro-[1,2,4]triazolo[4,3-a]pyrazin-7(8H)-yl)(4-(thiophen-2-yl)phenyl)methanone | 420.49 |
| 31 | 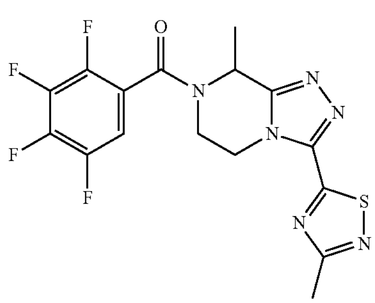 [SMILES: Cc1nsc(-c2nnc3n2CCN(C(=O)c2cc(F)c(F)c(F)c2F)C3C)n1] | (8-methyl-3-(3-methyl-1,2,4-thiadiazol-5-yl)-5,6-dihydro-[1,2,4]triazolo[4,3-a]pyrazin-7(8H)-yl)(2,3,4,5-tetrafluorophenyl)methanone | 412.36 |

TABLE 1-continued

| Cpd no | Structure | Chemical name | MW |
|---|---|---|---|
| 32 | 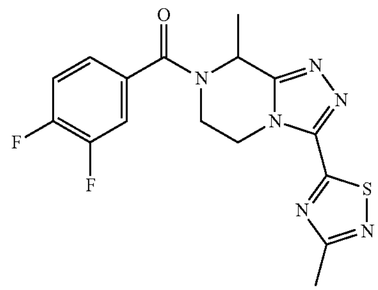 [SMILES: Cc1nsc(-c2nnc3n2CCN(C(=O)c2ccc(F)c(F)c2)C3C)n1] | (3,4-difluorophenyl)(8-methyl-3-(3-methyl-1,2,4-thiadiazol-5-yl)-5,6-dihydro-[1,2,4]triazolo[4,3-a]pyrazin-7(8H)-yl)methanone | 376.38 |
| 33 | 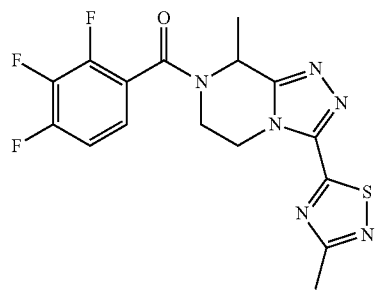 [SMILES: Cc1nsc(-c2nnc3n2CCN(C(=O)c2ccc(F)c(F)c2F)C3C)n1] | (8-methyl-3-(3-methyl-1,2,4-thiadiazol-5-yl)-5,6-dihydro-[1,2,4]triazolo[4,3-a]pyrazin-7(8H)-yl)(2,3,4-trifluorophenyl)methanone | 394.37 |
| 34 | 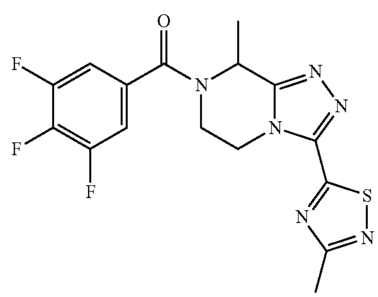 [SMILES: Cc1nsc(-c2nnc3n2CCN(C(=O)c2cc(F)c(F)c(F)c2)C3C)n1] | (8-methyl-3-(3-methyl-1,2,4-thiadiazol-5-yl)-5,6-dihydro-[1,2,4]triazolo[4,3-a]pyrazin-7(8H)-yl)(3,4,5-trifluorophenyl)methanone | 394.37 |
| 35 | 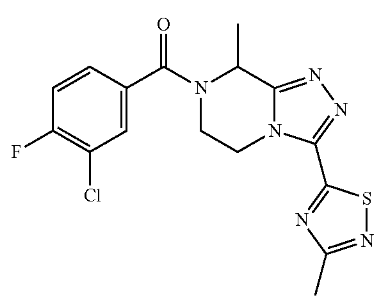 [SMILES: Cc1nsc(-c2nnc3n2CCN(C(=O)c2ccc(F)c(Cl)c2)C3C)n1] | (3-chloro-4-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 392.84 |
| 36 | 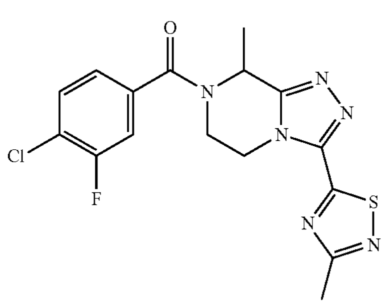 [SMILES: Cc1nsc(-c2nnc3n2CCN(C(=O)c2ccc(Cl)c(F)c2)C3C)n1] | (4-chloro-3-fluorophenyl)(8-methyl-3-(3-methyl-1,2,4-thiadiazol-5-yl)-5,6-dihydro-[1,2,4]triazolo[4,3-a]pyrazin-7(8H)-yl)methanone | 392.84 |

TABLE 1-continued

| Cpd no | Structure | Chemical name | MW |
|---|---|---|---|
| 37 | 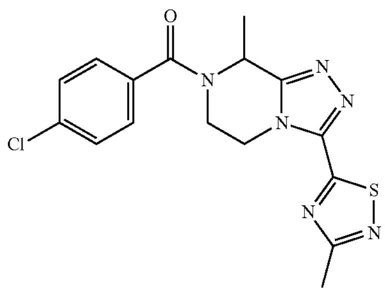 [SMILES: Cc1nsc(-c2nnc3n2CCN(C(=O)c2ccc(Cl)cc2)C3C)n1] | (4-chlorophenyl)(8-methyl-3-(3-methyl-1,2,4-thiadiazol-5-yl)-5,6-dihydro-[1,2,4]triazolo[4,3-a]pyrazin-7(8H)-yl)methanone | 374.85 |
| 38 | 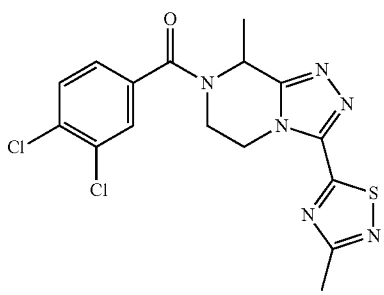 [SMILES: Cc1nsc(-c2nnc3n2CCN(C(=O)c2ccc(Cl)c(Cl)c2)C3C)n1] | (3,4-dichlorophenyl)(8-methyl-3-(3-methyl-1,2,4-thiadiazol-5-yl)-5,6-dihydro-[1,2,4]triazolo[4,3-a]pyrazin-7(8H)-yl)methanone | 409.29 |
| 39 | 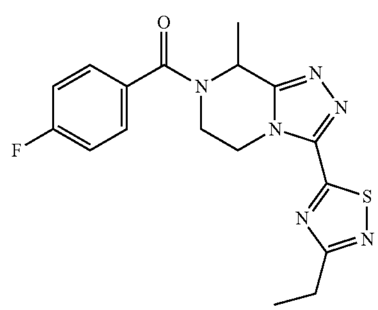 [SMILES: CCc1nsc(-c2nnc3n2CCN(C(=O)c2ccc(F)cc2)C3C)n1] | (3-(3-ethyl-1,2,4-thiadiazol-5-yl)-8-methyl-5,6-dihydro-[1,2,4]triazolo[4,3-a]pyrazin-7(8H)-yl)(4-fluorophenyl)methanone | 372.42 |
| 40 | 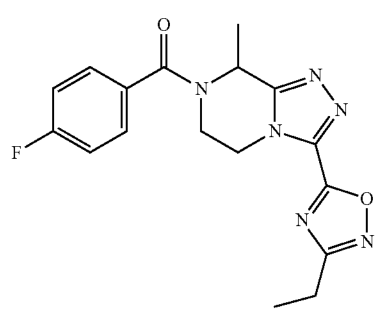 [SMILES: CCc1noc(-c2nnc3n2CCN(C(=O)c2ccc(F)cc2)C3C)n1] | (3-(3-ethyl-1,2,4-oxadiazol-5-yl)-8-methyl-5,6-dihydro-[1,2,4]triazolo[4,3-a]pyrazin-7(8H)-yl)(4-fluorophenyl)methanone | 356.35 |
| 41 | 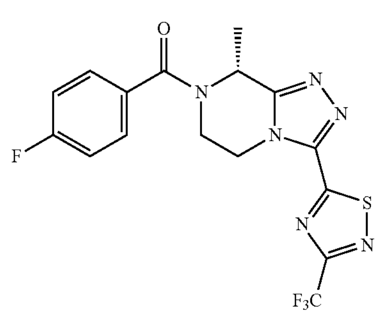 [SMILES: C[C@@H]1c2nnc(-c3nc(C(F)(F)F)ns3)n2CCN1C(=O)c1ccc(F)cc1] | (R)-(4-fluorophenyl)(8-methyl-3-(3-(trifluoromethyl)-1,2,4-thiadiazol-5-yl)-5,6-dihydro-[1,2,4]triazolo[4,3-a]pyrazin-7(8H)-yl)methanone | 412.36 |

TABLE 1-continued

| Cpd no | Structure | Chemical name | MW |
|---|---|---|---|
| 42 | 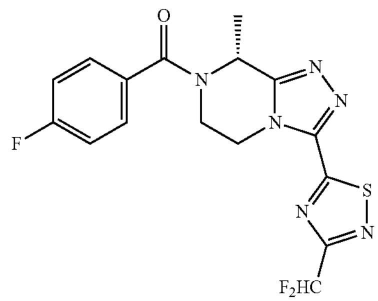 [SMILES: C[C@@H]1c2nnc(-c3nc(C(F)F)ns3)n2CCN1C(=O)c1ccc(F)cc1] | (R)-(3-(3-(difluoromethyl)-1,2,4-thiadiazol-5-yl)-8-methyl-5,6-dihydro-[1,2,4]triazolo[4,3-a]pyrazin-7(8H)-yl)(4-fluorophenyl)methanone | 394.37 |
| 43 | 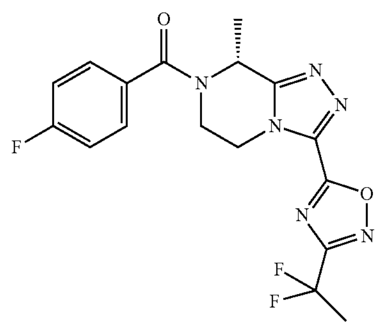 [SMILES: C[C@@H]1c2nnc(-c3nc(C(C)(F)F)no3)n2CCN1C(=O)c1ccc(F)cc1] | (R)-(3-(3-(1,1-difluoroethyl)-1,2,4-oxadiazol-5-yl)-8-methyl-5,6-dihydro-[1,2,4]triazolo[4,3-a]pyrazin-7(8H)-yl)(4-fluorophenyl)methanone | 392.34 |
| 44 | 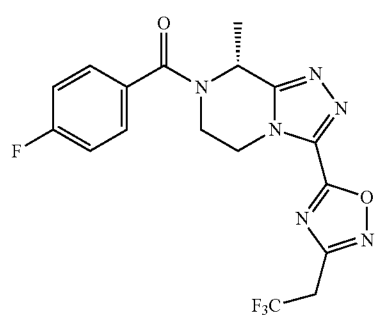 [SMILES: C[C@@H]1c2nnc(-c3nc(CC(F)(F)F)no3)n2CCN1C(=O)c1ccc(F)cc1] | (R)-(4-fluorophenyl)(8-methyl-3-(3-(2,2,2-trifluoroethyl)-1,2,4-oxadiazol-5-yl)-5,6-dihydro-[1,2,4]triazolo[4,3-a]pyrazin-7(8H)-yl)methanone | 410.33 |
| 45 | | ((8R)-3-(3-(1-fluoroethyl)-1,2,4-oxadiazol-5-yl)-8-methyl-5,6-dihydro-[1,2,4]triazolo[4,3-a]pyrazin-7(8H)-yl)(4-fluorophenyl)methanone | 374.34 | and pharmaceutically acceptable solvates thereof.

In Table 1, the term "Cpd" means compound.

The compounds of Table 1 were named using ChemBioDraw® Ultra version 12.0 (PerkinElmer).

The compounds of Formula I can be prepared by different ways with reactions known to a person skilled in the art.

The invention further relates to a process of manufacturing of compounds of Formula I:

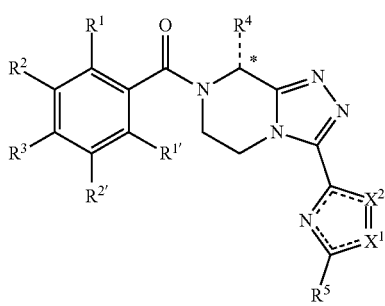

and pharmaceutically acceptable solvates thereof, wherein:
$R^1$ is H, F or methyl;
$R^{1'}$ is H;
$R^2$ is H, F, Cl or methoxy;
$R^{2'}$ is H or F;
$R^3$ is H, F, Cl, methyl, trifluoromethyl, nitrile or $R^3$ is thiophen-2-yl under the condition that $R^5$ is not methyl;
$R^4$ is methyl, ethyl, n-propyl, hydroxyethyl, methoxyethyl, trifluoromethyl, difluoromethyl or fluoromethyl, preferably $R^4$ is methyl, ethyl, n-propyl or hydroxyethyl;
$R^5$ is methyl, ethyl, methoxymethyl, trifluoromethyl, difluoromethyl, fluoromethyl, 1-fluoroethyl, 1,1-difluoroethyl or 2,2,2-trifluoroethyl, preferably $R^5$ is methyl, ethyl, methoxymethyl, trifluoromethyl, difluoromethyl or fluoromethyl, preferably $R^5$ is methyl, ethyl or trifluoromethyl;
$X^1$ is N and $X^2$ is S or O; or $X^1$ is S and $X^2$ is N, preferably $X^1$ is N and $X^2$ is S or O, more preferably, $X^1$ is N and $X^2$ is S;
represents a single or a double bound depending on $X^1$ and $X^2$;
$\overset{*}{\text{---}}$ stands for the (R)-enantiomer or for the racemate of compound of Formula I; characterized in that it comprises the following steps:
a) reacting a compound of Formula (i)

(i)

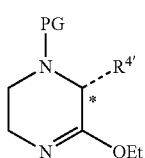

wherein:
PG represents a suitable protecting group such as for example DMB, PMB, Boc, allyl, diphenyl-phosphiramide (DPP), 2-trimethylsilylethanesulfonyl (SES), preferably PG is DMB;
$R^{4'}$ is $R^4$ as defined above or a reducible precursor of hydroxyethyl and consequently a further precursor of methoxyethyl, such as for example —$CH_2CO_2Alkyl$; where the term "reducible precursor of hydroxyethyl or consequently a further precursor of methoxyethyl" refers to any chemical group which, when reacting with reducing agents, such as for example $LiAlH_4$, is reduced to hydroxyethyl and then optionally further converted to methoxyethyl;

$\overset{*}{\text{---}}$ stands for the (R)-enantiomer or for the racemate;
with a compound of Formula (ii)

(ii)

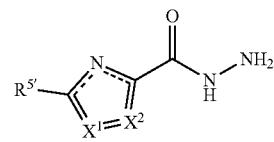

wherein:
$R^{5'}$ is $R^5$ as defined above, H or 1-((tert-butyldiphenylsilyl)oxy)ethyl, preferably $R^{5'}$ is $R^5$ as defined above or H;
$X^1$ and $X^2$ are as defined above; and represents a single or a double bound depending on $X^1$ and $X^2$; so as to obtain a compound of Formula (iii)

(iii)

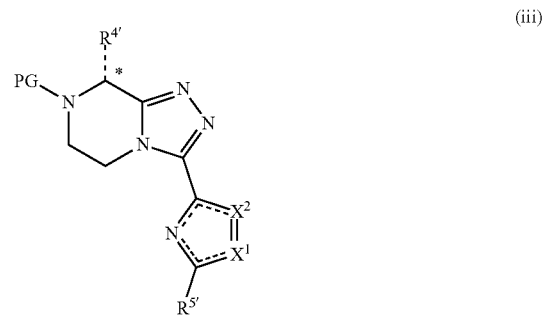

wherein PG, $R^{4'}$, $R^{5'}$, $X^1$ and $X^2$ are as defined above, stands for the (R)-enantiomer or for the racemate and represents a single or a double bound depending on $X^1$ and $X^2$; b) deprotecting compound of Formula (iii) with a suitable deprotection agent to afford compound of Formula (iv)

(iv)

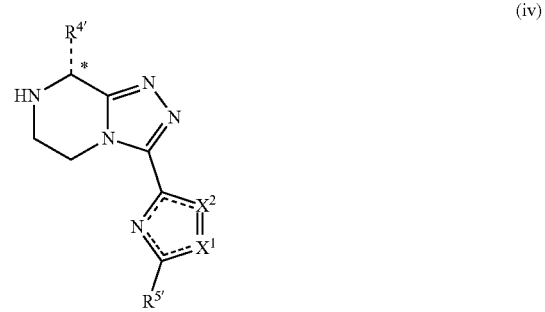

wherein $R^{4'}$, $R^{5'}$, $X^1$ and $X^2$ are as defined above, stands for the (R)-enantiomer or for the racemate and represents a single or a double bound depending on $X^1$ and $X^2$;
c) when $R^{5'}$ is H, introducing a trifluoromethyl or difluoromethyl group by direct C—H trifluoro- or difluoromethylation, leading to compound of Formula (v)

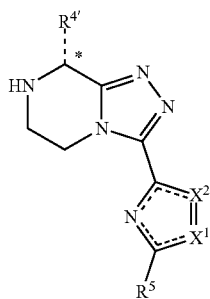

(v)

wherein $R^{4'}$, $X^1$ and $X^2$ are as defined above and $R^5$ is trifluoromethyl or difluoromethyl, stands for the (R)-enantiomer or for the racemate and represents a single or a double bound depending on $X^1$ and $X^2$;

d) N-acylating compound of Formula (iv) wherein $R^{5'}$ is not H or compound of Formula (v), with a compound of Formula (vi)

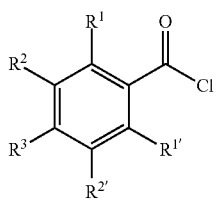

(vi)

wherein $R^1$, $R^{1'}$, $R^2$, $R^{2'}$ and $R^3$ are as defined above; leading to compound of Formula (vii)

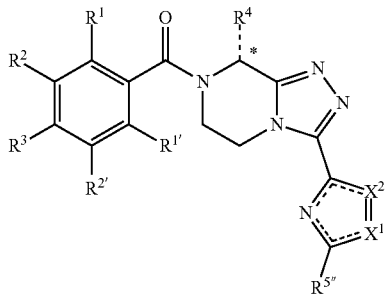

wherein $R^1$, $R^{1'}$, $R^2$, $R^{2'}$, $R^3$, $R^{4'}$, $X^1$ and $X^2$ are as defined above, stands for the (R)-enantiomer or for the racemate, represents a single or a double bound depending on $X^1$ and $X^2$; and $R^{5''}$ is $R^5$ as defined in Formula I or 1-((tert-butyldiphenylsilyl)oxy)ethyl;

e) optionally further conducting one or both of the two following steps:

e') when $R^{4'}$ is a reducible precursor of hydroxyethyl and consequently a further precursor of methoxyethyl, a step of reduction optionally followed by methyl ether formation;

e'') when $R^{5''}$ is 1-((tert-butyldiphenylsilyl)oxy)ethyl, a step of alcohol deprotection and subsequent fluorination to form 1-fluoroethyl $R^5$ group; or a step of alcohol deprotection, followed by an oxidation step and a subsequent fluorination step to afford 1,1-difluoroethyl $R^5$ group;

to afford compound of Formula I.

In a preferred embodiment, the protecting group PG used in the process of the invention is DMB.

According to one embodiment, the introduction of a trifluoromethyl or difluoromethyl group at step c) may be performed by direct C—H trifluoro- or difluoromethylation as described by Ji Y. et al. in PNAS, 2011, 108(35), 14411-14415 or by Fujiwara Y. et al. in JACS, 2012, 134, 1494-1497.

According to one embodiment, the fluorination step to form 1-fluoroethyl or 1,1-difluoroethyl $R^5$ groups at step e'') may be performed by DAST fluorination. DAST fluorination may be performed as described in WO2004/103953, page 51.

Reaction schemes as described in the example section are illustrative only and should not be construed as limiting the invention in any way. According to one embodiment, compounds of Formula I can be prepared using the chiral synthesis of the invention detailed in the examples below.

The invention is further directed to the use of the compounds of the invention or pharmaceutically acceptable solvates thereof as antagonists to the NK-3 receptor.

Accordingly, in a particularly preferred embodiment, the invention relates to the use of compounds of Formula I and subformulae in particular those of Table 1 above, or pharmaceutically acceptable solvates thereof, as NK-3 receptor antagonists.

Accordingly, in another aspect, the invention relates to the use of these compounds or solvates thereof for the synthesis of pharmaceutical active ingredients, such as selective NK-3 receptor antagonists.

Uses

The compounds of the invention are therefore useful as medicaments, in particular in the prevention and/or treatment of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis. The compounds of the invention are therefore useful as medicaments, in particular in the prevention and/or treatment of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, urinary incontinence, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis.

The invention also provides for a method for delaying in patient the onset of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis comprising the administration of a pharmaceutically effective amount of a compound of Formula I or pharmaceutically acceptable solvate thereof to a patient in need thereof. The invention also provides for a method for delaying in patient the onset of depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, urinary incontinence, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis comprising the administration of a pharmaceutically effective amount of a compound of Formula I or pharmaceutically acceptable solvate thereof to a patient in need thereof.

Preferably, the patient is a warm-blooded animal, more preferably a human.

The compounds of the invention are especially useful in the treatment and/or prevention of sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis. The compounds of the invention are especially useful in the treatment and/or prevention of sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis.

In a specific embodiment, the compounds of the invention are especially useful in the treatment and/or prevention of benign prostatic hyperplasia (BPH), endometriosis, uterine fibrosis, uterine fibroid tumor, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis. In a specific embodiment, the compounds of the invention are especially useful in the treatment and/or prevention of benign prostatic hyperplasia (BPH), endometriosis, uterine fibrosis, uterine fibroid tumor, uterine leiomyoma, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis.

In a specific embodiment, the compounds of the invention are especially useful in the treatment and/or prevention of endometriosis, uterine fibrosis, uterine fibroid tumor, uterine leiomyoma, polycystic ovary syndrome (PCOS) and benign prostatic hyperplasia (BPH).

In a specific embodiment, the compounds of the invention are especially useful in the treatment and/or prevention of endometriosis.

In a specific embodiment, the compounds of the invention are especially useful in the treatment and/or prevention of uterine fibrosis.

In a specific embodiment, the compounds of the invention are especially useful in the treatment and/or prevention of uterine fibroid tumor.

In a specific embodiment, the compounds of the invention are especially useful in the treatment and/or prevention of uterine leiomyoma.

In a specific embodiment, the compounds of the invention are especially useful in the treatment and/or prevention of polycystic ovary syndrome (PCOS).

In a specific embodiment, the compounds of the invention are especially useful in the treatment and/or prevention of benign prostatic hyperplasia (BPH).

In a specific embodiment, the compounds of the invention are especially useful in the treatment and/or prevention of hot flashes also known as hot flushes.

In a specific embodiment, the compounds of the invention are especially useful in the treatment and/or prevention of peri-menopausal conditions (i.e. 'hot flashes'), in vitro fertilization ('IVF'), male contraceptive, female contraceptive, castration of sex offenders.

In a specific embodiment, the compounds of the invention are especially useful in the treatment and/or prevention of hot flashes related to peri-menopausal conditions, menopausal conditions and/or postmenopausal conditions.

In a specific embodiment, the compounds of the invention are especially useful in the treatment and/or prevention of hot flashes which are a consequence of hormone therapy intentionally lowering the level of sex hormones, such as for example therapy-induced hot flashes in breast, uterine or prostate cancers.

The compounds of the invention are also useful in the treatment of gynecological disorders and infertility. In particular, the invention provides methods to lower and/or suppress the LH-surge in assisted conception.

The compounds of the invention are also useful to cause male castration and to inhibit the sex drive in men. This is of particular interest in the treatment of male sexual offenders.

The invention further provides the use of a compound of Formula I or a pharmaceutically acceptable solvate thereof for the manufacture of a medicament for treating and/or preventing depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis in a patient. The invention further provides the use of a compound of Formula I or a pharmaceutically acceptable solvate thereof for the manufacture of a medicament for treating and/or preventing depression, anxiety, psychosis, schizophrenia, psychotic disorders, bipolar disorders, cognitive disorders, Parkinson's disease, Alzheimer's disease, attention deficit hyperactivity disorder (ADHD), pain, convulsion, obesity, inflammatory diseases including irritable bowel syndrome (IBS) and inflammatory bowel disorders, emesis, pre-eclampsia, airway related diseases including chronic obstructive pulmonary disease, asthma, airway hyperresponsiveness, bronchoconstriction and cough, urinary incontinence, reproduction disorders, contraception and sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis in a patient.

Preferably, the patient is a warm-blooded animal, more preferably a human.

The invention especially provides the use of a compound of Formula I or a pharmaceutically acceptable solvate thereof for the manufacture of a medicament to treat and/or prevent sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis. The invention especially provides the use of a compound of Formula I or a pharmaceutically acceptable solvate thereof for the manufacture of a medicament to treat and/or prevent sex hormone-dependent diseases including but not limited to benign prostatic hyperplasia (BPH), prostatic hyperplasia, metastatic prostatic carcinoma, testicular cancer, breast cancer, ovarian cancer, androgen dependent acne, male pattern baldness, endometriosis, abnormal puberty, uterine fibrosis, uterine fibroid tumor, uterine leiomyoma, hormone-dependent cancers, hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), androgen-producing tumor (virilizing ovarian or adrenal tumor), menorrhagia and adenomyosis.

In a specific embodiment, compounds of Formula I or a pharmaceutically acceptable solvate thereof may be used for the manufacture of a medicament to treat and/or prevent endometriosis, uterine fibrosis, uterine fibroid tumor, uterine leiomyoma, polycystic ovary syndrome (PCOS) and benign prostatic hyperplasia (BPH).

In a specific embodiment, compounds of Formula I or a pharmaceutically acceptable solvate thereof may be used for the manufacture of a medicament to treat and/or prevent endometriosis.

In a specific embodiment, compounds of Formula I or a pharmaceutically acceptable solvate thereof may be used for the manufacture of a medicament to treat and/or prevent uterine fibrosis.

In a specific embodiment, compounds of Formula I or a pharmaceutically acceptable solvate thereof may be used for the manufacture of a medicament to treat and/or prevent uterine fibroid tumor.

In a specific embodiment, compounds of Formula I or a pharmaceutically acceptable solvate thereof may be used for the manufacture of a medicament to treat and/or prevent uterine leiomyoma.

In a specific embodiment, compounds of Formula I or a pharmaceutically acceptable solvate thereof may be used for the manufacture of a medicament to treat and/or prevent polycystic ovary syndrome (PCOS).

In a specific embodiment, compounds of Formula I or a pharmaceutically acceptable solvate thereof may be used for the manufacture of a medicament to treat and/or prevent benign prostatic hyperplasia (BPH).

In a specific embodiment, compounds of Formula I or a pharmaceutically acceptable solvate thereof may be used for the manufacture of a medicament to treat and/or prevent hot flashes also known as hot flushes.

The invention further provides the use of a compound of Formula I or a pharmaceutically acceptable solvate thereof for the manufacture of a medicament to lower and/or suppress the LH-surge in assisted conception in a patient. Preferably the patient is a warm-blooded animal, more preferably a woman.

The invention further provides the use of a compound of Formula I or a pharmaceutically acceptable solvate thereof for the manufacture of a medicament to cause male castration and to inhibit the sex drive in men. This is of particular interest in the treatment of male sexual offenders.

According to a further feature of the present invention there is provided a method for modulating NK-3 receptor activity, in a patient, preferably a warm blooded animal, and even more preferably a human, in need of such treatment, which comprises administering to said patient an effective amount of compound of the present invention, or a pharmaceutically acceptable solvate thereof.

According to one embodiment, the compounds of the invention, their pharmaceutical acceptable solvates may be administered as part of a combination therapy. Thus, are included within the scope of the present invention embodiments comprising coadministration of, and compositions and medicaments which contain, in addition to a compound of the present invention, a pharmaceutically acceptable solvate thereof as active ingredient, additional therapeutic agents and/or active ingredients. Such multiple drug regimens, often referred to as "combination therapy", may be used in the treatment and/or prevention of any of the diseases or conditions mediated by or associated with NK-3 receptor modulation. The use of such combinations of therapeutic agents is especially pertinent with respect to the treatment of the above-mentioned disorders within a patient in need of treatment or one at risk of becoming such a patient.

In addition to the requirement of therapeutic efficacy, which may necessitate the use of active agents in addition to the NK-3 receptor modulator compounds of Formula I or pharmaceutical acceptable solvates thereof, there may be additional rationales which compel or highly recommend the use of combinations of drugs involving active ingredients which represent adjunct therapy, i.e., which complement and supplement the function performed by the NK-3 receptor modulator compounds of the present invention. Suitable supplementary therapeutic agents used for the purpose of auxiliary treatment include drugs which, instead of directly treating or preventing a disease or condition mediated by or associated with NK-3 receptor modulation, treat diseases or conditions which directly result from or indirectly accompany the basic or underlying NK-3 receptor modulated disease or condition.

According to a further feature of the present invention, the compound of Formula I, a pharmaceutically acceptable solvate thereof may be used in combination therapy with antipsychotic drugs (APD), to improve the efficacy and to minimize secondary effects associated to APD including but not limited to Dopamine 2/3 and 5-HT2 receptors antagonists. More particular the compound of Formula I, a pharmaceutically acceptable solvate thereof may be used as an adjunct therapy in combination with an atypical antipsychotic drug, including but not limited to risperidone, clozapine, olanzapine, where the NK-3 receptor modulator may serve a role as dose-limiting for the atypical antipsychotic and therefore spare the patient from some of the side effect of those atypical antipsychotic drugs.

Thus, the methods of treatment and pharmaceutical compositions of the present invention may employ the compounds of Formula I or pharmaceutical acceptable solvates thereof in the form of monotherapy, but said methods and compositions may also be used in the form of multiple therapy in which one or more compounds of Formula I or their pharmaceutically acceptable solvates are coadministered in combination with one or more other therapeutic agents.

In the above-described embodiment combinations of the present invention, the compound of Formula I, a pharmaceutically acceptable solvate thereof and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

The invention also provides pharmaceutical compositions comprising a compound of Formula I or a pharmaceutically acceptable solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable solvate thereof as active ingredient, additional therapeutic agents and/or active ingredients.

Another object of this invention is a medicament comprising at least one compound of the invention, or a pharmaceutically acceptable solvate thereof, as active ingredient.

According to a further feature of the present invention there is provided the use of a compound of Formula I or a pharmaceutically acceptable solvate thereof for the manufacture of a medicament for modulating NK-3 receptor activity in a patient, in need of such treatment, which comprises administering to said patient an effective amount of compound of the present invention, or a pharmaceutically acceptable solvate thereof.

Preferably, the patient is a warm-blooded animal, more preferably a human.

As set forth above, the compounds of the invention, their pharmaceutically acceptable solvates may be used in monotherapy or in combination therapy. Thus, according to one embodiment, the invention provides the use of a compound of the invention for the manufacture of a medicament for at least one of the purposes described above, wherein said medicament is administered to a patient in need thereof, preferably a warm-blooded animal, and even more preferably a human, in combination with at least one additional therapeutic agent and/or active ingredient. The benefits and advantages of such a multiple drug regimen, possible administration regimens as well as suitable additional therapeutic agents and/or active ingredients are those described above.

Generally, for pharmaceutical use, the compounds of the invention may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 0.05 and 1000 mg, and usually between 1 and 500 mg, preferably between 2 and 150 mg of at least one compound of the invention, e.g. about 2, 4, 8, 16, 32, 64 or 128 mg per unit dosage. According to another embodiment, such unit dosages will contain between 0.05 and 1000 mg, and usually between 1 and 500 mg, preferably between 2 and 400 mg, preferably between 2 and 200 mg of at least one compound of the invention per unit dosage.

Usually, depending on the condition to be prevented or treated and the route of administration, the active compound of the invention will usually be administered between 0.001 and 10 mg per kilogram body weight, more often between 0.01 and 4 mg per kilogram body weight, preferably between 0.02 and 1.5 mg per kilogram body weight, for example about 0.02, 0.04, 0.08, 0.16, 0.32, 0.64 or 1.28 mg, per kilogram body weight of the patient per day, which may be administered as a single daily dose, divided over one or more daily doses, or essentially continuously, e.g. using a drip infusion. According to another embodiment, the active compound of the invention will usually be administered between 0.001 and 10 mg per kilogram body weight, more often between 0.01 and 7 mg per kilogram body weight, preferably between 0.03 and 3.5 mg per kilogram body weight of the patient per day, which may be administered as a single daily dose, divided over one or more daily doses, or essentially continuously, e.g. using a drip infusion.

According to one embodiment, the active compound of the invention will be administered as a single daily dose, divided over one, two or more daily doses, or essentially continuously, e.g. using a drip infusion.

Definitions

The definitions and explanations below are for the terms as used throughout the entire application, including both the specification and the claims.

When describing the compounds of the invention, the terms used are to be construed in accordance with the following definitions, unless indicated otherwise.

The term "alkyl" refers to a hydrocarbyl radical of formula $C_nH_{2n+1}$ wherein n is a number greater than or equal to 1. Generally, alkyl groups of this invention comprise from 1 to 4 carbon atoms, preferably from 1 to 3 carbon atoms. Alkyl groups may be linear or branched. Suitable alkyl groups include but are not limited to methyl, ethyl, n-propyl, i-propyl, n-butyl, i-butyl, s-butyl and t-butyl.

The term "thiophen-2-yl" as used herein means a group of formula

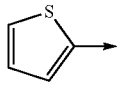

wherein the arrow defines the attachment point.

The ring atoms of (3-substituted)-(8-substituted)-5,6-dihydro-[1,2,4]triazolo[4,3-a]pyrazines of the invention are numbered based on scheme below.

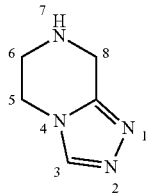

Bonds from an asymmetric carbon in compounds are generally depicted using a solid line (-), a solid wedge

, or a dotted wedge

.

The use of either a solid or dotted wedge to depict bonds from an asymmetric carbon atom is meant to indicate that only the stereoisomer shown is meant to be included.

The compounds of Formula I and subformulae thereof contain a stereogenic carbon center at position 8 and thus may exist as (R)- and (S)-enantiomers. In an embodiment of the invention, compounds of Formula I are not pure (S)-enantiomers relative to the C8 position.

In the compounds of the invention, a dotted wedge

carrying a substituent at the C8 position is used to depict the (R)-enantiomer, thus excluding racemic mixtures thereof.

In the compounds of the invention, a dotted line with a star next to the C8 position (*---) is used to depict either a dotted wedge

to represent the (R)-enantiomer or a solid line (-) to depict the racemic mixture of (R)- and (S)-enantiomer, which is called "racemate".

For instance, (R)-(3,4-dichlorophenyl)(8-methyl-3-(3-methyl-1,2,4-thiadiazol-5-yl)-5,6-dihydro-[1,2,4]triazolo[4,3-a]pyrazin-7(8H)-yl)methanone (compound no 1) is depicted as:

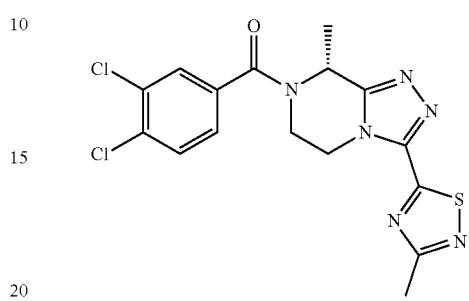

The racemic mixture of this compound, (3,4-dichlorophenyl)(8-methyl-3-(3-methyl-1,2,4-thiadiazol-5-yl)-5,6-dihydro-[1,2,4]triazolo[4,3-a]pyrazin-7(8H)-yl)methanone (compound no 38) is depicted as:

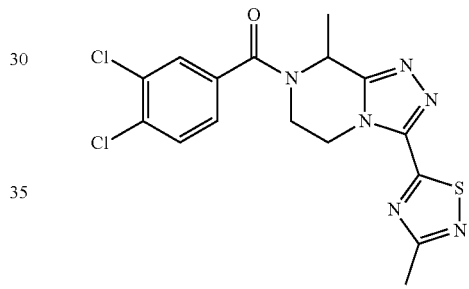

The term "solvate" is used herein to describe a compound in this invention that contains stoichiometric or sub-stoichiometric amounts of one or more pharmaceutically acceptable solvent molecule such as ethanol. The term "hydrate" refers to when the said solvent is water.

All references to compounds of Formula I include references to solvates, multi-component complexes and liquid crystals thereof.

The compounds of the invention include compounds of Formula I as hereinbefore defined, including all polymorphs and crystal habits thereof, prodrugs and prodrugs thereof and isotopically-labeled compounds of Formula I.

The invention also generally covers all pharmaceutically acceptable predrugs and prodrugs of the compounds of Formula I.

The term "prodrug" as used herein means the pharmacologically acceptable derivatives of compounds of Formula I, such as for example esters, whose in vivo biotransformation product generates the biologically active drug. Prodrugs are generally characterized by increased bio-availability and are readily metabolized into biologically active compounds in vivo.

The term "predrug", as used herein, means any compound that will be modified to form a drug species, wherein the modification may take place either inside or outside of the body, and either before or after the predrug reaches the area of the body where administration of the drug is indicated.

The term "patient" refers to a warm-blooded animal, more preferably a human, who/which is awaiting the receipt of, or is receiving medical care or is/will be the object of a medical procedure.

The term "human" refers to a subject of both genders and at any stage of development (i.e. neonate, infant, juvenile, adolescent, adult).

The terms "treat", "treating" and "treatment, as used herein, are meant to include alleviating, attenuating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient (e.g. NK-3 antagonist) that is sufficient to achieve the desired therapeutic or prophylactic effect in the patient to which/whom it is administered.

The term "administration", or a variant thereof (e.g. "administering"), means providing the active agent or active ingredient (e.g. a NK-3 antagonist), alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "antagonist" as used herein means a compound that competitively or non-competitively binds to a receptor at the same site as an agonist (for example, the endogenous ligand) and has reversible and competitive binding affinity to a receptor without direct modulation of receptor signaling, but that nonetheless occupies the binding site of an agonist (for example, the endogenous ligand) to thereby block agonist-mediated receptor signaling.

The term "sex hormone-dependent disease" as used herein means a disease which is exacerbated by, or caused by, excessive, inappropriate or unregulated sex hormone production and/or an extraordinary physiological response to sex hormones. Examples of such diseases in men include but are not limited to benign prostatic hyperplasia (BPH), prostatic hyperplasia, metastatic prostatic carcinoma, testicular cancer, androgen dependent acne, male pattern baldness and precocious puberty in boys. Examples of such diseases in women include but are not limited to endometriosis, abnormal puberty, uterine fibrosis, uterine fibroid tumor, uterine leiomyoma, hormone-dependent cancers (ovarian cancer, breast cancer), androgen-producing tumor (virilizing ovarian or adrenal tumor), hyperandrogenism, hirsutism, virilization, polycystic ovary syndrome (PCOS), premenstrual dysphoric disease (PMDD), HAIR-AN syndrome (hyperandrogenism, insulin resistance and acanthosis nigricans), ovarian hyperthecosis (HAIR-AN with hyperplasia of luteinized theca cells in ovarian stroma), other manifestations of high intraovarian androgen concentrations (e.g. follicular maturation arrest, atresia, anovulation, dysmenorrhea, dysfunctional uterine bleeding, infertility), menorrhagia and adenomyosis (abnormal endometrial growth within the muscle of the uterus).

The term "Psychotic disorders" as used herein means a group of illnesses that affect the mind. These illnesses alter a patient's ability to think clearly, make good judgments, respond emotionally, communicate effectively, understand reality, and behave appropriately. When symptoms are severe, patient with psychotic disorders have difficulty staying in touch with reality and are often unable to meet the ordinary demands of daily life. Psychotic disorders include but are not limited to, schizophrenia, schizophreniform disorder, schizo-affective disorder, delusional disorder, brief psychotic disorder, shared psychotic disorder, psychotic disorder due to a general medical condition, substance-induced psychotic disorder or psychotic disorders not otherwise specified (Diagnostic and Statistical Manual of Mental Disorders, Ed. 4th, American Psychiatric Association, Washington, D.C. 1994).

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

The present invention will be better understood with reference to the following examples. These examples are intended to representative of specific embodiments of the invention, and are not intended as limiting the scope of the invention.

EXAMPLES

Chemistry Examples

All reported temperatures are expressed in degrees Celsius (° C.); all reactions were carried out at room temperature (RT) unless otherwise stated.

All reactions were followed by thin layer chromatography (TLC) analysis (TLC plates, silica gel 60 $F_{254}$, Merck) was used to monitor reactions, establish silica-gel flash chromatography conditions. All other TLC developing agents/visualization techniques, experimental set-up or purification procedures that were used in this invention, when not described in specific details, are assumed to be known to those conversant in the art and are described in such standard reference manuals as: i) Gordon, A. J.; Ford, R. A. "The Chemist's Companion—A Handbook of Practical Data, Techniques, and References", Wiley: New York, 1972; ii) Vogel's Textbook of Practical Organic Chemistry, Pearson Prentice Hall: London, 1989.

HPLC-MS spectra were typically obtained on an Agilent LCMS using electrospray ionization (ESI). The Agilent instrument includes an autosampler 1100, a binary pump 1100, an ultraviolet multi-wavelength detector 1100 and a 6100 single-quad mass-spectrometer. The chromatography column used was Sunfire 3.5 μm, C18, 3.0×50 mm in dimensions.

Eluent typically used was a mixture of solution A (0.1% TFA in $H_2O$) and solution B (0.1% TFA in MeCN).

Gradient was applied at a flow rate of 1.3 mL per minute as follows: gradient A (for analysis of final compounds and intermediates): held the initial conditions of 5% solution B for 0.2 min, increased linearly to 95% solution B in 6 min, held at 95% during 1.75 min, returned to initial conditions in 0.25 min and maintained for 2.0 min; gradient B (for analysis of crude samples and reactions mixtures): held the initial conditions of 5% solution B for 0.2 min, increased linearly to 95% in 2.0 min, held at 95% during 1.75 min, returned to initial conditions in 0.25 min and maintained for 2 min.

Determination of chiral purity was made using chiral HPLC that was performed on an Agilent 1100 (binary pump and a ultraviolet multi wavelength detector) with manual or automatic (Autosampler 1100) injection capabilities. Column used is CHIRALPAK IA 5 µm, 4.6×250 mm 4.6×250 mm in isocratic mode. Choice of eluent was predicated on the specifics of each separation. Further details concerning the chiral HPLC methods used are provided below.

Method A: column CHIRALPAK IA 5 µm, 4.6×250 mm, eluent: EtOAc plus 0.1% of DEA, flow rate: 1.0 mL per minute; UV detection at 254 or 280 nm; column at RT, eluent was used as sample solvent.

Method B: column CHIRALPAK IA 5 µm, 4.6×250 mm, eluent: EtOAc/hexane (50:50) plus 0.1% of DEA, flow rate: 1.0 mL per minute; UV detection at 254 or 280 nm; column at RT, eluent was used as sample solvent.

Method C: column CHIRALPAK IA 5 µm 4.6×250 mm, eluent: hexane/ethanol (80:20 v/v) plus 0.1% of DEA, flow rate: 1.0 mL per minute; UV detection at 254 or 280 nm, column at RT, eluent was used as sample solvent.

Method D: column CHIRALPAK IA 5 µm 4.6×250 mm, eluent: hexane/ethanol (50:50 v/v) plus 0.1% of DEA, flow rate: 1.0 mL per minute; UV detection at 254 or 280 nm, column at RT, eluent was used as sample solvent.

Method E: column CHIRALPAK ID 5 µm 4.6×250 mm, eluent: hexane/ethanol (80:20 v/v) plus 0.1% of DEA, flow rate: 1.0 mL per minute; UV detection at 254 or 280 nm, column at RT, eluent was used as sample solvent.

Method F: column CHIRALPAK IA 5 µm 4.6×250 mm, eluent: DCM/ethanol (98:2 v/v) plus 0.1% of DEA, flow rate: 1.0 mL per minute; UV detection at 254 or 280 nm, column at RT, eluent was used as sample solvent.

Method G: column CHIRALPAK IA 5 µm 4.6×250 mm, eluent: DCM/ethanol (98:2 v/v) plus 0.1% of DEA, flow rate: 1.0 mL per minute; UV detection at 254 or 280 nm, column at RT, eluent was used as sample solvent.

Method H: column CHIRALPAK IB 5 µm 4.6×250 mm, eluent: TBME plus 0.1% of DEA, flow rate: 1.0 mL per minute; UV detection at 254 or 280 nm, column at RT, eluent was used as sample solvent.

Method I: column CHIRALPAK IC 5 µm 4.6×250 mm, eluent: TBME/ethanol (98:2 v/v) plus 0.1% of DEA, flow rate: 1.0 mL per minute; UV detection at 254 or 280 nm, column at RT, eluent was used as sample solvent.

Method J: column CHIRALPAK ID 5 µm 4.6×250 mm, eluent: EtOAc/DCM/IPA ethanol (3:1:1 v/v) plus 0.1% of DEA, flow rate: 1.0 mL per minute; UV detection at 254 or 280 nm, column at RT, eluent was used as sample solvent.

Method K: column CHIRALPAK IC 5 µm 4.6×250 mm, eluent: TBME/methanol (98:2 v/v) plus 0.1% of DEA, flow rate: 1.0 mL per minute; UV detection at 254 or 280 nm, column at RT, eluent was used as sample solvent.

Method L: column CHIRALPAK IB 5 µm 4.6×250 mm, eluent: TBME/methanol (98:2 v/v) plus 0.1% of DEA, flow rate: 1.0 mL per minute; UV detection at 254 or 280 nm, column at RT, eluent was used as sample solvent.

Preparative HPLC purifications were typically carried out on an Agilent 1200 instrument (preparative pump 1200 and ultraviolet multi wavelength detector 1200) with manual injection. The chromatography column used was Waters Sunfire 5 µm, C18, 19×100 mm, or XBridge 5 µm, C18, 19×100 mm depending on the type of eluent system employed, i.e. low pH or high pH conditions.

For high-pH HPLC purifications, eluent typically consisted of a mixture of solution A (0.04 M ammonium bicarbonate in $H_2O$ plus 0.1% of conc. $NH_4OH$) and solution B was MeCN. The gradient was adapted depending on the impurity profile in each sample purified, thereby allowing sufficient separation between the impurities and the desired compound.

In rare cases when high-pH HPLC purification did not provide sufficient purity, low-pH HPLC was applied. For low-pH HPLC purifications, eluent typically consisted of a mixture of solution A (0.1% of TFA in $H_2O$) and solution B was MeCN. The gradient was adapted depending on the impurity profile in each sample purified, thereby allowing sufficient separation between the impurities and the desired compound. TFA was removed from evaporated fractions by liquid-liquid extraction.

Chiral preparative HPLC purifications were performed on an Agilent 1200 instrument (preparative pump 1200 and ultraviolet multi wavelength detector 1200) with manual injection. The chiral columns used are CHIRALPAK IA 5 µm, 20×250 mm or CHIRALPAK IA 5 µm, 10×250 mm. All chiral HPLC methods were employed in an isocratic mode. The eluent mixture was selected based on the analytical chiral HPLC experiment (see above) that provided the best chiral separation.

$^1$H (300 MHz), $^{19}$F (282 MHz) and $^{13}$C NMR (75 MHz) spectra were recorded on a Bruker Avance DRX 300 instrument. Chemical shifts are expressed in parts per million, (ppm, δ units). Coupling constants are expressed in Hertz (Hz). Abbreviations for multiplicities observed in NMR spectra are as follows: s (singlet), d (doublet), t (triplet), q (quadruplet), m (multiplet), br (broad).

Solvents, reagents and starting materials were purchased and used as received from commercial vendors unless otherwise specified.

The following abbreviations are used:
Boc: tert-Butoxycarbonyl,
Cpd: Compound,
DAST: (Diethylamino)sulfur trifluoride,
DCM: Dichloromethane,
DEA: Diethylamine,
DMB: 2,4-Dimethoxybenzyl,
DMB-CHO: 2,4-Dimethoxybenzaldehyde,
DPP: Diphenylphosphiramide,
ee: Enantiomeric excess,
eq.: Equivalent(s),
EtOAc: Ethyl acetate,
EtOH: Ethanol,
g: Gram(s),
h: Hour(s),
IPA: iso-Propylalcohol,
L: Liter(s),
MeOH: Methanol,
µL: Microliter(s),
mg: Milligram(s),
mL: Milliliter(s),
mmol: Millimole(s),
min: Minute(s),
P: UV purity at 254 nm or 215 nm determined by HPLC-MS,
PMB: 4-Methoxybenzyl,
rt: Room temperature,
SES: 2-Trimethylsilylethanesulfonyl,
tBu: tert-Butyl,
TBDPS: tert-Butyldiphenylsilyl,
TBME: tert-Butyl methyl ether,
TFA: Trifluoroacetic acid,
TLC: Thin layer chromatography.

The intermediates and compounds described below were named using ChemBioDraw® Ultra version 12.0 (PerkinElmer).

I. Racemic Synthesis

I.1. General Synthetic Scheme for Racemic Synthesis

Compounds of the invention may be synthesized using the methodology described in Scheme 1, which represents the racemic product synthesis. The racemic products may then be subjected to chiral HPLC for chiral separation.

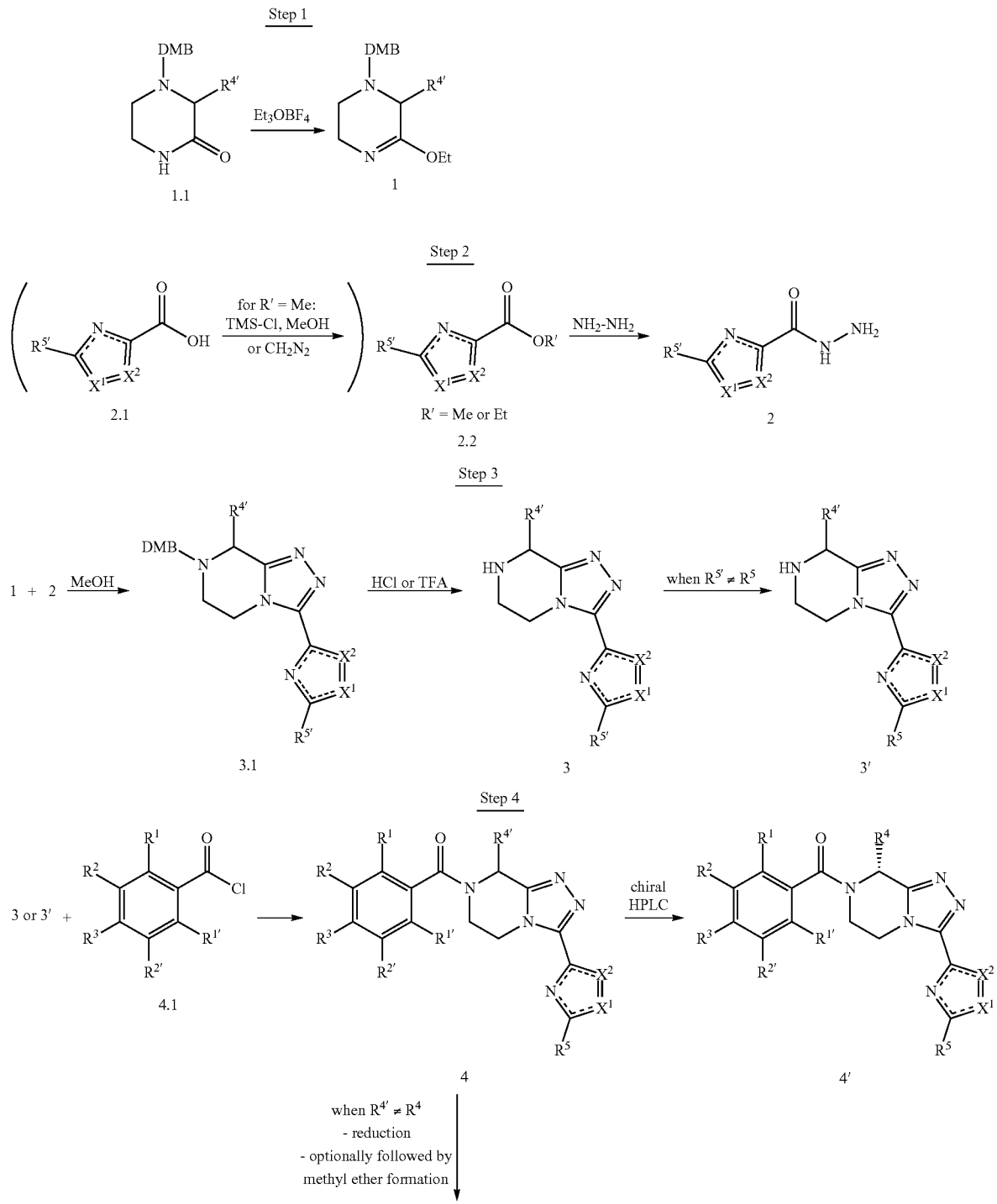

Scheme 1 General racemic synthetic scheme for the preparation of the compounds of the invention.

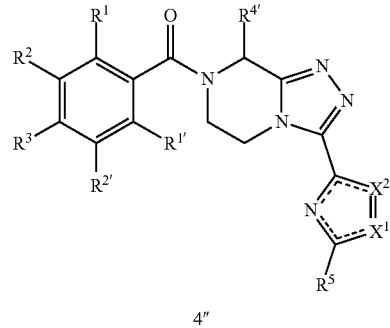

4"

The general synthetic scheme comprises the following steps:

Step 1: DMB-protected ketopiperazine 1.1 was converted to iminoether 1 by using the Meerwein reagent ($Et_3OBF_4$).

Step 2: Ester 2.2 was subsequently converted to acyl hydrazide 2. Ester 2.2 may be obtained be esterification of acid 2.1.

Step 3: Cyclodehydration between the acyl hydrazide 2 and the iminoether 1 furnished the protected triazolopiperazine 3.1. Thereafter, 3.1 was subjected to acidolytic deprotection to obtain 3. When applicable, $R^5$ was introduced from $R^{5'}$ affording 3'.

Step 4: The thus obtained triazolopiperazine intermediate 3 (or 3') was acylated through reaction with the appropriate acid chloride 4.1 to obtain the racemic final target structure represented by the general Formula 4. Optionally, $R^4$ may be transformed, for example by reduction of $R^{4'}$ when $R^{4'}$ contains a reducible group such as an ester group. The chiral compound 4' was subsequently obtained by purification using preparative chiral HPLC.

I.2. Step 1: Protection and Conversion to Iminoether 1

Method A: Conversion of DMB-Protected Ketopiperazine 1.1 to Iminoether 1

Method A is the procedure used for the synthesis of the iminoether intermediates 1 with a DMB protecting group and is detailed below:

Scheme 2 Conversion to iminoether 1.

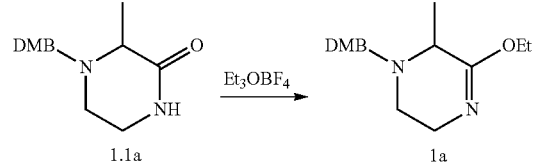

Method A is illustrated by the synthesis of intermediate 1a wherein $R^{4'}$ is Me.

Synthesis of 1-(2,4-dimethoxybenzyl)-5-ethoxy-6-methyl-1,2,3,6-tetrahydropyrazine 1a Scheme 3 Synthesis of 1-(2,4-dimethoxybenzyyl)-5-ethoxy-6-methyl-1,2,3,6- tetrahydropyrazine 1a.

Oven-dried (115° C.) sodium carbonate (18.6 g, 98 mmol, 2.25 eq.) was placed in a 500 mL round-bottom flask. The round-bottom flask was backfilled with Ar and then capped with a rubber septum. A solution of 4-(2,4-dimethoxybenzyl)-3-methylpiperazin-2-one 1.1a (20.6 g, 78 mmol, 1 eq.) in anhydrous DCM (250 mL) was added, followed by triethyloxonium tetrafluoroborate (18.6 g, 98 mmol, 1.25 eq.) in one portion. Thereafter, the reaction mixture was stirred further at RT for 1 h whereupon the reaction mixture was diluted with water (250 mL). The aqueous layer was extracted with DCM (3×150 mL). The organic layers were combined, dried over $MgSO_4$, filtered and concentrated under reduced pressure. The crude compound was then purified on silica gel (EtOAc) to afford the desired product 1a as orange oil. Yield: 13.2 g, 58%. LCMS: P=93%, retention time=1.8 min, $(M+H+H_2O)^+$: 311; $^1$H-NMR ($CDCl_3$): δ 7.23 (d, J=8.8 Hz, 1H), 6.48 (d, J=8.8 Hz, 1H), 6.44 (s, 1H), 4.02 (m, 2H), 3.92 (s, 3H), 3.91 (s, 3H), 3.86 (d, $J_{AB}$=14.0 Hz, 1H), 3.46 (d, $J_{AB}$=14.0 Hz, 1H), 3.44 (m, 2H), 3.10 (m, 1H), 2.79 (m, 1H), 2.32 (m, 1H), 1.35 (d, J=6.8 Hz, 3H), 1.24 (t, J=6.0 Hz, 3H).

I.3. Step 2: Formation of Acyl Hydrazide 2

Method B: Acyl Hydrazide 2

Method B is the procedure used for the synthesis of the acyl hydrazides 2 and is detailed below:

Scheme 4 Formation of acylhydrazide 2.

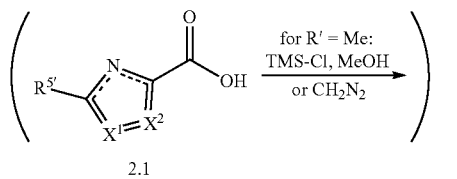

2.1

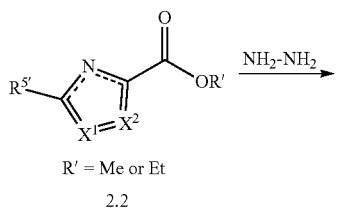

R' = Me or Et
2.2

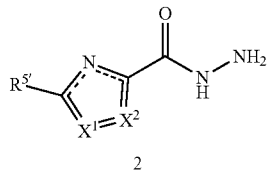

2

In a round-bottom flask equipped with a condenser, ester 2.2 (1 eq.) is dissolved in anhydrous EtOH and treated with hydrazine hydrate (1.2 to 20 eq., preferably 1.5 to 10 eq.) using a temperature range from RT to reflux. After allowing the reaction mixture to come to RT, the solution is concentrated under reduced pressure. Co-evaporations using a mixture of commercial DCM:MeOH (1:1) may be performed to remove residual water. The residue is then recrystallized and/or precipitated or purified on a pad of silica to afford 2.

I.4. Step 3: Cyclodehydration Leading to Triazolopiperazine 3

Method C: Cyclodehydration and acidolysis Method C is the procedure used for the synthesis of the triazolopiperazine 3 and is detailed below:

Scheme 5 Cyclodehydration leading to triazolopiperazine 3.

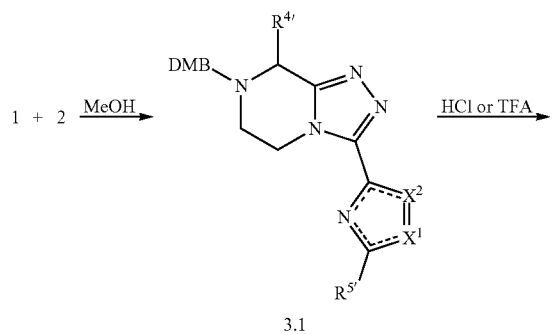

3.1

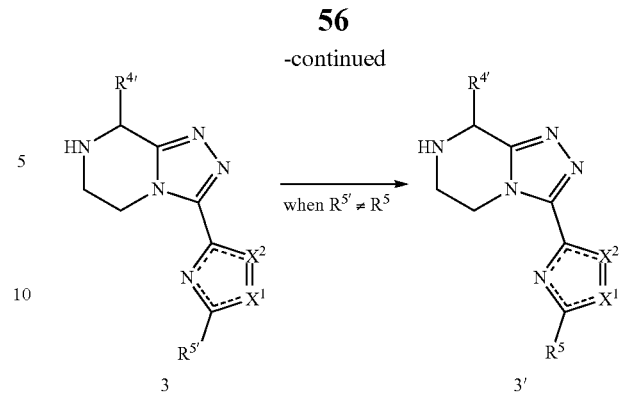

Step 1: In a round-bottom flask equipped with a condenser, imino-ether 1 (1 eq.) is dissolved in anhydrous MeOH, to which is added 2 (1 eq.) in one portion. The resulting solution is stirred at reflux overnight. Thereafter, the reaction mixture is brought to RT and the volatiles are removed under reduced pressure. The crude compound is then purified using silica gel chromatography to afford the desired product 3.1.

Step 2: In a round-bottom flask containing DCM is added 3.1 (1 eq.). Then, TFA (5 to 75 eq.), is added to the reaction mixture at RT. After 30 min stirring, the mixture is concentrated. Then DCM is added to the residue thus obtained, and washed with saturated $NaHCO_3$. The aqueous layer is extracted twice with DCM, the organic layers are washed with brine, dried over $MgSO_4$, filtered and concentrated under reduced pressure to obtain crude 3. The crude 3 may be directly used in the next step without further purification.

In one embodiment, alternative work-up equally used involves treatment of the dried residue obtained above with 4 M HCl/dioxane (20 eq.) at RT under stirring. After 5 min, $Et_2O$ is added to help precipitation. This precipitate is filtered off under vacuum, washed with $Et_2O$ and dried under high vacuum to furnish 3 as hydrochloride salt.

In another embodiment, HCl could be used for Step 2: HCl 4M solution in 1,4-dioxane (3 to 20 eq.) is added in one portion to a solution of 3.1 (1 eq.) in commercial isopropanol or ethanol. The reaction mixture is stirred at 60° C. After complete conversion monitored by HPLC-MS (1 to 10 h), the reaction mixture is allowed to cool to room temperature and then further cooled to 0° C. with an ice bath. Thereupon, $Et_2O$ is added. After 15-30 min stirring, the precipitate is filtered and dried in vacuo to afford 3 as hydrochloride salt.

Remark: When $R^{5'} \neq R^5 = H$, introduction of groups such as trifluoro- or difluoromethyl through direct trifluoromethylation or direct difluoromethylation (Ji Y. et al., PNAS, 2011, 108(35), 14411-14415; Fujiwara Y. et al., JACS, 2012, 134, 1494-1497) may be performed.

I.5. Step 4: Acylation Leading to Final Products

Method D: Acylation and chiral HPLC purification Method D is the procedure used for the synthesis of the racemic product 4 and its purification to obtain (R)-enantiomer 4' compounds of general Formula I. Method D is detailed below:

Scheme 6 Acylation and chiral HPLC purification.

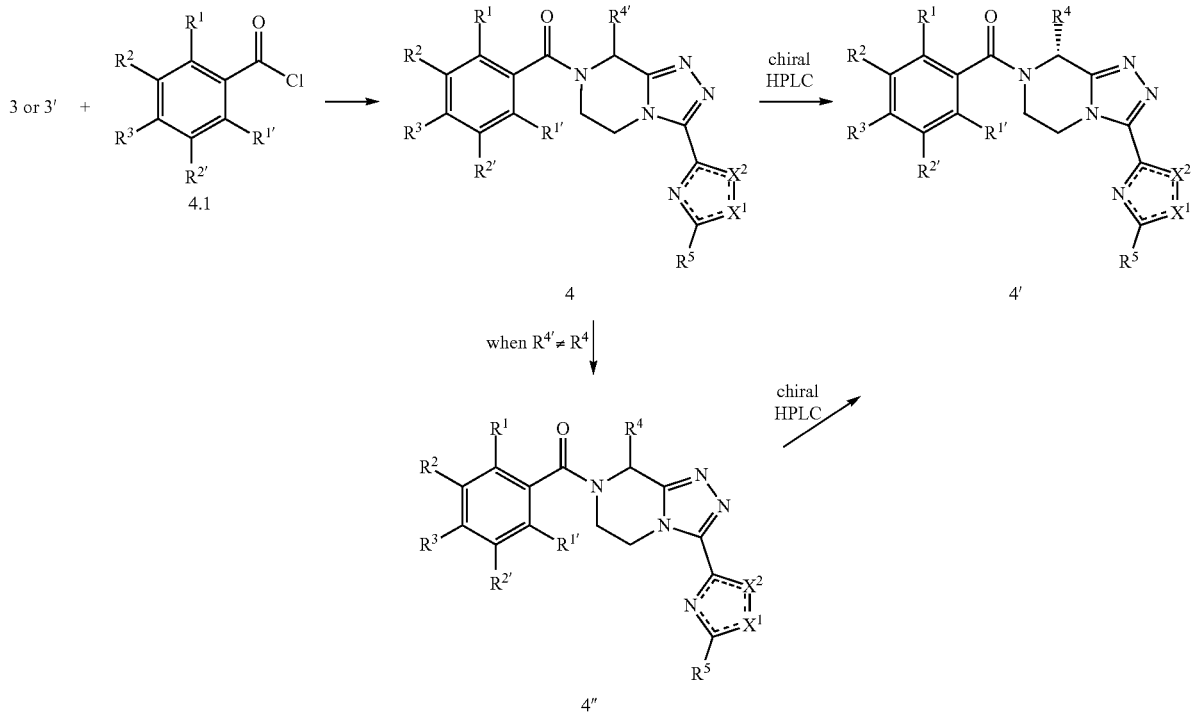

To a solution of crude 3 (1 eq.) in anhydrous DCM are added, at RT, 4.1 (1.17 to 1.3 eq.), followed by N-methylmorpholine (1 eq. to 3.5 eq.) dropwise over 15 sec. The reaction mixture is stirred at RT for 1 to 30 minutes and the milky suspension is poured into 1 M HCl solution or directly diluted with DCM. The aqueous phase is extracted with DCM. The organic phases are combined, optionally washed with 1 M NaOH, water, brine, dried over $MgSO_4$ and evaporated to dryness. The residue is solubilized in DCM and $Et_2O$ and is slowly added to induce precipitation. The solid was filtered off, washed with $Et_2O$ and dried under vacuum to afford 4. Alternatively, the residue is preliminary purified on silica gel before precipitation or purified on silica gel only.

Substituent $R^{4'}$ may then be transformed, when applicable, into $R^4$. One example of such transformation is illustrated by the synthesis of compound 12 wherein $R^4$ is hydroxyethyl group, obtained by reduction of $R^{4'}$=—$CH_2CO_2Alkyl$.

To a solution of 4 (1 eq.) in anhydrous THF is added, at −40° C., LAH (1 eq.), The reaction mixture is stirred at −40° C. for 5 to 30 minutes and the mixture is quenched with 1 M NaOH solution. The resulting mixture is extracted with DCM twice. The organic phases are combined, dried over $MgSO_4$ and evaporated to dryness. The residue 4" is then purified on silica gel.

Compound 4 or 4" may be purified by chiral preparative HPLC according to the abovementioned method to yield the corresponding chiral(R)-compound 4'. Compounds 4, 4" and 4' are compounds of Formula I of the invention.

II. Chiral Synthesis

II.1. General Synthetic Scheme for Chiral Synthesis

Chiral compounds of the invention may be synthesized using the chiral process of the invention described in Scheme 7.

Scheme 7 General synthetic scheme for the preparation of chiral compounds of the invention.

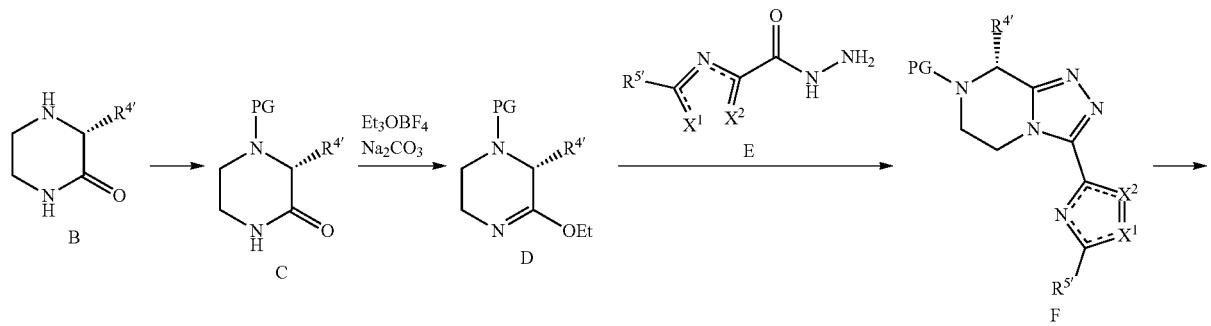

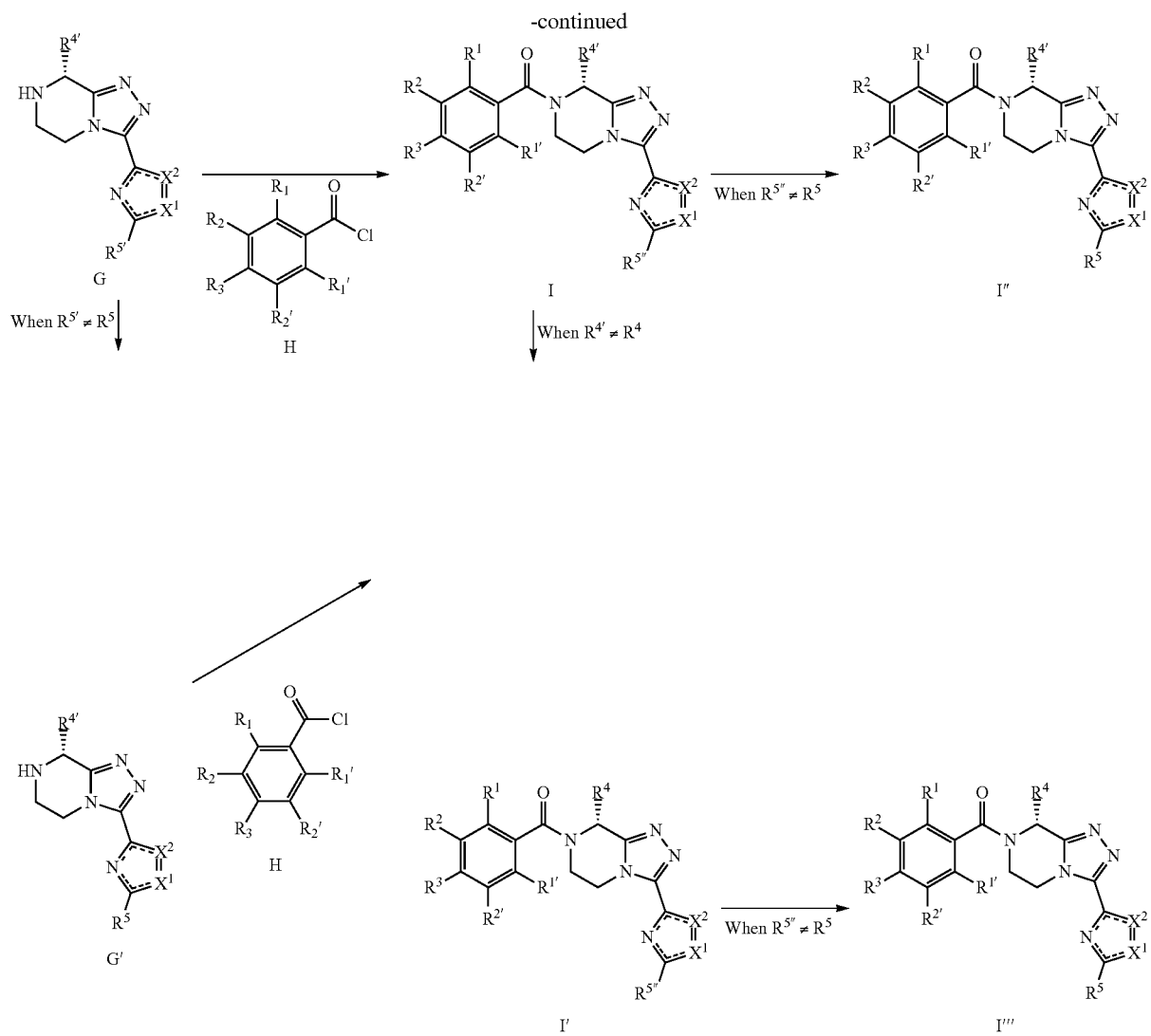

Chiral ketopiperazine B was protected with "PG" protecting group leading to PG-protected chiral ketopiperazine C. PG-protected chiral ketopiperazine C was converted to iminoether D by using the Meerwein reagent ($Et_3OBF_4$). Condensation reaction between the acyl hydrazide E and iminoether D was conducted under heating conditions in methanol to provide PG-protected piperazine F that was subsequently deprotected to yield compound of Formula G.

In one embodiment, when the protecting group PG is DMB, the DMB group deprotection step (from F to G) is carried out using TFA in DCM at rt, followed by either TFA salt exchange with HCl or extraction at high pH recovering free piperazine G.

When applicable, $R^5$ was introduced from $R^{5'}$ of G, affording G'.

Acylation of G or G' with the appropriate acid chloride H afforded the (R)-enantiomer of I typically in >90% enantiomeric excess (chiral HPLC). When applicable, $R^{4'}$ of I was then modified to afford $R^4$, furnishing I'.

When applicable, $R^{5''}$ of I or I' was then modified to afford $R^5$, furnishing I'' or I''' respectively.

II.2. Step 1: Protection of Ketopiperazine B

II.2.1. Protection of Ketopiperazine B with an Allyl to Afford Protected Ketopiperazine $C_1$ Scheme 8 Allyl protection of B.
Allyl protection is illustrated by the synthesis of intermediate (R)-4-allyl-3-methylpiperazin-2-one (i.e. compound $C_1$ wherein $R^{4'}$ is Me).

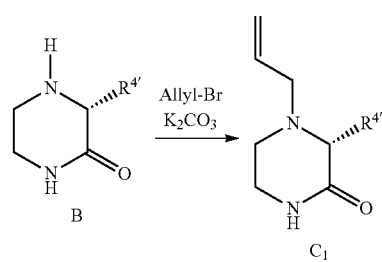

To a solution of (R)-3-methylpiperazin-2-one (0.5 g, 4.38 mmol) in commercial anhydrous THF (44 mL) at rt was added K$_2$CO$_3$ (1.2 g, 8.76 mmol). 3-bromoprop-1-ene (0.41 mL, 4.82 mmol) was then added at once, and the reaction mixture was stirred under reflux for 14 h.

The reaction mixture was allowed to cool to rt, concentrated and the residue was then solubilized with water (10 mL) and DCM (10 mL). The organic layer was separated, dried over MgSO$_4$, filtered and concentrated to afford 460 mg of yellow oil. $^1$H-NMR analysis shows that desired product was clearly the main product. Crude was used as-is in the following step.

LCMS: P>90%, retention time=0.2 min, (M+H)$^+$: 155. $^1$H-NMR (CDCl$_3$): δ 6.2 (m, 1H), 5.8 (m, 1H), 5.3 (m, 2H), 3.4 (m, 3H), 3.3 (q, J 7.2 Hz, 1H), 3.1 (m, 2H), 2.6 (m, 1H).

II.2.2. Protection of Ketopiperazine B with DPP to Afford Protected Ketopiperazine C$_2$ Scheme 9 DPP protection of B.

DPP protection is illustrated by the sythesis of intermediate (R)-4-(diphenylphosphoryl)-3-methylpiperazin-2-one (i.e. compound C$_2$ wherein R$^{4'}$ is Me).

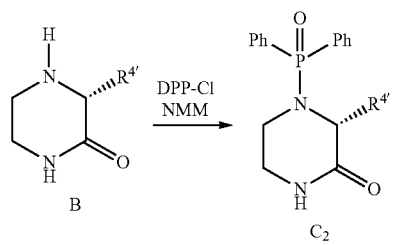

To a solution of (R)-3-methylpiperazin-2-one (0.5 g, 4.38 mmol) in commercial anhydrous DCM (9 mL) under Ar atmosphere at rt was added diphenylphosphinic chloride (0.84 mL, 4.38 mmol) in one portion, followed by N-methylmorpholine (1.2 mL, 8.76 mmol) dropwise. The reaction mixture was stirred under reflux for 72 h.

The reaction mixture was concentrated and the crude compound was then purified on silica gel (DCM/MeOH 99/1) to afford the desired product as colorless oil. Yield: 0.54 g, 88%. LCMS: P=98%, retention time=2.0 min, (M+H)$^+$: 315; chiral HPLC retention time=26.7 min, ee=99.4%; $^1$H-NMR (CDCl$_3$): δ 7.9 (m, 4H), 7.5 (m, 6H), 6.1 (bs, 1H), 3.9 (m, 1H), 3.6 (m, 1H), 3.3 (m, 2H), 3.2 (m, 1H), 1.5 (m, 3H).

II.2.3. Protection of Ketopiperazine B with Boc to Afford Protected Ketopiperazine C$_3$ Scheme 10 Boc protection of B.

Boc protection is illustrated by the synthesis of intermediate (R)-tert-butyl 2 methyl-3-oxopiperazine-1-carboxylate (i.e. compound C$_3$ wherein R$^{4'}$ is Me).

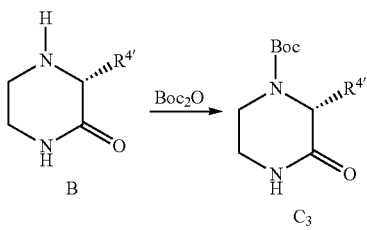

To a solution of (R)-3-methylpiperazin-2-one (0.33 g, 2.87 mmol) in commercial anhydrous DCM (10 mL) at 0° C. was added Boc$_2$O (0.77 mL, 3.30 mmol) in one portion. The reaction mixture was allowed to reach rt and stirred for 1 h.

The reaction mixture was concentrated under reduced pressure and the residue was taken up in DCM (100 mL) and washed with HCl 0.5M (90 mL) and brine (120 mL), dried over MgSO$_4$, filtered and concentrated under reduced pressure. The crude compound was then purified on silica gel (DCM/MeOH 99/1) to afford the desired product as colorless oil. Yield: 0.45 g, 33%. LCMS: P=98%, retention time=1.9 min, (M+H)$^+$: 215; $^1$H-NMR (CDCl$_3$): δ 6.3 (bs, 1H), 4.6 (m, 1H), 4.1 (m, 1H), 3.5 (m, 1H), 3.3-3.1 (m, 2H), 1.5 (m, 3H), 1.4 (s, 9H).

II.2.4. Protection of Ketopiperazine B with SES to Afford Protected Ketopiperazine C$_4$ Scheme 11 SES protection of B.

SES protection is illustrated by the synthesis of intermediate (R)-3-methyl-4-((2-(trimethylsilyl)ethyl)sulfonyl)piperazin-2-one (i.e. compound C$_4$ wherein R$^{4'}$ is Me).

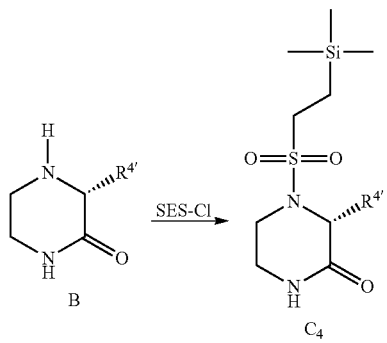

To a solution of (R)-3-methylpiperazin-2-one (0.25 g, 2.19 mmol) in commercial anhydrous DCM (4.5 mL) under Ar atmosphere at rt was added 2-(trimethylsilyl)ethanesulfonyl chloride (0.44 mL, 2.30 mmol) in one portion, followed by N-methylmorpholine (0.45 mL g, 4.38 mmol) dropwise. The reaction mixture was stirred at rt for 16 h.

The reaction mixture was diluted with water (10 mL) and DCM (10 mL). The organic layer was separated, dried over MgSO$_4$, filtered and concentrated. The crude compound was then purified on silica gel (DCM/MeOH 99/1) to afford the desired product as colorless oil. Yield: 0.08 g, 13%. LCMS: P=95%, retention time=2.1 min, (M+H)$^+$: 279; chiral HPLC retention time=7.2 min, ee=99.6%; $^1$H-NMR (CDCl$_3$): δ 6.1 (bs, 1H), 4.5 (m, 1H), 3.8 (m, 1H), 3.6 (m, 1H), 3.4 (m, 1H), 3.3 (m, 1H), 2.9 (m, 2H), 1.6 (m, 3H), 1.0 (m, 2H), 0.1 (s, 9H).

II.3. Step 2: Conversion to Iminoether D

Method E: Conversion to Iminoether

General Method E is the procedure used for the synthesis of intermediates D.

Scheme 12 Conversion to iminoether D.
Method E is illustrated by the synthesis of intermediate (R)-1-(2,4-dimethoxybenzyl)-5-ethoxy-6-methyl-1,2,3,6-tetrahydropyrazine $D_5$-1(i.e. compound D wherein PG is DMB and $R^{4'}$ is Me).
The corresponding DMB-protected ketopiperazine $C_5$ is commercially available.

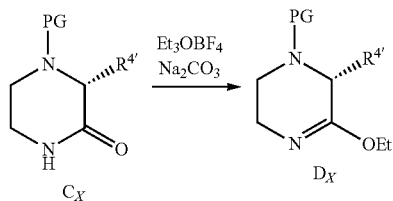

Oven dried (115° C.) sodium carbonate (2.48 g, 23.40 mmol, 2.25 eq.) was placed in a round-bottom flask. The round-bottom flask was backfilled with Ar and then capped with a rubber septum. A solution of (R)-4-(2,4-dimethoxybenzyl)-3-methylpiperazin-2-one C-1 (2.75 g, 10.40 mmol, 1 eq.) in anhydrous DCM (35 mL) was added, followed by freshly prepared triethyloxonium tetrafluoroborate (2.48 g, 13.05 mmol, 1.25 eq.) in one portion. Thereafter the reaction mixture was stirred further at rt for 45 min to 1 hour, whereupon the reaction mixture was diluted with saturated aqueous NaHCO$_3$ (100 mL). The aqueous layer was extracted with DCM (3×200 mL). The organic layers were combined, dried over MgSO$_4$, filtered and concentrated under reduced pressure to afford 3.1 g of yellow oil. The crude compound was then purified on silica gel (EtOAc/MeOH: 99/1) to afford the desired product D-1 as a pale yellow oil. Yield: 1.44 g, 48%. LCMS: P=95%, retention time=1.8 min, (M+H2O+H)$^+$: 311; chiral HPLC retention time=12.3 min, ee>97%. $^1$H-NMR (CDCl$_3$): δ 7.23 (d, J=8.8, 1H), 6.48 (d, J=8.8, 1H), 6.44 (s, 1H), 4.02 (m, 2H), 3.92 (s, 6H), 3.86 (d, $J_{AB}$=14.0, 1H), 3.46 (d, $J_{AB}$=14.0, 1H), 3.44 (m, 2H), 3.10 (m, 1H), 2.79 (m, 1H), 2.32 (m, 1H), 1.35 (d, J=6.8, 3H), 1.24 (t, J=6.0, 3H).

The reaction mixture may alternatively be treated with brine. After stirring for about 20 min, additional water and DCM were added leading to phase separation. The organic layers were then dried over MgSO$_4$, filtered and concentrated under reduced pressure. The crude compound was then purified on silica gel.

Method E is further illustrated by the synthesis of intermediate (R)-1-allyl-5-ethoxy-6-methyl-1,2,3,6-tetrahydropyrazine (i.e. compound Di wherein PG is allyl and $R^{4'}$ is Me).

To a solution of (R)-4-allyl-3-methylpiperazin-2-one (0.35 g, 2.27 mmol, 1 eq.) in DCM (7.6 mL) at 0° C. was added sodium carbonate (0.54 g, 5.11 mmol, 2.25 eq.) in one portion, followed by commercial triethyloxonium tetrafluoroborate (0.54 g, 2.84 mmol, 1.25 eq.) in one portion. Thereafter the reaction mixture was stirred further at rt for 45 min, whereupon the reaction mixture was diluted with DCM (10 mL) and brine (10 mL). The layers were separated and the aqueous layer was further extracted with DCM (2×5 mL). The organic layers were combined, dried over MgSO$_4$, filtered and concentrated under reduced pressure. The crude compound was then purified on silica gel (EtOAc) to afford the desired product as colorless oil. Yield: 0.19 g, 46%. LCMS: P=95%, retention time=1.5 min, (M+H)$^+$: 183; $^1$H-NMR (CDCl$_3$): δ 5.9 (m, 1H), 5.2 (m, 2H), 4.0 (m, 2H), 3.5 (m, 2H), 3.3 (m, 1H), 3.1-3.0 (m, 2H), 2.8 (m, 1H), 2.4 (m, 1H), 1.3 (m, 6H).

The following intermediates were also prepared from the ad hoc reagents:

(R)-(3-ethoxy-2-methyl-5,6-dihydropyrazin-1(2H)-yl)diphenylphosphine oxide in 44% yield. LCMS: P=98%, retention time=2.0 min, (M+H$_2$O+H)$^+$: 361; chiral HPLC retention time=4.8 min, ee=99.4%; $^1$H-NMR (CDCl$_3$): δ 7.9 (m, 4H), 7.5 (m, 6H), 4.0 (m, 2H), 3.7 (m, 1H), 3.6 (m, 1H), 3.5 (m, 1H), 3.1 (m, 2H), 1.4 (m, 3H), 1.2 (m, 3H).

(R)-tert-butyl 3-ethoxy-2-methyl-5,6-dihydropyrazine-1(2H)-carboxylate in 68% yield. LCMS: P=98%, retention time=1.8 min, (M+H$_2$O+H)$^+$: 261; $^1$H-NMR (CDCl$_3$): δ 4.3 (m, 1H), 4.1 (m, 2H), 3.9 (m, 1H), 3.5 (m, 2H), 2.9 (m, 1H), 1.5 (s, 9H), 1.3 (d, J=6.9 Hz, 3H), 1.2 (t, J=7.0 Hz, 3H).

(R)-5-ethoxy-6-methyl-1-((2-(trimethylsilyl)ethyl)sulfonyl)-1,2,3,6-tetrahydropyrazine in 68% yield. LCMS: P=70%, retention time=2.0 min, (M+H$_2$O+H)$^+$: 325; chiral HPLC retention time=4.8 min, ee=97.3%; $^1$H-NMR (CDCl$_3$): δ 4.3 (m, 1H), 4.1 (m, 2H), 3.6 (m, 3H), 3.2 (m, 1H), 2.9 (m, 2H), 1.5 (m, 3H), 1.3 (m, 3H), 1.0 (m, 2H), 0.0 (s, 9H).

II.4. Step 3: Cyclodehydration Leading to F

Method F: Cyclodehydration
General Method F is the general procedure used for the synthesis of chiral triazolopiperazine intermediates F.

Scheme 13 Formation of acylhydrazide F.
In a round-bottom flask equipped with a condenser, imino-ether D (1 eq.) was dissolved in anhydrous MeOH, to which was added E (1 eq.) in one portion. The resulting solution was stirred at a temperature ranging from 55° C. to 70° C. for a period of time ranging from 6 hours to 8 hours. Completion of the reaction was monitored by HPLC analysis. The reaction mixture was cooled down to rt and the solvent was removed under reduced pressure. The crude compound was then purified by silica gel chromatography to afford the desired product F. In an embodiment of the invention, the crude compound precipitates during cooling of the reaction mixture. In this case, the precipitate is stirred at rt in MeOH for about 5 hours before being filtered, washed with MeOH and oven dried.

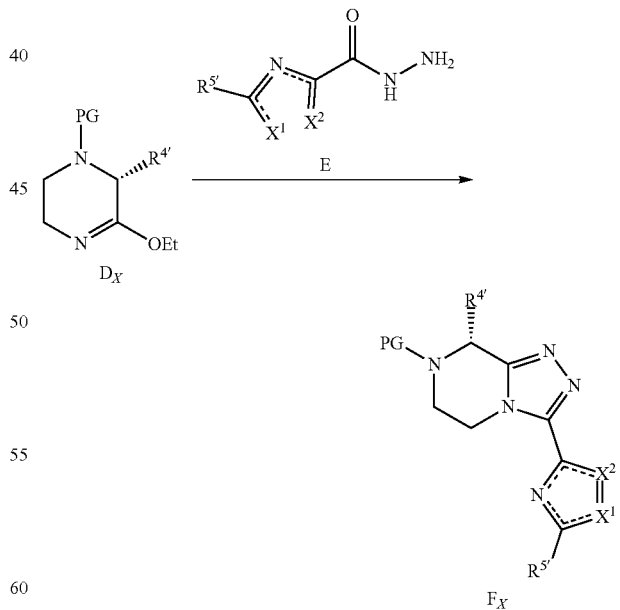

Cyclodehydration is illustrated by the synthesis of intermediate (R)-5-(7-allyl-8-methyl-5,6,7,8-tetrahydro-[1,2,4]triazolo[4,3-a]pyrazin-3-yl)-3-methyl-1,2,4-thiadiazole (i.e. compound Fi wherein PG is allyl, $R^{4'}$ is Me, $X^1$ is N, $X^2$ is S and $R^{5'}$ is methyl).

To (R)-1-allyl-5-ethoxy-6-methyl-1,2,3,6-tetrahydropyrazine (0.14 g, 0.77 mmol) at rt was added 3-methyl-1,2,4-thiadiazole-5-carbohydrazide (0.12 g, 0.77 mmol) at once. The mixture was diluted with commercially anhydrous MeOH (0.77 mL) to allow complete solubilization and the resulting mixture was heated to 60° C. for 16 h.

The reaction mixture was then allowed to reach rt whereupon the solvent was removed under reduced pressure (1-2 mbar). The crude residue was then dissolved in DCM (10 mL), and thus-obtained organic phase washed with NaOH (1 M, 10 mL). The organic layer was then dried over $MgSO_4$, filtered and concentrated under reduced pressure (1-2 mbar) the desired product as a yellow solid. Yield: 0.09 g, 42%. LCMS: P=95%, retention time=1.6 min, $(M+H)^+$: 277; chiral HPLC retention time=21.6 min, ee=98.9%; $^1$H-NMR (CDCl$_3$): δ 5.9 (m, 1H), 5.3 (m, 2H), 4.5 (m, 1H), 4.4 (m, 1H), 4.1 (m, 1H), 3.5 (m, 1H), 3.3 (m, 1H), 3.1 (m, 1H), 2.8 (m, 1H), 2.7 (s, 3H), 1.6 (m, 3H).

The following intermediates were also prepared from the ad hoc reagents:

(R)-(8-methyl-3-(3-methyl-1,2,4-thiadiazol-5-yl)-5,6-dihydro-[1,2,4]triazolo[4,3-a]pyrazin-7(8H)-yl)diphenylphosphine oxide in 31% yield (reaction time: 48 h and silica gel purification (EtOAc)). LCMS: P=96%, retention time=2.2 min, $(M+H)^+$: 437; chiral HPLC retention time=7.5 min, ee=98.3%; $^1$H-NMR (CDCl$_3$): δ 7.9 (m, 4H), 7.5 (m, 6H), 4.9 (m, 1H), 4.8 (dd, J=3.1, 13.6 Hz, 1H), 4.3 (dt, J=4.9, 12.2 Hz, 1H), 3.6 (m, 1H), 3.5 (m, 1H), 2.7 (s, 3H), 1.6 (d, J=6.9 Hz, 3H).

(R)-tert-butyl 8-methyl-3-(3-methyl-1,2,4-thiadiazol-5-yl)-5,6-dihydro-[1,2,4]triazolo[4,3-a]pyrazine-7(8H)-carboxylate in 83% yield (reaction time: 48 h). LCMS: P=97%, retention time=2.3 min, $(M+H)^+$: 337; chiral HPLC retention time=19.4 min, ee=95.1%; $^1$H-NMR (CDCl$_3$): δ 5.7 (m, 1H), 4.9 (m, 1H), 4.5 (m, 1H), 4.2 (m, 1H), 3.3 (m, 1H), 2.7 (s, 3H), 1.6 (d, J=6.9 Hz, 3H), 1.5 (s, 9H).

(R)-3-methyl-5-(8-methyl-7-((2-(trimethylsilyl)ethyl)sulfonyl)-5,6,7,8-tetrahydro-[1,2,4]triazol[4,3-a]pyrazin-3-yl)-1,2,4-thiadiazole in 28% yield (reaction time: 48 h). LCMS: P=40%, retention time=2.5 min, $(M+H)^+$: 401; chiral HPLC retention time=7.1 min, ee=92.4%; $^1$H-NMR (CDCl$_3$): δ 4.9 (m, 1H), 4.3 (m, 1H), 4.1 (m, 1H), 3.6 (m, 1H), 3.0 (m, 1H), 2.7 (s, 3H), 1.6 (m, 2H), 1.4 (m, 3H), 1.0 (m, 2H), 0.0 (s, 9H).

II.5. Step 4: PG-Deprotection

The methods of deprotection of above Protecting Groups (PGs) are known to those skill-in-the-art. As examples, one may refer to "Greene's Protective Groups in Organic Synthesis":

Allyl: p. 806 of fourth edition;
DPP: p. 844 of fourth edition;
Boc: p. 725 of fourth edition;
SES: p. 854 in fourth edition.
Method G: DMB deprotection—TFA/DCM Scheme 14 DMB deprotection.

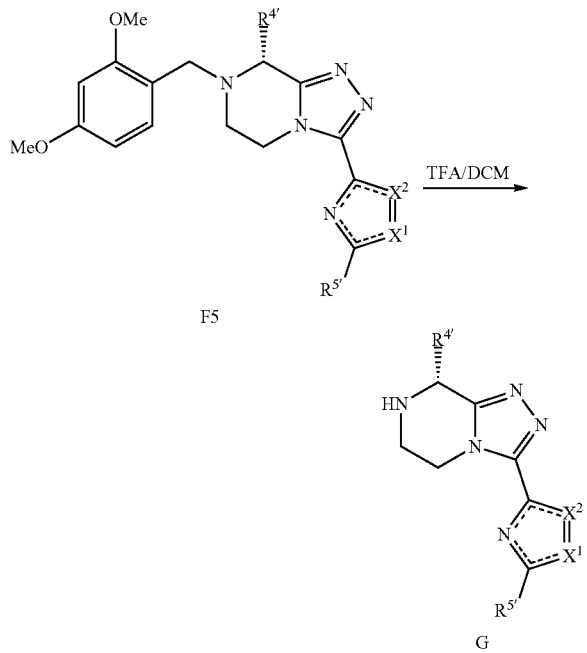

Deprotection of DMB may be performed using TFA.

When crude or precipitated F was used (in opposition to purified F on silica gel), pre-washing was performed before deprotection as follow: F was dissolved in DCM and optionally washed with 1M NaOH in order to remove remaining E. The DCM extracts were then dried over magnesium sulphate, filtered and the filter cake washed with DCM.

F was diluted with DCM and TFA (7.6 eq.) was added to the DCM solution of F at RT. The mixture was stirred at rt for 2 h-2 h30. Completion of the deprotection was monitored by HPLC. Water was added, the mixture stirred for 30 minutes and filtered. The filter cake was washed with water and DCM. The filtrate layers were separated. The pH of the aqueous layer was adjusted to 12-13 by the addition of 4M NaOH. Sodium chloride was then added and the aqueous solution was extracted with DCM. The DCM extract comprising G was concentrated and was used in the next step without further purification. II.6. Optional conversion of $R^{5'}$ to $R^5$ in triazolopiperazine Scheme 15 conversion of $R^{5'}$ to $R^5$ in triazolopiperazine G leading to G'.

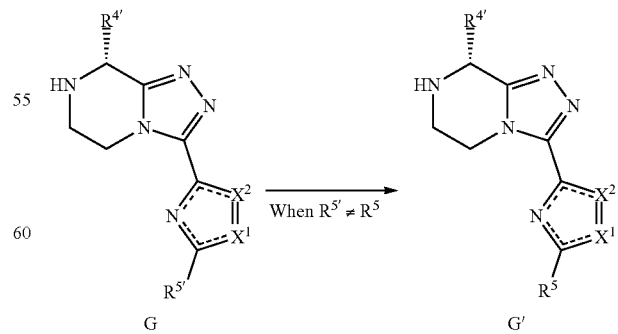

Substituent $R^5$ may then be introduced, when applicable, from $R^{5'}$ (especially when $R^{5'}$ =H). One example of such transformation is illustrated by the synthesis of intermediate G' wherein $R^5$ is trifluoromethyl.

To a solution of G (1 eq.) in DCM/water (3/1) are added, at rt, sodium trifluoromethansulfonate (3 eq.) and 2-hydroperoxy-2-methylpropane (5 eq.). The reaction mixture is not stirred and left at rt. Monitoring conversion by HPLC-MS, extra amount of each reagent can be added if required. The resulting mixture is diluted with DCM and quenched with 4 M NaOH saturated solution. Layers were separated and aqueous layer was extracted twice with EtOAc. The organic phases are combined, dried over $MgSO_4$ and evaporated to dryness. The residue is purified on silica gel or used crude in next step.

A further example of such transformation is illustrated by the synthesis of intermediate G' wherein $R^5$ is difluoromethyl:

To a suspension of G ($R^{5'}$=H) (R)-5-(8-methyl-5,6,7,8-tetrahydro-[1,2,4]triazolo[4,3-a]pyrazin-3-yl)-1,2,4-thiadiazole (0.29 g, 1.13 mmol) and bis(difluoromethylsulfinyloxy)zinc (0.67 g, 2.26 mmol) in DCM (5 mL) and Water (2 mL), was added TFA (0.09 mL, 1.13 mmol), followed by slow addition of 2-hydroperoxy-2-methylpropane (0.77 mL, 5.64 mmol) with vigorous stirring.

When conversion was not increasing any more (HPLC-MS monitoring) bis(difluoromethylsulfinyloxy)zinc and 2-hydroperoxy-2-methylpropane were added at rt still with vigorous stirring (3 additional times (1.001 g, 3.39 mmol) and (0.773 mL, 5.64 mmol) respectively).

After 4 days in total, reaction mixture was diluted with EtOAc (50 mL) and carefully quenched with $NaHCO_3$sat. solution (30 mL) and then $NaHCO_3$ solid until no bubbling was observed. Reaction mixture was filtered on Celite pad and phases of the filtrate were separated. Aqueous phase was filtered again on Celite pad then filtrate was extracted with EtOAc (2×50 mL). Organic phases were combined, dried over $MgSO_4$, filtered and concentrated under reduced pressure. The crude compound was then purified on silica gel (DCM/MeOH 99/1) to afford the desired product as colorless oil. Yield: 0.03 g, 10%. LCMS: P=97%, retention time=1.8 min, (M+H)$^+$: 273; $^1$H-NMR (CDCl$_3$): δ 6.8 (t, $J_{H-F}$=53.5 Hz, 1H), 4.7 (m, 1H), 4.3 (m, 2H), 3.5 (m, 1H), 3.3 (m, 1H), 1.7 (d, J=6.7 Hz, 3H); $^{19}$F-NMR (CDCl$_3$): δ −113.5 (dd, J=3.2, 53.5 Hz, 2F).

II.7. Step 5: Acylation Leading to Products I

Method H: Acylation NMM/DCM

General Method H is the general procedure used for the synthesis of (R)-enantiomer of Formula I of the invention.

Scheme 16 Acylation.

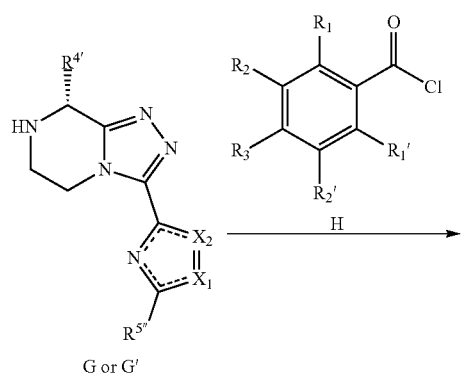

G or G'

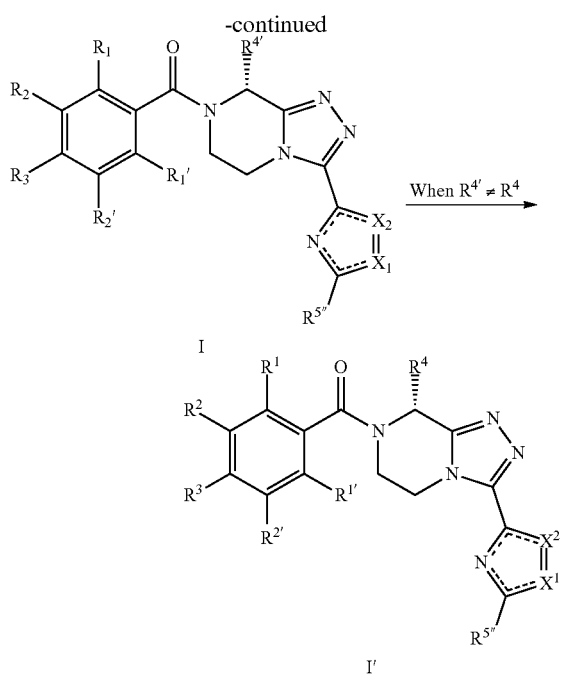

To a solution of crude G or G' (1 eq.) in anhydrous DCM were added at 0° C. H (1.3 eq.), followed by N-methylmorpholine (2.2 eq.) dropwise over 15 sec. The reaction mixture was stirred at rt for 10 minutes and, the milky suspension was poured into 1 M HCl. The aqueous phase was extracted with DCM. The organic phases were combined, washed with 1 M NaOH, brine, dried over $MgSO_4$ and evaporated to dryness. The crude compound was purified by silica gel chromatography to afford the desired product (R)-I.

Measurement of % ee confirmed that no detectable racemization occurs during the acidolytic deprotection and N-acylation steps.

Method I: Acylation—Biphasic Conditions

Alternatively, the reaction may be performed under biphasic conditions.

In this case, saturated sodium hydrogen carbonate solution was added to the DCM slurry of G or G' (1 eq.) at rt. H (1 eq.) was added and the mixture stirred for a period of time ranging from about 20 minutes to overnight at rt. Completion of the reaction was monitored by HPLC. The layers were separated and the DCM phase washed with water. The DCM extracts were dried with magnesium sulphate and filtered, washing the filter cake with DCM. The DCM extracts were then concentrated. TBME was added and the resulting slurry stirred overnight at rt. The solid was collected by filtration, washed with TBME and pulled dry. The crude compound may be purified by silica gel chromatography or by crystallisation.

Measurement of % ee confirmed that no detectable racemization occurs during the acidolytic deprotection and N-acylation steps.

Substituent $R^{4'}$ may then be transformed, when applicable, into $R^4$ (see racemic synthesis).

II.8. Optional Further Transformation Leading to Products I"/I"' from I/I'

Compound 45: From compound I/I' wherein $R^{5"}$=1-((tert-butyldiphenylsilyl)oxy)ethyl, well known tert-butylammonium fluoride TBDPS deprotection of alkoxy was applied, followed by DAST fluorination of the latter alcohol, leading to racemic compound 45. Both diastereomers can be separated by purification on preparative HPLC to afford 45-1 and 45-2.

Compound 43: From compound I/I' wherein $R^{5''}$=1-((tert-butyldiphenylsilyl)oxy)ethyl, well known tert-butylammonium fluoride TBDPS deprotection of alkoxy was applied, followed by Dess-Martin oxidation, then followed by DAST fluorination of the latter ketone, leading to compound 43.

III. Chemical Characterization

Compound 1: HPLC-MS: $t_R$=4.1 min, (M+H)$^+$=409; Chiral HPLC (Method C): % ee=99.0; $^1$H-NMR (CDCl$_3$): δ 7.6 (m, 2H), 7.3 (m, 1H), 5.8 (m, 1H), 4.9 (m, 1H), 4.6 (m, 1H), 4.3 (m, 1H), 3.6 (m, 1H), 2.7 (s, 3H), 1.7 (d, 3H).

Compound 2: HPLC-MS: $t_R$=3.8 min, (M+H)$^+$=373; Chiral HPLC (Method A): % ee=98.0; $^1$H-NMR (300 MHz, CDCl$_3$): δ 7.5 (m, 2H), 7.2 (m, 2H), 5.8 (m, 1H), 4.9 (dd, 1H), 4.6 (m, 1H), 4.3 (m, 1H), 3.6 (m, 1H), 3.1 (q, 2H), 1.8 (d, 3H), 1.4 (t, 3H); $^{19}$F-NMR (CDCl$_3$): δ −98.5.

Compound 3: HPLC-MS: $t_R$=3.8 min, (M+H)$^+$=375; Chiral HPLC (Method C): % ee>99.8; $^1$H-NMR (CDCl$_3$): δ 7.5 (m, 4H), 5.8 (m, 1H), 4.9 (m, 1H), 4.6 (m, 1H), 4.3 (m, 1H), 3.6 (m, 1H), 2.7 (s, 3H), 1.7 (d, 3H).

Compound 4: HPLC-MS: $t_R$=3.9 min, (M+H)$^+$=393; Chiral HPLC (Method C): % ee=99.0; $^1$H-NMR (CDCl$_3$): δ 7.6 (m, 1H), 7.3 (s, 1H), 7.2 (m, 1H), 5.8 (m, 1H), 4.9 (m, 1H), 4.6 (m, 1H), 4.3 (m, 1H), 3.6 (m, 1H), 2.7 (s, 3H), 1.7 (d, 3H); $^{19}$F-NMR (CDCl$_3$): δ −98.4.

Compound 5: HPLC-MS: $t_R$=3.4 min, (M+H)$^+$=359; Chiral HPLC (Method C): % ee=99.0; $^1$H-NMR (CDCl$_3$): δ 7.5 (m, 2H), 7.3 (m, 2H), 5.8 (m, 1H), 4.9 (m, 1H), 4.6 (m, 1H), 4.3 (m, 1H), 3.5 (m, 1H), 2.7 (s, 3H), 1.7 (d, 3H); $^{19}$F-NMR (CDCl$_3$): δ −98.4.

Compound 6: HPLC-MS: $t_R$=3.8 min, (M+H)$^+$=393; Chiral HPLC (Method C): % ee=99.5; $^1$H-NMR (CDCl$_3$): δ 7.6 (m, 1H), 7.3 (m, 2H), 5.7 (m, 1H), 4.9 (m, 1H), 4.5 (m, 1H), 4.3 (m, 1H), 3.5 (m, 1H), 2.7 (s, 3H), 1.8 (d, 3H); $^{19}$F-NMR (CDCl$_3$): δ −96.2.

Compound 7: HPLC-MS: $t_R$=3.8 min, (M+H)$^+$=395; Chiral HPLC (Method C): % ee=98.9; $^1$H-NMR (CDCl$_3$): δ 7.1 (m, 2H), 5.8 (m, 1H), 5.0 (m, 1H), 4.5 (m, 1H), 4.3 (m, 1H), 3.6 (m, 1H), 2.7 (s, 3H), 1.8 (d, 3H); $^{19}$F-NMR (CDCl$_3$): δ −75.8.

Compound 8: HPLC-MS: $t_R$=3.7 min, (M+H)$^+$=395; Chiral HPLC (Method C): % ee=99.0; $^1$H-NMR (CDCl$_3$): δ 7.1 (m, 2H), 6.2 (m, 1H), 5.3-5.0 (m, 2H), 4.3-3.6 (m, 2H), 2.7 (s, 3H), 1.8 (m, 3H); $^{19}$F-NMR (CDCl$_3$): δ −49.4, −72.0, −77.4.

Compound 9: HPLC-MS: $t_R$=3.6 min, (M+H)$^+$=377; Chiral HPLC (Method C): % ee=99.4; $^1$H-NMR (CDCl$_3$): δ 7.3 (m, 3H), 5.8 (m, 1H), 4.9 (dd, 1H), 4.6 (m, 1H), 4.3 (td, 1H), 3.6 (td, 1H), 2.7 (s, 3H), 1.7 (d, 3H); $^{19}$F-NMR (CDCl$_3$): δ −72.1, −74.4.

Compound 10: HPLC-MS: $t_R$=4.0 min, (M+H)$^+$=413; Chiral HPLC (Method C): % ee=99.0; $^1$H-NMR (CDCl$_3$): δ 7.2 (m, 1H), 6.2 (m, 1H), 5.2-5.0 (m, 2H), 4.3 (m, 1H), 3.9-3.4 (m, 2H), 2.7 (s, 3H), 1.8 (m, 3H); $^{19}$F-NMR (CDCl$_3$): δ −54.2, −56.3, −67.1, −72.8.

Compound 11: HPLC-MS: $t_R$=3.2 min, (M+H)$^+$=389; Chiral HPLC (Method A): % ee>99.8; $^1$H-NMR (CDCl$_3$): δ 7.5 (m, 2H), 7.2 (m, 2H), 6.1 (m, 1H), 4.9 (m, 1H), 4.3 (m, 2H), 3.9 (m, 2H), 3.6 (m, 1H), 2.8 (m, 1H), 2.4 (m, 1H), 2.2 (m, 1H); $^{19}$F-NMR (CDCl$_3$): δ −97.9.

Compound 12: is racemate of compound 11.

Compound 13: HPLC-MS: $t_R$=4.1 min, (M+H)$^+$=357; Chiral HPLC (Method B): % ee=98.7; $^1$H-NMR (CDCl$_3$): δ 7.5 (m, 2H), 7.2 (m, 2H), 5.8 (m, 1H), 4.8 (dd, 1H), 4.6 (m, 1H), 4.3 (td, 1H), 3.6 (td, 1H), 2.9 (q, 2H), 1.8 (d, 3H), 1.4 (t, 3H); $^{19}$F-NMR (CDCl$_3$): δ −98.7.

Compound 14: is racemate of compound 5.

Compound 15: HPLC-MS: $t_R$=3.4 min, (M+H)$^+$=359; Chiral HPLC (Method B): % ee>99.8; $^1$H-NMR (CDCl$_3$): δ 7.5 (m, 1H), 7.2 (m, 3H), 5.8 (m, 1H), 4.9 (dd, 1H), 4.6 (m, 1H), 4.3 (td, 1H), 3.6 (td, 1H), 2.7 (s, 3H), 1.7 (d, 3H); $^{19}$F-NMR (CDCl$_3$): δ −96.2.

Compound 16: HPLC-MS: $t_R$=3.7 min, (M+H)$^+$=375; $^1$H-NMR (CDCl$_3$): δ 7.5-7.3 (m, 4H), 5.8 (m, 1H), 4.9 (dd, 1H), 4.6 (m, 1H), 4.3 (td, 1H), 3.6 (td, 1H), 2.7 (s, 3H), 1.7 (d, 3H).

Compound 17: HPLC-MS: $t_R$=3.6 min, (M+H)$^+$=377; $^1$H-NMR (CDCl$_3$): δ 7.3 (m, 1H), 7.0 (m, 2H), 5.8 (m, 1H), 4.9 (dd, 1H), 4.6 (m, 1H), 4.3 (td, 1H), 3.6 (td, 1H), 2.8 (s, 3H), 1.8 (d, 3H); $^{19}$F-NMR (CDCl$_3$): δ −101.2.

Compound 18: HPLC-MS: $t_R$=3.5 min, (M+H)$^+$=377; $^1$H-NMR (CDCl$_3$): δ 7.5 (m, 1H), 7.0-6.9 (m, 2H), 6.2 (m, 1H), 5.2-4.9 (m, 2H), 4.3 (m, 1H), 4.0-3.7 (m, 1H), 2.7 (s, 3H), 1.7 (m, 3H); $^{19}$F-NMR (CDCl$_3$): δ −95.7, −102.5.

Compound 19: HPLC-MS: $t_R$=3.6 min, (M+H)$^+$=355; $^1$H-NMR (CDCl$_3$): δ 7.4 (m, 4H), 5.8 (m, 1H), 4.9 (dd, 1H), 4.6 (m, 1H), 4.3 (td, 1H), 3.6 (td, 1H), 2.7 (s, 3H), 2.4 (s, 3H), 1.7 (d, 3H).

Compound 20: HPLC-MS: $t_R$=3.3 min, (M+H)$^+$=341; Chiral HPLC (Method C): % ee=96.8; $^1$H-NMR (CDCl$_3$): δ 7.5 (m, 5H), 5.8 (m, 1H), 4.9 (dd, 1H), 4.6 (m, 1H), 4.3 (td, 1H), 3.6 (td, 1H), 2.7 (s, 3H), 1.7 (d, 3H).

Compound 21: HPLC-MS: $t_R$=4.0 min, (M+H)$^+$=409; $^1$H-NMR (CDCl$_3$): δ 7.7 (d, 2H), 7.6 (d, 1H), 5.8 (m, 1H), 4.9 (dd, 1H), 4.6 (m, 1H), 4.3 (td, 1H), 3.6 (m, 1H), 2.7 (s, 3H), 1.7 (d, 3H); $^{19}$F-NMR (CDCl$_3$): δ −60.1.

Compound 22: HPLC-MS: $t_R$=3.7 min, (M+H)$^+$=373; Chiral HPLC (Method B): % ee>99.7; $^1$H-NMR (CDCl$_3$): δ 7.5 (m, 2H), 7.3 (m, 2H), 5.8 (m, 1H), 4.9 (dd, 1H), 4.6 (m, 1H), 4.3 (m, 1H), 3.6 (m, 1H), 2.7 (s, 3H), 2.2-2.0 (m, 2H), 1.1 (m, 3H); $^{19}$F-NMR (CDCl$_3$): δ −98.4.

Compound 23: is racemate of compound 22.

Compound 24: HPLC-MS: $t_R$=4.0 min, (M+H)$^+$=387; Chiral HPLC (Method D): % ee=95.5; $^1$H-NMR (CDCl$_3$): δ 7.5 (m, 2H), 7.2 (m, 2H), 5.8 (m, 1H), 4.9 (m, 1H), 4.6 (m, 1H), 4.2 (m, 1H), 3.6 (m, 1H), 2.7 (s, 3H), 2.1-2.0 (m, 2H), 1.6 (m, 2H), 1.0 (m, 3H); $^{19}$F-NMR (CDCl$_3$): δ −98.2.

Compound 25: HPLC-MS: $t_R$=3.5 min, (M+H)$^+$=389; $^1$H-NMR (CDCl$_3$): δ 7.2 (m, 2H), 7.0 (m, 2H), 5.8 (m, 1H), 4.9 (dd, 1H), 4.6 (m, 1H), 4.3 (td, 1H), 3.9 (s, 3H), 3.5 (td, 1H), 2.7 (s, 3H), 1.8 (d, 3H); $^{19}$F-NMR (CDCl$_3$): δ −76.3.

Compound 26: HPLC-MS: $t_R$=3.5 min, (M+H)$^+$=355; $^1$H-NMR (CDCl$_3$): δ 7.4-7.2 (m, 4H), 6.3 (m, 1H), 5.3-4.8 (m, 2H), 4.3-3.8 (m, 1H), 3.5-3.4 (m, 1H), 2.7 (2s, 3H), 2.3 (s, 3H). 1.7 (2s, 3H).

Compound 27: HPLC-MS: $t_R$=3.4 min, (M+H)$^+$=371; $^1$H-NMR (CDCl$_3$): δ7.4 (m, 1H), 7.0 (m, 3H), 5.8 (m, 1H), 4.9 (dd, 1H), 4.6 (m, 1H), 4.3 (td, 1H), 3.8 (s, 3H), 3.5 (td, 1H), 2.7 (s, 3H), 1.7 (d, 3H).

Compound 28: HPLC-MS: $t_R$=3.1 min, (M+H)$^+$=343; Chiral HPLC (Method C): % ee=96.1; $^1$H-NMR (CDCl$_3$): δ7.5 (m, 2H), 7.2 (m, 2H), 5.8 (m, 1H), 4.9 (dd, 1H), 4.6 (m, 1H), 4.3 (td, 1H), 3.5 (td, 1H), 2.5 (s, 3H), 1.7 (d, 3H); $^{19}$F-NMR (CDCl$_3$): δ −98.3.

Compound 29: HPLC-MS: $t_R$=3.2 min, (M+H)$^+$=366; Chiral HPLC (Method B): % ee=99.0; $^1$H-NMR (CDCl$_3$): δ 7.8 (d, 2H), 7.6 (d, 2H), 5.8 (m, 1H), 4.9 (dd, 1H), 4.6 (m, 1H), 4.3 (td, 1H), 3.6 (td, 1H), 2.7 (s, 3H), 1.7 (d, 3H).

Compound 30: HPLC-MS: $t_R$=4.9 min, (M+H)$^+$=421; Chiral HPLC (Method A): % ee=98.2; $^1$H-NMR (CDCl$_3$): δ7.7 (d, 2H), 7.5 (d, 2H), 7.4 (m, 2H), 7.1 (m, 1H), 5.9 (m, 1H), 4.8 (dd, 1H), 4.7 (m, 1H), 4.3 (td, 1H), 3.6 (td, 1H), 2.9 (q, 2H), 1.8 (d, 3H), 1.4 (t, 3H).

Compound 31: is racemate of compound 10.
Compound 32: is racemate of compound 9.
Compound 33: is racemate of compound 8.
Compound 34: is racemate of compound 7.
Compound 35: is racemate of compound 6.
Compound 36: is racemate of compound 4.
Compound 37: is racemate of compound 3.
Compound 38: is racemate of compound 1.
Compound 39: is racemate of compound 2.
Compound 40: is racemate of compound 13.

Compound 41: HPLC-MS: $t_R$=4.8 min, (M+H)$^+$=413; Chiral HPLC (Method B): % ee=99.7; $^1$H-NMR (CDCl$_3$): δ7.5 (m, 2H), 7.2 (m, 2H), 5.8 (m, 1H), 4.9 (dd, 1H), 4.6 (m, 1H), 4.3 (td, 1H), 3.6 (td, 1H), 1.8 (d, 3H); $^{19}$F-NMR (CDCl$_3$): δ −62.9, −98.7.

Compound 42: HPLC-MS: $t_R$=4.3 min, (M+H)$^+$=395; Chiral HPLC (Method B): % ee=97.4; $^1$H-NMR (CDCl$_3$): δ 7.5 (m, 2H), 7.1 (m, 2H), 6.8 (t, $J_{H-F}$=53.5 Hz, 1H), 5.8 (m, 1H), 4.9 (dd, J=3.1, 13.6 Hz, 1H), 4.6 (m, 1H),), 4.3 (dt, J=4.6, 13.3 Hz, 1H), 3.6 (m, 1H), 1.8 (d, J=6.9 Hz, 3H); $^{19}$F-NMR (CDCl$_3$): δ −105.2 (s, 1F), −113.4 (dd, J=9.6, 53.4 Hz, 2F).

Compound 43: HPLC-MS: $t_R$=4.4 min, (M+H)$^+$=393; Chiral HPLC (Method C): % ee=96.3; $^1$H-NMR (CDCl$_3$): δ 7.5 (m, 2H), 7.2 (m, 2H), 5.9 (m, 1H), 4.8 (dd, J=3.3, 13.5 Hz, 1H), 4.6 (m, 1H), 4.3 (dt, J=4.2, 12.7 Hz, 1H), 3.6 (m, 1H), 2.2 (t, J=8.6 Hz, 3H), 1.8 (d, J=6.9 Hz, 3H); $^{19}$F-NMR (CDCl$_3$): δ −88.3 (q, J=18.3 Hz, 2F), −105.0 (s, 1F).

Compound 44: HPLC-MS: $t_R$=4.4 min, (M+H)$^+$=411; Chiral HPLC (Method C): % ee=98.6; $^1$H-NMR (CDCl$_3$): δ 7.5 (m, 2H), 7.2 (m, 2H), 5.8 (m, 1H), 4.8 (dd, J=3.5, 13.6 Hz, 1H), 4.6 (m, 1H), 4.3 (dt, J=4.0, 12.2 Hz, 1H), 3.7 (q, J=10.0 Hz, 2H), 3.6 (m, 1H), 1.8 (d, J=6.9 Hz, 3H); $^{19}$F-NMR (CDCl$_3$): δ −61.1 (t, J=9.6 Hz, 1F), −105.0 (s, 1F).

Compound 45: HPLC-MS: $t_R$=4.4 min, (M+H)$^+$=375; Chiral HPLC (Method C): % ee=98.5; $^1$H-NMR (CDCl$_3$): δ 7.5 (m, 2H), 7.2 (m, 2H), 5.9 (m, 1H), 5.8 (m, 1H), 4.9 (m, 1H), 4.6 (m, 1H), 4.3 (m, 1H), 3.6 (m, 1H), 1.9 (d, J=6.9 Hz, 3H), 1.8 (m, 3H); $^{19}$F-NMR (CDCl$_3$): δ −105.0 (s, 1F), −175.0 (m, 1F).

Compound 45-1: HPLC-MS: $t_R$=4.4 min, (M+H)$^+$=375; Chiral HPLC (Method C): % ee=99.2; $^1$H-NMR (CDCl$_3$): δ 7.5 (m, 2H), 7.2 (m, 2H), 5.9 (m, 1H), 5.8 (m, 1H), 4.9 (m, 1H), 4.6 (m, 1H), 4.3 (m, 1H), 3.6 (m, 1H), 1.9 (d, J=6.9 Hz, 3H), 1.8 (m, 3H); $^{19}$F-NMR (CDCl$_3$): δ −105.0 (s, 1F), −175.0 (m, 1F).

Compound 45-2: HPLC-MS: $t_R$=4.4 min, (M+H)$^+$=375; Chiral HPLC (Method C): % ee=91.7; $^1$H-NMR (CDCl$_3$): δ 7.5 (m, 2H), 7.2 (m, 2H), 5.9 (m, 1H), 5.8 (m, 1H), 4.9 (m, 1H), 4.6 (m, 1H), 4.3 (m, 1H), 3.6 (m, 1H), 1.9 (d, J=6.9 Hz, 3H), 1.8 (m, 3H); $^{19}$F-NMR (CDCl$_3$): δ −105.0 (s, 1F), −175.0 (m, 1F).

Biology Examples

Functional Assay

Aequorin Assay with Human NK-3 Receptor

Changes in intracellular calcium levels are a recognized indicator of G protein-coupled receptor activity. The efficacy of compounds of the invention to inhibit NKA-mediated NK-3 receptor activation was assessed by an in vitro Aequorin functional assay. Chinese Hamster Ovary recombinant cells expressing the human NK-3 receptor and a construct that encodes the photoprotein apoaequorin were used for this assay. In the presence of the cofactor coelenterazine, apoaequorin emits a measurable luminescence that is proportional to the amount of intracellular (cytoplasmic) free calcium.

Antagonist Testing

The antagonist activity of compounds of the invention is measured following pre-incubation (3 minutes) of the compound (at various concentrations) with the cells, followed by addition of the reference agonist (NKA) at a final concentration equivalent to the EC$_{80}$ (3 nM) and recording of emitted light (FDSS 6000 Hamamatsu) over the subsequent 90-second period. The intensity of the emitted light is integrated using the reader software. Compound antagonist activity is measured based on the concentration-dependent inhibition of the luminescence response to the addition of Neurokinin A.

Inhibition curves are obtained for compounds of the invention and the concentrations of compounds which inhibit 50% of reference agonist response (IC$_{50}$) were determined (see results in table 2 below). The IC$_{50}$ values shown in table 2 indicate that compounds of the invention are potent NK-3 antagonist compounds.

Competitive Binding Assays

The affinity of compounds of the invention for the human NK-3 receptor was determined by measuring the ability of compounds of the invention to competitively and reversibly displace a well-characterized NK-3 radioligand in a concentration-dependent manner.

$^3$H-SB222200 Binding Competition Assay with Human NK-3 Receptor

The ability of compounds of the invention to inhibit the binding of the NK-3 receptor selective antagonist $^3$H-SB222200 was assessed by an in vitro radioligand binding assay. Membranes were prepared from Chinese hamster ovary recombinant cells stably expressing the human NK-3 receptor. The membranes were incubated with 5 nM $^3$H-SB222200 (ARC) in a HEPES 25 mM/NaCl 0.1M/CaCl$_2$ 1 mM/MgCl$_2$ 5 mM/BSA 0.5%/Saponin 10 µg/ml buffer at pH 7.4 and various concentrations of compounds of the invention. The amount of $^3$H-SB222200 bound to the receptor was determined after filtration by the quantification of membrane associated radioactivity using the TopCount-NXT reader (Packard). Competition curves were obtained for compounds of the invention and the concentration that displaced 50% of bound radioligand (IC$_{50}$) were determined by linear regression analysis and then the apparent inhibition constant (K$_i$) values were calculated by the following equation: K$_i$=IC$_{50}$/(1+[L]/K$_d$) where [L] is the concentration of free radioligand and K$_d$ is its dissociation constant at the receptor, derived from saturation binding experiments (Cheng and Prusoff, 1973) (see results in table 2 below).

Table 2 shows biological results obtained using the $^3$H-SB222200 binding competition assay with compounds of the invention. These results indicate that compounds of the invention display potent affinity for the human NK-3 receptor.

TABLE 2

| Cpd no | Functional assay: Aequorin assay with human NK-3 receptor hNK-3 - AEQ(antagonist IC$_{50}$, nM) | Competitive binding assay with human NK-3 receptor hNK-3 (K$_i$, nM) |
| --- | --- | --- |
| 1 | 16 | 11 |
| 2 | 12 | 15 |
| 3 | 32 | 19 |

TABLE 2-continued

| Cpd no | Functional assay: Aequorin assay with human NK-3 receptor hNK-3 - AEQ(antagonist IC$_{50}$, nM) | Competitive binding assay with human NK-3 receptor hNK-3 (K$_i$, nM) |
|---|---|---|
| 4 | 19 | 20 |
| 5 | 18 | 23 |
| 6 | 30 | 24 |
| 7 | 30 | 26 |
| 8 | 33 | 26 |
| 9 | 21 | 30 |
| 10 | 56 | 31 |
| 11 | 73 | 32 |
| 12 | 170 | 59 |
| 13 | 44 | 40 |
| 14 | 57 | 42 |
| 15 | 50 | 45 |
| 16 | 71 | 49 |
| 17 | 50 | 51 |
| 18 | 87 | 54 |
| 19 | 110 | 56 |
| 20 | 93 | 60 |
| 21 | 150 | 63 |
| 22 | 130 | 69 |
| 23 | 220 | 150 |
| 24 | 120 | 78 |
| 25 | 110 | 85 |
| 26 | 74 | 88 |
| 27 | 220 | 100 |
| 28 | 160 | 110 |
| 29 | 170 | 150 |
| 30 | 5 | 7 |
| 31 | 64 | 70 |
| 32 | 44 | 59 |
| 33 | 120 | 89 |
| 34 | 62 | 38 |
| 35 | 54 | 73 |
| 36 | 58 | 43 |
| 37 | 52 | 41 |
| 38 | 34 | 26 |
| 39 | 32 | 28 |
| 40 | 130 | 83 |
| 41 | 7 | 11 |
| 42 | 39 | 48 |
| 43 | 136 | 59 |
| 44 | 204 | 45 |
| 45 | 244 | 101 |
| 45-1 | 285 | 100 |
| 45-2 | 148 | 83 |

Selectivity Assay

Selectivity of the compounds of the invention was determined over the other human NK receptors, namely NK-1 and NK-2 receptors.

Human NK-1

The affinity of compounds of the invention for the NK-1 receptor was evaluated in CHO recombinant cells which express the human NK-1 receptor. Membrane suspensions were prepared from these cells. The following radioligand: [$^3$H] substance P (PerkinElmer Cat #NET111520) was used in this assay. Binding assays were performed in a 50 mM Tris/5 mM MnCl2/150 mM NaCl/0.1% BSA at pH 7.4. Binding assays consisted of 25 µl of membrane suspension (approximately 5 µg of protein/well in a 96 well plate), 50 µl of compound or reference ligand (Substance P) at increasing concentrations (diluted in assay buffer) and 2 nM [$^3$H] substance P. The plate was incubated 60 min at 25° C. in a water bath and then filtered over GF/C filters (Perkin Elmer, 6005174, presoaked in 0.5% PEI for 2 h at room temperature) with a Filtration unit (Perkin Elmer). The radioactivity retained on the filters was measured by using the TopCount-NXT reader (Packard). Competition curves were obtained for compounds of the invention and the concentrations of compounds which displaced 50% of bound radioligand (IC$_{50}$) were determined and then apparent inhibition constant Ki values were calculated by the following equation: Ki=IC$_{50}$/(1+[L]/K$_D$) where [L] is the concentration of free radioligand and K$_D$ is its dissociation constant at the receptor, derived from saturation binding experiments (Cheng and Prusoff, 1973).

Human NK-2

The affinity of compounds of the invention for the NK-2 receptor was evaluated in CHO recombinant cells which express the human NK-2 receptor. Membrane suspensions were prepared from these cells. The following radioligand [$^{125}$I]-Neurokinin A (PerkinElmer Cat #NEX252) was used in this assay. Binding assays were performed in a 25 mM HEPES/1 mM CaCl$_2$)/5 mM MgCl2/0.5% BSA/10 µg/ml saponin, at pH 7.4. Binding assays consisted of 25 µl of membrane suspension (approximately 3.75 µg of protein/well in a 96 well plate), 50 µl of compound or reference ligand (Neurokinin A) at increasing concentrations (diluted in assay buffer) and 0.1 nM [$^{125}$I]-Neurokinin A. The plate was incubated 60 min at 25° C. in a water bath and then filtered over GF/C filters (Perkin Elmer, 6005174, presoaked in assay buffer without saponine for 2 h at room temperature) with a Filtration unit (Perkin Elmer). The radioactivity retained on the filters was measured by using the TopCount-NXT reader (Packard). Competition curves were obtained for compounds of the invention and the concentrations of compounds which displaced 50% of bound radioligand (IC$_{50}$) were determined and then apparent inhibition constant Ki values were calculated by the following equation: Ki=IC$_{50}$/(1+[L]/K$_D$) where [L] is the concentration of free radioligand and K$_D$ is its dissociation constant at the receptor, derived from saturation binding experiments (Cheng and Prusoff, 1973).

The compounds of the invention, which were tested in the above NK-1 and NK-2 described assays, demonstrated a low affinity at the human NK-1 and human NK-2 receptors: more than 200 fold shift of the K$_i$ compared to the human NK-3 receptor (table 3). Thus, compounds according to the invention have been shown to be selective over NK-1 and NK-2 receptors.

TABLE 3

| Cpd no | hNK-3 (K$_i$, nM) | hNK-1 (K$_i$, nM) | hNK-2 (K$_i$, nM) |
|---|---|---|---|
| 1 | 11 | 10300 | 7500 |
| 2 | 15 | 23800 | >30000 |
| 3 | 19 | >30000 | >30000 |
| 4 | 20 | 19900 | 23000 |
| 5 | 23 | >30000 | >30000 |
| 6 | 24 | 22100 | 25000 |
| 7 | 26 | >30000 | 36000 |
| 8 | 26 | >30000 | >30000 |
| 9 | 30 | >30000 | >30000 |
| 10 | 31 | >30000 | 49000 |
| 11 | 32 | 22000 | >30000 |
| 12 | 59 | NA | NA |
| 13 | 40 | >30000 | >30000 |
| 14 | 42 | >30000 | >30000 |
| 15 | 45 | >30000 | >30000 |
| 16 | 49 | >30000 | 37000 |
| 17 | 51 | >30000 | >30000 |
| 18 | 54 | >30000 | >30000 |
| 19 | 56 | >30000 | >30000 |
| 20 | 60 | >30000 | >30000 |
| 21 | 63 | >30000 | >30000 |
| 22 | 69 | >30000 | >30000 |
| 23 | 150 | NA | NA |
| 24 | 78 | >30000 | >30000 |
| 25 | 85 | >30000 | >30000 |
| 26 | 88 | >30000 | >30000 |
| 27 | 100 | >30000 | >30000 |

TABLE 3-continued

| Cpd no | hNK-3 ($K_i$, nM) | hNK-1 ($K_i$, nM) | hNK-2 ($K_i$, nM) |
|---|---|---|---|
| 28 | 110 | >30000 | >30000 |
| 29 | 150 | >30000 | >30000 |
| 30 | 7 | 40000 | 32000 |
| 31 | 70 | >30000 | >30000 |
| 32 | 59 | >30000 | >30000 |
| 33 | 89 | >30000 | >30000 |
| 34 | 38 | >30000 | >30000 |
| 35 | 73 | >30000 | 30000 |
| 36 | 43 | >30000 | 36000 |
| 37 | 41 | 32000 | >30000 |
| 38 | 26 | 21000 | 28000 |
| 39 | 28 | >30000 | >30000 |
| 40 | 83 | >30000 | >30000 |
| 41 | 11 | NA | NA |
| 42 | 48 | >30000 | >30000 |
| 43 | 59 | >30000 | >30000 |
| 44 | 45 | >30000 | >30000 |
| 45 | 101 | >30000 | >30000 |
| 45-1 | 100 | >30000 | >30000 |
| 45-2 | 83 | >30000 | >30000 |

NA: not available hERG Inhibition Assay

The human ether-a-go-go related gene (hERG) encodes the inward rectifying voltage gated potassium channel in the heart ($I_{Kr}$) which is involved in cardiac repolarisation. $I_{Kr}$ current inhibition has been shown to elongate the cardiac action potential, a phenomenon associated with increased risk of arrhythmia. $I_{Kr}$ current inhibition accounts for the vast majority of known cases of drug-induced QT-prolongation. A number of drugs have been withdrawn from late stage clinical trials due to these cardiotoxic effects, therefore it is important to identify inhibitors early in drug discovery.

The hERG inhibition study aims at quantifying the in vitro effects of compounds of the invention on the potassium-selective $IK_r$ current generated in normoxic conditions in stably transfected HEK 293 cells with the human ether-a-go-go-related gene (hERG).

Whole-cell currents (acquisition by manual patch-clamp) elicited during a voltage pulse were recorded in baseline conditions and following application of tested compounds (5 minutes of exposure). The concentrations of tested compounds (0.3 µM; 3 µM; 10 µM; 30 µM) reflect a range believed to exceed the concentrations at expected efficacy doses in preclinical models.

The pulses protocol applied is described as follow: the holding potential (every 3 seconds) was stepped from −80 mV to a maximum value of +40 mV, starting with −40 mV, in eight increments of +10 mV, for a period of 1 second. The membrane potential was then returned to −55 mV, after each of these incremented steps, for 1 second and finally repolarized to −80 mV for 1 second.

The current density recorded were normalized against the baseline conditions and corrected for solvent effect and time-dependent current run-down using experimental design in test compound free conditions.

Inhibition curves were obtained for compounds and the concentrations which decreased 50% of the current density determined in the baseline conditions ($IC_{50}$) were determined. All compounds for which the $IC_{50}$ value is above 10 µM are not considered to be potent inhibitors of the hERG channel whereas compounds with $IC_{50}$ values below 1 µM are considered potent hERG channel inhibitors.

When tested in the hERG inhibition assay, compounds of the invention were determined to have $IC_{50}$ values as shown in Table 4.

Determination of plasma protein binding The pharmacokinetic and pharmacodynamic properties of chemicals/drugs are largely a function of the reversible binding of chemicals to plasma or serum proteins. Generally, only the unbound or "free fraction" of a drug is available for diffusion or transport across cell membranes, and for interaction with a pharmacological/toxicological target. Consequently, the extent of the plasma protein binding (PPB) of a compound influences its action as well as its distribution and elimination.

The determination of plasma protein binding (PPB) of a compound is enabled by equilibrium dialysis, an accepted and standard method for reliable estimation of the non-bound drug fraction in plasma. RED (Rapid Equilibrium Dialysis) device insert is made of two side-by-side chambers separated by an O-ring-sealed vertical cylinder of dialysis membrane (MWCO ~8,000). Plasma containing drug (at 5 µM or blood concentrations otherwise corresponding to efficacious doses, if known) is added to one chamber while buffer is added to the second. After 4 hours incubation at 37° C. under shaking, an aliquot is removed from each chamber and analyzed by a LC-MS/MS procedure enables the determination of both free and bound drug.

The percentages provided in Table 4 represent for the compounds of the invention the bound drug fraction to the plasma protein. The "free fraction" may be calculated as 100%−% rPPB (i.e. the complementary percentage of that disclosed in Table 4, corresponding to the drug concentration that is unbound and therefore available to engage biological target and elicit pharmacological activity).

TABLE 4

| Cpd no | Exposure (% rPPB) | CardioSafety (hERG $IC_{50}$, µM) |
|---|---|---|
| 1 | 67 | 42 |
| 2 | 47 | 32 |
| 3 | 42 | 66 |
| 4 | 40 | 70 |
| 5 | 22 | 70 |
| 6 | 53 | 45 |
| 7 | 26 | 70 |
| 8 | 29 | 70 |
| 9 | 22 | 70 |
| 10 | 30 | 70 |
| 11 | 24 | 50 |
| 12 | 20 | NA |
| 13 | 37 | 70 |
| 14 | 21 | NA |
| 15 | 20 | 70 |
| 16 | 36 | 70 |
| 17 | 24 | 46 |
| 18 | 23 | 70 |
| 19 | 51 | NA |
| 20 | 26 | 50 |
| 21 | 38 | 45 |
| 22 | 27 | 70 |
| 23 | 34 | NA |
| 24 | 48 | 61 |
| 25 | 19 | NA |
| 26 | 19 | NA |
| 27 | 24 | 70 |
| 28 | 12 | NA |
| 29 | 10 | 59 |
| 30 | 94 | 32 |
| 31 | 31 | NA |
| 32 | 25 | NA |
| 33 | 29 | NA |
| 34 | 24 | NA |
| 35 | 52 | NA |
| 36 | 60 | NA |
| 37 | 53 | NA |
| 38 | 76 | NA |
| 39 | 43 | NA |

TABLE 4-continued

| Cpd no | Exposure (% rPPB) | CardioSafety (hERG $IC_{50}$, µM) |
|---|---|---|
| 40 | 24 | NA |
| 41 | 55 | NA |
| 42 | 16 | NA |
| 43 | 47 | NA |
| 44 | 31 | NA |
| 45 | 31 | NA |
| 45-1 | 27 | NA |
| 45-2 | 33 | NA |

NA: not available

In Vivo Assay to Assess Compound Activity in Rat (Oral Dosing)

Castrated male rat model to assess the effect of compound of invention on circulating levels of luteinizing hormone (LH)

The effect of compounds of the invention to inhibit luteinizing hormone (LH) secretion is determined by the following biological studies.

In humans and rodents, castration is well-precedented to permit heightened, persistent GnRH signaling and consequent elevation of circulating LH. Thus, a castrated rat model is used to provide a broad index for measurement of LH inhibition as a marker of test compound inhibition of the GnRH signaling pathway.

Castrated adult male Sprague-Dawley (SD) rats (150-175 g) were purchased from Janvier (St Berthevin, France). All animals were housed 2 per cage in a temperature-controlled room (22±2° C.) and 50±5% relative humidity with a 12 hour/12 hour light/dark cycles (lights off at 6 h00 pm). The animals were allowed 3 weeks of postoperative recovery prior to study. Animals were handled on a daily basis. Standard diet and tap water were provided ad libitum. Animal cage litters were changed once a week. On the study day, animals were acclimated to the procedure room for a period of one hour prior to the initiation of the experiment.

Compounds of the invention were formulated in 0.5% methyl cellulose.

After basal sampling (TO) a single dose of compounds of the invention or vehicle was administered orally to rats. Blood samples were then collected at several time points post dosing (45, 90, 150, 300 and 420 minutes). Blood samples were obtained via tail vein bleed, drawn into EDTA-containing tubes and centrifuged immediately. Plasma samples were collected and stored in a −80° C. freezer until assayed. Serum LH levels were determined using radioimmunoassay kit from RIAZEN—Rat LH, Zentech (Liege, Belgium). Baseline was defined as the initial basal blood sample.

When tested in the castrated male rat model described above, compounds no 1, 2, 4, 5, 8, 9, 11, 13, 20 and 30 of the invention significantly suppressed circulating LH levels (statistically significant, $p<0.05$) at a dose less than or equal to 30 mg/kg).

Effect of Compounds of the Invention on Plasma Testosterone in Gonad Intact Male Rats The study was designed to evaluate the effect of compounds of the invention on testosterone circulating levels following oral administration at 3 mg/kg on SD gonad intact male rats.

Briefly the experimental methods used for this study were as follows:

Two groups of non-fasted rats (male, Sprague-Dawley, 200 to 225 g; n=4 rats/group) with jugular vein cannulation, were dosed via a single oral administration of compounds of the invention at 3 mg/kg. The control group was dosed with the vehicle. Compounds of the invention were prepared in a dose formulation of pyrogen-free water with 0.5% methylcellulose. Blood samples were collected via the catheter implanted in the jugular vein at pre-determined intervals using EDTA-3K as anti-coagulant. Samples were chilled and rapidly processed by centrifugation to obtain corresponding plasma samples. Testosterone hormone levels were determined by RIA performed on plasma samples collected for all the groups at 5 minutes before administration (basal time), and at 45, 90, 150, 300, 480 minutes and 24 hours after dosing.

When tested in the gonad intact male rats, compound no 5 significantly suppressed plasma testosterone level over the test period as compared to the vehicle treated group (FIG. 1).

Effect of compounds of the invention on prostate weight reduction in a Benign Prostatic Hyperplasia (BPH) rat model. Briefly, adult male rats were injected daily for four weeks with testosterone to cause an enlargement of the prostate as per methods previously described in the literature (Scolnick et al., J. Andrology, 1994, 15(4), 287-297; Rick et al., J. Urol., 2012, 187, 1498-1504; see FIG. 2, Ctrl Neg vs BHP). Rats were than treated daily for three weeks with compounds of the invention. After 21 days treatment with compounds of the invention at 3, 10 or 30 mg/kg (q.d.; PO administration), the ratio of prostate to body weight (g prostate/100 g of body weight) was evaluated as an indicator of BPH. Treated groups were compared to the BPH group (Testosterone-induced BPH group followed 21 days of vehicle administration) or to the Control group (Corn oil injection for the induction phase followed by vehicle treatment rather than test compound). Comparison between groups was made by using One-Way ANOVA followed by Dunnett's test for statistical analysis.

Figure 2:
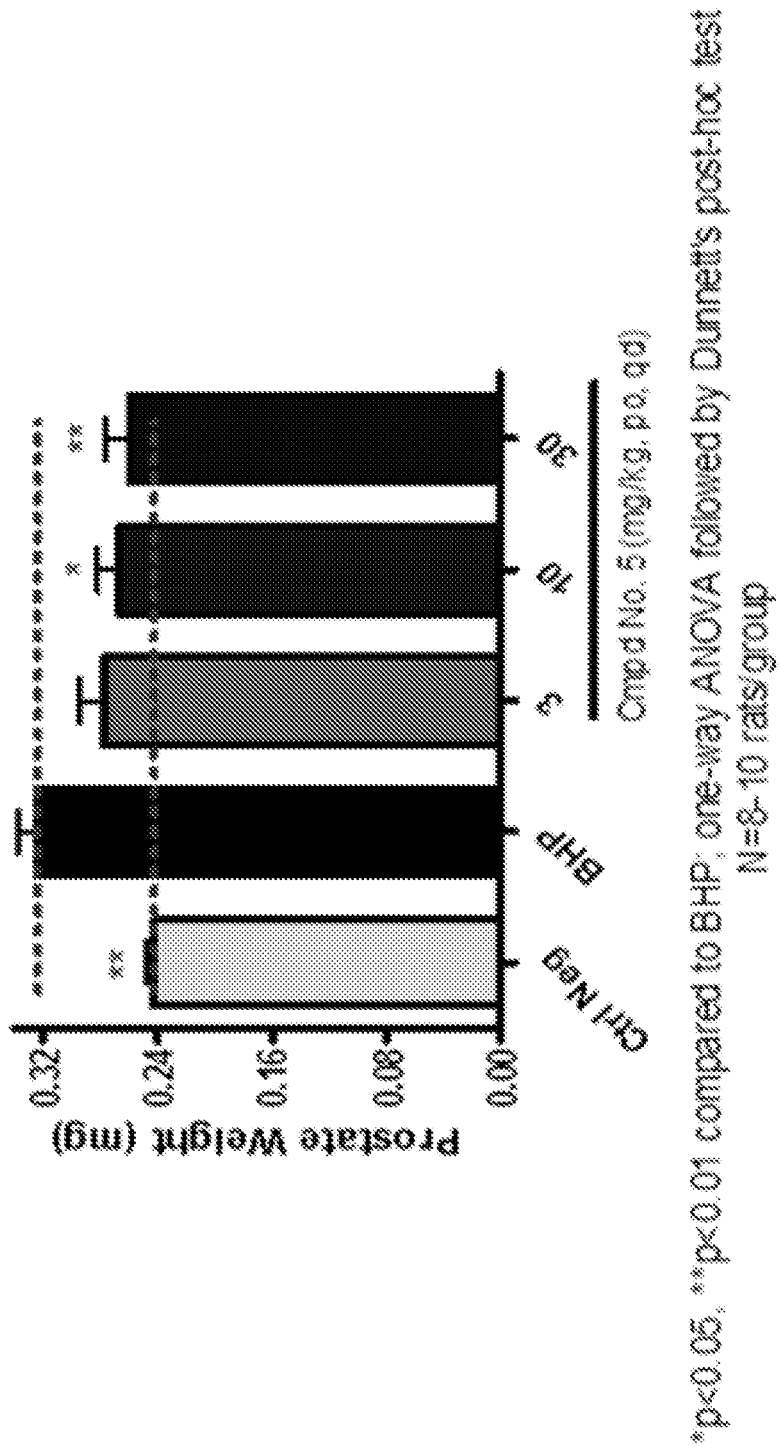
FIG. 2 is a histogram showing the prostate weight in a rat model of Benign Prostate Hyperplasia (BPH) after oral administration of 3, 10 or 30 mg/kg of compound no 5.

When tested in the Benign Prostatic Hyperplasia rat model, compound no 5, demonstrated a concentration-response to reduce prostate weight to normal levels (i.e. levels in rats not exposed to exogenous testosterone; FIG. 2).

Effect of compounds of the invention on Estradiol circulating level in female rats. The aim of this study was to evaluate the effect of compounds of the invention on plasma estradiol levels following oral administration at 10 mg/kg (b.i.d.) for a period of 10 days in female rats.

Figure 3:
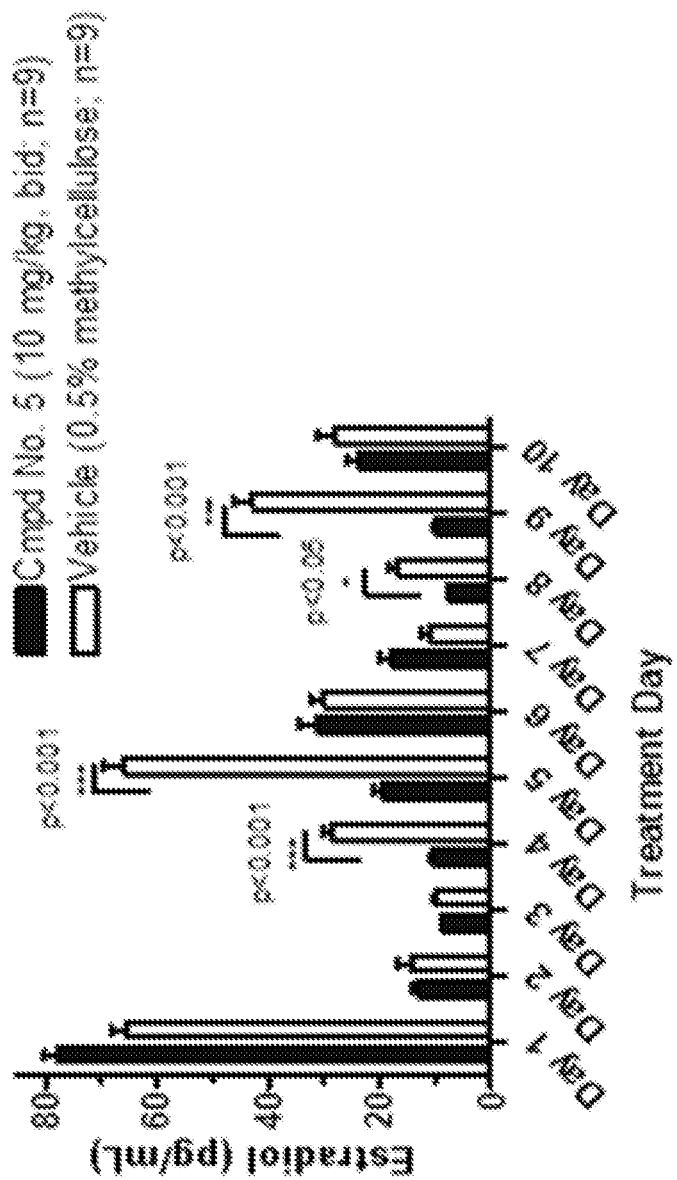
FIG. 3 is a histogram showing the estradiol levels in adult, female rats tracked over the duration of consecutive estrous cycles, after oral administration of compound no 5 (10 mg/kg) or of a vehicle (0.5% methyl cellulose).

Briefly the experimental methods used for this study were as follows:

Two groups of adult, female rats (Sprague-Dawley, ~320 g) were treated in-phase with their individual estrous cycles. Thus, treatment was started in the proestrus phase (coincident with peak estradiol levels, as shown on Day 1 in FIG. 3) and rats were dosed twice daily (~9 h30 and 17 h30) by oral administration either with a compound of the invention at 10 mg/kg or with the vehicle for the control group. Compounds of the invention were prepared in a dose formulation of pyrogen-free water with 0.5% methylcellulose. Estradiol levels were determined for all groups by ELISA performed on plasma samples derived from blood collections taken at 30 minutes before the daily, 9 h30 test article administration on all days presented in FIG. 3.

In vehicle-treated, adult female rats, estradiol peaks are observed every 4-5 days consistent with the anticipated duration of the rat estrous cycle. Treatment with compound no 5, significantly decreased estradiol levels over the time-course tracked over two consecutive estrous cycles. This finding is most apparent in the proestrus phase (i.e. for vehicle group, on Day 5 and Day 9) where estradiol levels rise coincident with ovulation.

In Vivo Assay in OVX Ewes—Activity in Thermoregulation

Experimental Methods: Evaluation of Thermoregulation in OVX Ewe

Ten Corriedale ewes (body weight 56.6±3.4 kg) of 3-4 years of age were ovariectomized according to Standard Operating Procedures, as previously described (Barker-Gibb, Scott, Boublik, & Clarke, 1995). After 4 months recovery, animals were acclimatised to housing in single pens for a period of 7 days with ad libitum access to water and chaffed lucerne hay. One day prior to experimentation, the animals received a jugular vein cannula (Dwellcath, Tuta Laboratories, Lane Cove, Australia). The cannula were kept patent with heparinised saline. On the day of the experiment, compound no 5 of the present invention was formulated in physiological saline with 9% 2-hydroxypropyl-p-cyclodextrin at a concentration of 2 mg/mL. Compound no 5 (1 mg/kg, N=5) or vehicle (N=5) was administered at 11 h00 by intravenous bolus injection at a dose volume of 0.5 mL/kg through the jugular cannula and the injected material was flushed into the animal with 5 mL of heparinised saline. Animals were fed at 12 h00. Rectal temperatures were monitored with a probe at hourly intervals throughout the experiment, starting at 7 h40 and concluding at 15 h40.

Results In response to feeding at 12 h00, vehicle-treated animals exhibited a transient, relative body temperature increase of >0.7° C. measured at 12 h40, consistent with findings previously reported in the literature (Henry, Dunshea, Gould, & Clarke, 2008).

Figure 4:
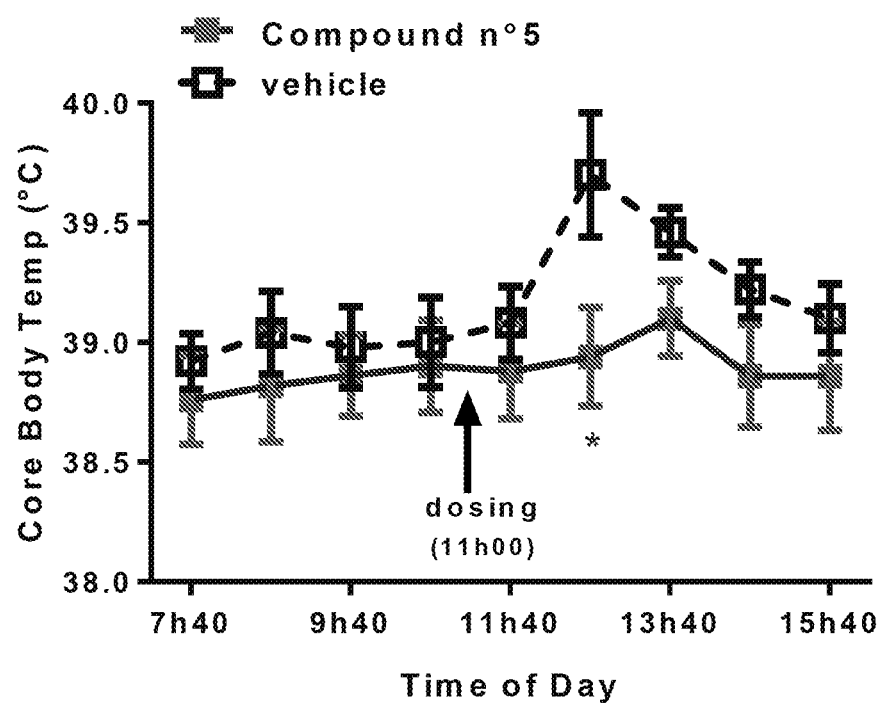
FIG. 4 is a graph showing the body temperature over time in ovariectomized ewes after intravenous administration of compound no 5 (1 mg/kg) or of a vehicle.

However, this pyrogenic response to feeding in ovarectomized ewes was not observed in any animals treated with compound no 5. Thus, at the 12 h40 time point, the body temperature of the vehicle-treated group (39.7±0.3° C.) was significantly (p<0.05) higher than that of the compound no 5-treated group (38.9±0.2° C.), as presented in FIG. 4. Graphical data presented as mean±SEM for vehicle-treated versus compound no 5-treated ewes (N=5/group). Statistical analyses performed by 2-way ANOVA followed by Sidak's Multiple Comparisons Test between treatment groups at the indicated time interval, *p<0.05.

Conclusions: Ovariectomy in the ewe causes changes in core body temperature considered analogous to menopausal hot flashes (MacLeay, Lehmer, Enns, Mallinckrodt, Bryant, & Turner, 2003) to the extent that a transient, pyrogenic response to feeding is observed (Henry, Dunshea, Gould, & Clarke, 2008). It is herein demonstrated that the compounds of the invention protect against this hot flash induced by feeding.

Therefore, the NK-3 receptor antagonists of the invention have therapeutic utility to protect against hot flashes in clinical situations where sex steroids (principally, estrogen in women and testosterone in men) are compromised, including such disorders as the induction of hot flashes due to menopause and the induction of hot flashes as a consequence of cancer therapy that lowers sex hormones (for example, therapy-induced hot flashes in breast, uterine and prostate cancer).

Clinical Evaluation of Compound no 5 for the Treatment of Menopausal Hot Flashes Experimental Methods:

Objectives: The study objective is to evaluate the effect of compound no 5 on the severity and frequency of hot flashes in postmenopausal women.

Design and Setting: The Phase 2a clinical trial was conducted in 80 patients, divided over 2 treatment groups of 40 patients each. One group received placebo while the other group received 90 mg of compound no 5 twice daily (BID) for a period of 12 weeks. The Phase 2a trial was double blind and randomized. This Phase 2a trial was conducted on healthy menopausal women (40-65 y) experiencing at least 49 moderate or severe hot flashes or night sweats over a period of 7 consecutive days in the screening period (maximum of 4 weeks). The study was conducted on an ambulatory basis where patients were asked to visit the clinical site on the first day of dosing and at weeks 4, 8, 12 during the treatment period with a follow-up visit 2-3 weeks after conclusion of dosing.

Hot flashes were to be reported daily in the morning and the evening using an electronic diary tool. These reported events were used to calculate the Hot Flash Frequency and the Hot Flash Score.

The weekly number of hot flashes was calculated in two ways: cumulatively for all severity grades, and cumulatively but leaving out the number of mild hot flashes. Hot Flash Frequencies were calculated for weeks 4 and 12.

The Hot Flash Score (HFS) is a composite score combining both frequency and severity. This score is an accepted method to assess the overall severity of the hot flash burden and is calculated weekly. The score is a general measure of the number and severity of all hot flashes occurred during a given time period. The Hot Flash Score (based on severity and frequency) is calculated as follows:

day-score=(number of mild hot flashes/day×1)+(number of moderate hot flashes/day×2)+(number of severe hot flashes/day×3)

The weekly hot flash score is calculated: Mean HFS day-score over 1 week

Scores were calculated for weeks 4 and 12

Higher scores indicate worse symptoms. There is no maximum score since the number of hot flashes does not have an upper limit.

Results: In response to treatment by compound no 5 (90 mg BID) both Score and Frequency of hot flashes in postmenopausal women were significantly reduced in comparison of placebo-controlled group as presented in Table 5 (Hot Flash Score) and in Table 6 (Hot Flash Frequencies). Data are presented as mean for placebo-treated versus compound no 5-treated patients (N=40/group). Statistical analyses performed by 2-way ANOVA.

Table 5 is a table showing the calculated Hot Flashes Score for moderate and severe hot flashes expressed as absolute change from baseline after oral administration of compound no 5 (90 mg BID) or of a placebo.

| | | Mean | | |
|---|---|---|---|---|
| Endpoint | Visit | Compound no5 | Placebo | P value |
| Hot Flash Score | Baseline | 29.08 | 25.92 | n.s. |
| | Week 4 | 2.96 | 15.69 | <0.0001 |
| | Week 12 | 1.70 | 13.68 | <0.0001 |

Table 6 is a table showing the calculated Hot Flashes Frequency for moderate and severe hot flashes expressed as absolute change from baseline after oral administration of compound no 5 (90 mg BID) or of a placebo.

| | | Mean | | |
|---|---|---|---|---|
| Endpoint | Visit | Compound no5 | Placebo | P value |
| Frequency | Baseline | 11.84 | 10.72 | n.s. |
| | Week 4 | 1.35 | 6.6 | <0.0001 |
| | Week 12 | 0.79 | 5.6 | <0.0001 |

Conclusions:

This well-controlled, Clinical trial study has been sufficiently powered to provide clear insight into the therapeutic value of compound no 5 for the treatment of menopausal hot flashes. It is herein demonstrated that the compounds of the invention can effectively prevent the occurrence of moderate and severe hot flashes in postmenopausal women.

Therefore, the NK-3 receptor antagonists of the invention have therapeutic utility to protect against hot flashes in clinical situations where sex steroids (principally, estrogen in women and testosterone in men) are compromised, including such disorders as the induction of hot flashes due to menopause and the induction of hot flashes as a consequence of hormone therapy intentionally lowering the level of sex hormones (for example, therapy-induced hot flashes in breast, uterine and prostate cancer).

Clinical Evaluation of compound no 5 for the Treatment of PolyCystic Ovary Syndrome (PCOS)

Experimental Methods:

Objectives: The study objectives are to evaluate the effect of compound no 5 on the serum levels of Total Testosterone (TT), Luteinizing Hormone (LH), Follicle Stimulating Hormone (FSH) and LH:FSH ratio after 12 weeks of treatment.

Design and Setting: The Phase 2a clinical trial was conducted in 48 patients, divided over 2 treatment groups of 24 patients each. One group received placebo while the other group received 180 mg of compound no 5 once daily (QD) for a period of 12 weeks. The Phase 2a trial was double blind and randomized. This Phase 2a trial was conducted on women (18-45 y) diagnosed with PCOS as per the Rotterdam Criteria and demonstrating biochemical hyperandrogenism, defined as TT>50 ng/dL [1.7 nmol/L] at screening. The study was conducted on an ambulatory basis where patients were asked to visit the clinical site on the first day of dosing and at weeks 3, 6, 9 and 12 during the treatment period with a follow-up visit 2-3 weeks after conclusion of dosing.

Blood draws for LH, FSH and TT were taken every visit between 2 and 8 hours after drug intake (baseline and week 3-6-12). At week 9 the blood samples were taken in the morning before drug intake (i.e. at trough PK concentrations for compound no 5). These blood draws were the basis for assessing the primary (TT) and secondary (LH, FSH, LH:FSH ratio) endpoints. The primary endpoint of Total Testosterone was measured according to GLP using an LC-MS/MS method.

PCOS is typically characterized by excessive ovarian androgen production, failure of ovulation, and slightly enlarged ovaries with numerous peripheral small follicles that appear as cysts. The disorder is commonly accompanied by infertility. Typically, the clinical features of PCOS are associated with hypersecretion of LH and androgens (TT) but with normal serum concentrations of FSH hormone. Laboratory examinations reveal elevated TT levels in about 50% of the patients, accompanied by an elevated LH:FSH ratio (>2) due to the imbalanced secretion of both hormones (a ratio of 1 is considered normal).

Results: In response to treatment by compound no 5 (180 mg QD) both TT and LH:FSH were significantly reduced in comparison of placebo-controlled group as presented in Table 7 (TT) and in Table 8 (LH:FSH). Data are presented as mean for placebo-treated versus compound no 5-treated patients (N=24/group). Statistical analyses performed by 2-way ANOVA comparing placebo to treatment. The significant decrease in the LH:FSH ratio reflects the observed significant decrease in LH with preserved FSH secretion.

Figure 5:
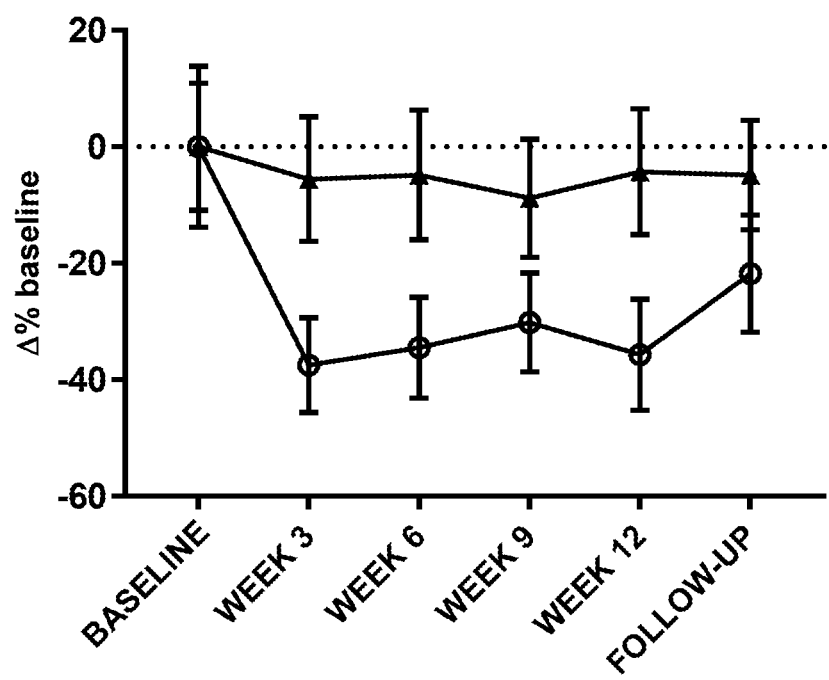
FIG. 5 is a graph showing the evolution of the primary endpoint (TT) during the course of the study as percent change from baseline (±SEM) after oral administration of compound no 5 (180 mg QD; circles) or placebo (triangles).

The evolution of the primary endpoint (decrease in TT) during the course of the study is presented in FIG. 5, showing a clear decreasing of TT during the 12 weeks of dosing and a clear rebound effect on circulating androgen levels after withdrawal from treatment, indicative of a direct relationship between drug intake and pharmacodynamic effect.

Table 7 is a table showing the actual values for Total Testosterone levels at baseline and after oral administration of compound no 5 (180 mg QD) or placebo.

| Endpoint | Visit | Mean Compound no5 | Placebo | P value |
| --- | --- | --- | --- | --- |
| Total Testosterone (nmol/L) | Baseline | 2.16 | 2.01 | n.s. |
| | Week 6 | 1.41 | 1.91 | * <0.05 |
| | Week 12 | 1.39 | 1.92 | * <0.05 |

Table 8 is a table showing the calculated actual values for LH:FSH ratio after oral administration of compound no 5 (180 mg QD) or placebo.

| Endpoint | Visit | Mean Compound no5 | Placebo | P value |
| --- | --- | --- | --- | --- |
| LH:FSH | Baseline | 2.67 | 2.60 | n.s. |
| | Week 6 | 1.19 | 2.45 | *** <0.001 |
| | Week 12 | 1.16 | 2.33 | *** <0.001 |

Conclusions:

This well-controlled, clinical trial study has been sufficiently powered to provide clear insight into the therapeutic value of compound no 5 for the treatment of PCOS. It is herein demonstrated that the compounds of the invention can effectively restore the hormonal balance of LH and FSH and decrease the testosterone levels in women with PCOS.

Therefore, the NK-3 receptor antagonists of the invention have therapeutic utility to restore the hormonal balance in clinical situations where the normal homeostasis of gonadotrophins (principally, luteinising hormone) is compromised, including disorders affecting the Hypothalamic-Pituitary-Gonadotropic function, such as the PCOS.

The invention claimed is:

1. A method for preventing and/or treating moderate hot flashes or severe hot flashes in a patient, wherein the method comprises administering to the patient in need thereof for at least four weeks a pharmaceutically effective amount of the following compound:

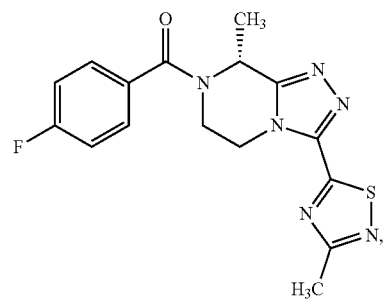 [SMILES: Cc1nsc(-c2nnc3n2CCN(C(=O)c2ccc(F)cc2)[C@@H]3C)n1]

wherein the frequency of moderate hot flashes or severe hot flashes in the patient after at least four weeks of treatment is reduced compared to the frequency of moderate hot flashes or severe hot flashes in the patient before at least four weeks of treatment.

2. The method according to claim 1, wherein the moderate hot flashes or severe hot flashes are related to a condition selected from the group consisting of a perimenopausal condition, a menopausal condition, and a postmenopausal condition, or a combination thereof.

3. The method according to claim 1, wherein the moderate hot flashes or severe hot flashes are a consequence of hormone therapy which intentionally lowers the level of sex hormones.

4. The method according to claim 3, wherein the moderate hot flashes or severe hot flashes are selected from the group consisting of therapy-induced moderate hot flashes in breast cancer, therapy-induced severe hot flashes in breast cancer, therapy-induced moderate hot flashes in uterine cancer, therapy-induced severe hot flashes in uterine cancer, therapy-induced moderate hot flashes in prostate cancer, and therapy-induced sever hot flashes in prostate cancer.

5. A method for preventing and/or treating moderate hot flashes or severe hot flashes in a patient, wherein the method comprises administering to the patient in need thereof for at least four weeks a pharmaceutically effective amount of the following compound:

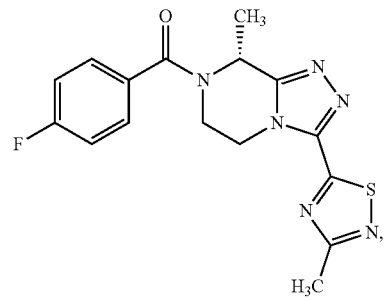 [SMILES: Cc1nsc(-c2nnc3n2CCN(C(=O)c2ccc(F)cc2)[C@@H]3C)n1]

wherein the severity of moderate hot flashes or severe hot flashes in the patient after at least four weeks of treatment is reduced compared to the severity of moderate hot flashes or severe hot flashes in the patient before at least four weeks of treatment.

6. The method according to claim 5, wherein the moderate hot flashes or severe hot flashes are related to a condition selected from the group consisting of a perimenopausal condition, a menopausal condition, and a postmenopausal condition, or a combination thereof.

7. The method according to claim 5, wherein the moderate hot flashes or severe hot flashes are a consequence of hormone therapy which intentionally lowers the level of sex hormones.

8. The method according to claim 7, wherein the moderate hot flashes or severe hot flashes are selected from the group consisting of therapy-induced moderate hot flashes in breast cancer, therapy-induced severe hot flashes in breast cancer, therapy-induced moderate hot flashes in uterine cancer, therapy-induced severe hot flashes in uterine cancer, therapy-induced moderate hot flashes in prostate cancer, and therapy-induced sever hot flashes in prostate cancer.

\* \* \* \* \*